(12) United States Patent
Wallace et al.

(10) Patent No.: US 10,610,245 B2
(45) Date of Patent: Apr. 7, 2020

(54) SELF-ROLLING THROMBECTOMY APPARATUSES AND METHODS

(71) Applicant: STRYKER CORPORATION, Fremont, CA (US)

(72) Inventors: Michael P. Wallace, Pleasanton, CA (US); E. Skott Greenhalgh, Gladwyne, PA (US)

(73) Assignee: Stryker Corporation, Fremont, CA (US)

( * ) Notice: Subject to any disclaimer, the term of this patent is extended or adjusted under 35 U.S.C. 154(b) by 123 days.

(21) Appl. No.: 15/700,685

(22) Filed: Sep. 11, 2017

(65) Prior Publication Data

US 2018/0070968 A1    Mar. 15, 2018

Related U.S. Application Data

(60) Provisional application No. 62/393,460, filed on Sep. 12, 2016.

(51) Int. Cl.
*A61B 17/22*     (2006.01)
*A61B 17/221*    (2006.01)
(Continued)

(52) U.S. Cl.
CPC ...... *A61B 17/22031* (2013.01); *A61B 17/221* (2013.01); *A61B 17/3205* (2013.01); *A61B 2017/00398* (2013.01); *A61B 2017/2215* (2013.01); *A61B 2017/22038* (2013.01); *A61B 2017/22079* (2013.01); *A61B 2017/3425* (2013.01); *A61B 2217/005* (2013.01)

(58) Field of Classification Search
CPC ...... A61F 2/01; A61F 2/013; A61F 2002/011; A61B 17/221; A61B 17/22012; A61B 17/22031; A61B 17/22032; A61B 17/22034; A61B 17/22035; A61B 17/22038; A61B 17/22079; A61B 17/2215; A61B 17/3435; A61M 25/0119
See application file for complete search history.

(56) References Cited

U.S. PATENT DOCUMENTS 4,222,380 A    9/1980    Terayama
4,243,040 A    1/1981    Beecher
(Continued)

FOREIGN PATENT DOCUMENTS

AU    2015210338    8/2015
GB    1588072       4/1981
(Continued)

OTHER PUBLICATIONS

Extended European Search Report dated Oct. 5, 2018 for European patent appln No. 18174891.4.
(Continued)

*Primary Examiner* — Melanie R Tyson
(74) *Attorney, Agent, or Firm* — Vista IP Law Group, LLP

(57) ABSTRACT

Self-rolling mechanical atherectomy aka thrombectomy apparatuses for removing a clot from a vessel include a tractor tube portion that rolls and inverts over itself in a continuous motion, tractor-like, to draw material into the tractor tube, wherein the tractor tube rolls over itself without requiring any additional internal support at the distal-facing region of the tractor tube.

28 Claims, 23 Drawing Sheets

(51) Int. Cl.
*A61B 17/3205* (2006.01)
*A61B 17/00* (2006.01)
*A61B 17/34* (2006.01)

(56) References Cited

U.S. PATENT DOCUMENTS

| | | | |
|---|---|---|---|
| 4,324,262 | A | 4/1982 | Hall |
| 4,469,100 | A | 9/1984 | Hardwick |
| 4,604,094 | A | 8/1986 | Shook |
| 4,646,736 | A | 3/1987 | Auth |
| 4,863,440 | A | 9/1989 | Chin |
| 4,946,440 | A | 8/1990 | Hall |
| 5,364,345 | A | 11/1994 | Lowery et al. |
| 5,389,100 | A | 2/1995 | Bacich et al. |
| 5,662,703 | A | 9/1997 | Yurek et al. |
| 5,971,938 | A | 10/1999 | Hart et al. |
| 6,221,006 | B1 | 4/2001 | Dubrul et al. |
| 6,238,412 | B1 | 5/2001 | Dubrul et al. |
| 6,245,078 | B1 | 6/2001 | Ouchi |
| 6,258,115 | B1 | 7/2001 | Dubrul |
| 6,544,278 | B1 | 4/2003 | Vrba et al. |
| 6,569,181 | B1 | 5/2003 | Burns |
| 6,620,179 | B2 | 9/2003 | Brook et al. |
| 6,635,068 | B1 | 10/2003 | Dubrul et al. |
| 6,635,070 | B2 | 10/2003 | Leeflang et al. |
| 6,830,561 | B2 | 12/2004 | Jansen et al. |
| 6,846,029 | B1 | 1/2005 | Ragner et al. |
| 6,942,682 | B2 | 9/2005 | Vrba et al. |
| 7,621,870 | B2 | 11/2009 | Berrada et al. |
| 7,780,696 | B2 | 8/2010 | Daniel et al. |
| 8,057,496 | B2 | 11/2011 | Fischer, Jr. |
| 8,070,769 | B2 | 12/2011 | Broome |
| 8,092,486 | B2 | 1/2012 | Berrada et al. |
| 8,657,867 | B2 | 2/2014 | Dorn et al. |
| 8,721,714 | B2 | 5/2014 | Kelley |
| 8,784,442 | B2 | 7/2014 | Jones et al. |
| 8,795,305 | B2 | 8/2014 | Martin et al. |
| 8,956,384 | B2 | 2/2015 | Berrada et al. |
| 9,028,401 | B1 * | 5/2015 | Bacich ............... A61M 39/24 600/204 |
| 9,125,683 | B2 | 9/2015 | Farhangnia et al. |
| 9,126,016 | B2 | 9/2015 | Fulton |
| 9,155,552 | B2 | 10/2015 | Ulm, III |
| 9,173,668 | B2 | 11/2015 | Ulm, III |
| 9,186,487 | B2 | 11/2015 | Dubrul et al. |
| 9,358,037 | B2 | 1/2016 | Farhangnia et al. |
| 9,259,237 | B2 | 2/2016 | Quick et al. |
| 9,351,747 | B2 | 5/2016 | Kugler et al. |
| 9,463,035 | B1 | 10/2016 | Greenhalgh et al. |
| 9,717,514 | B2 | 8/2017 | Martin et al. |
| 9,848,975 | B2 | 12/2017 | Hauser |
| 9,849,014 | B2 | 12/2017 | Kusleika |
| 9,962,178 | B2 | 5/2018 | Greenhalgh et al. |
| 1,001,033 | A1 | 7/2018 | Greenhalgh et al. |
| 1,001,626 | A1 | 7/2018 | Hauser |
| 1,002,875 | A1 | 7/2018 | Wallace et al. |
| 1,013,038 | A1 | 11/2018 | Farhangnia et al. |
| 1,027,186 | A1 | 4/2019 | Greenhalgh et al. |
| 1,032,788 | A1 | 6/2019 | Yachia |
| 2002/0032455 | A1 | 3/2002 | Boock et al. |
| 2002/0173819 | A1 | 11/2002 | Leeflang et al. |
| 2003/0083693 | A1 | 5/2003 | Daniel et al. |
| 2003/0135258 | A1 | 7/2003 | Andreas et al. |
| 2003/0153873 | A1 | 8/2003 | Luther et al. |
| 2003/0176884 | A1 | 9/2003 | Berrada et al. |
| 2003/0208224 | A1 | 11/2003 | Broome |
| 2004/0098033 | A1 | 5/2004 | Leeflang et al. |
| 2005/0085826 | A1 | 4/2005 | Nair et al. |
| 2005/0085849 | A1 | 4/2005 | Sepetka et al. |
| 2005/0119668 | A1 | 6/2005 | Teague et al. |
| 2005/0177132 | A1 | 8/2005 | Lentz et al. |
| 2005/0187570 | A1 | 8/2005 | Nguyen et al. |
| 2005/0283166 | A1 | 12/2005 | Greenhalgh |
| 2005/0283186 | A1 | 12/2005 | Berrada et al. |
| 2006/0042786 | A1 | 3/2006 | West |
| 2006/0089533 | A1 | 4/2006 | Ziegler et al. |
| 2006/0173525 | A1 | 8/2006 | Behl et al. |
| 2006/0195137 | A1 | 8/2006 | Sepetka et al. |
| 2006/0200221 | A1 | 9/2006 | Malewicz |
| 2006/0293696 | A1 | 12/2006 | Fahey et al. |
| 2007/0112374 | A1 | 5/2007 | Paul, Jr. et al. |
| 2007/0149996 | A1 | 6/2007 | Coughlin |
| 2007/0213765 | A1 | 9/2007 | Adams et al. |
| 2010/0030256 | A1 | 2/2010 | Dubrul et al. |
| 2010/0042136 | A1 | 2/2010 | Berrada et al. |
| 2010/0087844 | A1 | 4/2010 | Fischer, Jr. |
| 2010/0137846 | A1 | 6/2010 | Desai et al. |
| 2010/0190156 | A1 | 7/2010 | Van Wordragen et al. |
| 2010/0249815 | A1 | 9/2010 | Jantzen et al. |
| 2011/0034987 | A1 | 2/2011 | Kennedy |
| 2011/0118817 | A1 | 5/2011 | Gunderson et al. |
| 2011/0160763 | A1 | 6/2011 | Ferrera et al. |
| 2011/0265681 | A1 | 11/2011 | Allen et al. |
| 2011/0288529 | A1 | 11/2011 | Fulton |
| 2011/0288572 | A1 | 11/2011 | Martin |
| 2012/0083824 | A1 | 4/2012 | Berrada et al. |
| 2012/0083868 | A1 | 4/2012 | Shrivastava |
| 2012/0271105 | A1 | 10/2012 | Nakamura et al. |
| 2013/0046332 | A1 | 2/2013 | Jones et al. |
| 2013/0096571 | A1 | 4/2013 | Massicotte et al. |
| 2013/0116721 | A1 | 5/2013 | Takagi et al. |
| 2013/0226196 | A1 | 8/2013 | Smith |
| 2013/0317589 | A1 | 11/2013 | Martin et al. |
| 2013/0345739 | A1 | 12/2013 | Brady et al. |
| 2014/0005712 | A1 | 1/2014 | Martin et al. |
| 2014/0046133 | A1 | 2/2014 | Nakamura et al. |
| 2014/0155980 | A1 | 6/2014 | Turjman |
| 2014/0257253 | A1 | 9/2014 | Jemison |
| 2014/0276403 | A1 * | 9/2014 | Follmer ............ A61B 17/22032 604/103.02 |
| 2014/0330286 | A1 | 11/2014 | Wallace |
| 2014/0336691 | A1 | 11/2014 | Jones et al. |
| 2014/0364896 | A1 | 12/2014 | Consigny |
| 2014/0371779 | A1 | 12/2014 | Vale et al. |
| 2015/0005781 | A1 | 1/2015 | Lund-Clausen et al. |
| 2015/0018859 | A1 | 1/2015 | Quick et al. |
| 2015/0018860 | A1 | 1/2015 | Quick et al. |
| 2015/0088190 | A1 | 3/2015 | Jensen |
| 2015/0164523 | A1 | 6/2015 | Brady et al. |
| 2015/0164666 | A1 | 6/2015 | Johnson et al. |
| 2015/0190155 | A1 | 7/2015 | Ulm, III |
| 2015/0190156 | A1 | 7/2015 | Ulm, III |
| 2015/0196380 | A1 | 7/2015 | Berrada et al. |
| 2016/0022293 | A1 | 1/2016 | Dubrul et al. |
| 2016/0074627 | A1 | 3/2016 | Cottone |
| 2016/0106448 | A1 | 4/2016 | Brady et al. |
| 2016/0106449 | A1 | 4/2016 | Brady et al. |
| 2016/0113663 | A1 | 4/2016 | Brady et al. |
| 2016/0113664 | A1 | 4/2016 | Brady et al. |
| 2016/0113665 | A1 | 4/2016 | Brady et al. |
| 2017/0086864 | A1 | 3/2017 | Greenhalgh et al. |
| 2017/0112513 | A1 | 4/2017 | Marchand et al. |
| 2017/0303939 | A1 | 10/2017 | Greenhalgh et al. |
| 2017/0303942 | A1 | 10/2017 | Greenhalgh et al. |
| 2017/0303947 | A1 | 10/2017 | Greenhalgh et al. |
| 2017/0303948 | A1 | 10/2017 | Wallace et al. |
| 2017/0348014 | A1 | 12/2017 | Wallace et al. |
| 2018/0042624 | A1 | 2/2018 | Greenhalgh et al. |
| 2018/0042626 | A1 | 2/2018 | Greenhalgh et al. |
| 2018/0070968 | A1 | 3/2018 | Wallace et al. |
| 2019/0117244 | A1 | 4/2019 | Wallace et al. |
| 2019/0133622 | A1 | 5/2019 | Wallace et al. |
| 2019/0133623 | A1 | 5/2019 | Wallace et al. |
| 2019/0133624 | A1 | 5/2019 | Wallace et al. |
| 2019/0133625 | A1 | 5/2019 | Wallace et al. |
| 2019/0133626 | A1 | 5/2019 | Wallace et al. |
| 2019/0133627 | A1 | 5/2019 | Wallace et al. |
| 2019/0336148 | A1 | 11/2019 | Greenhalgh et al. |

FOREIGN PATENT DOCUMENTS

| | | |
|---|---|---|
| GB | 2498349 | 7/2013 |
| WO | WO 00/32118 | 6/2000 |
| WO | WO 2009086482 | 7/2009 |

(56) References Cited

FOREIGN PATENT DOCUMENTS

| WO | WO 2012/009675 | 1/2012 |
|---|---|---|
| WO | WO 2012/049652 | 4/2012 |
| WO | WO 2012162437 | 11/2012 |
| WO | WO 2017/058280 | 4/2017 |
| WO | WO2017189535 | 11/2017 |
| WO | WO2017189550 | 11/2017 |
| WO | WO2017189591 | 11/2017 |
| WO | WO2017189615 | 11/2017 |
| WO | WO2017210487 | 12/2017 |
| WO | WO 2018049317 | 3/2018 |
| WO | WO 2019010318 | 1/2019 |
| WO | WO 2019094456 | 5/2019 |

OTHER PUBLICATIONS

Invitation to Pay Additional Fees for International Patent Appln. No. PCT/US2018/040937 dated Sep. 26, 2018.
Response to Non-Final Office Action for U.S. Appl. No. 15/291,015, filed Sep. 5, 2018.
International search report and written opinion dated Nov. 14, 2018 for PCT/US2018/040937, Applicant Stryker Corporation 16 pages.
Notice of Allowance dated Dec. 11, 2018 for U.S. Appl. No. 15/291,015.
Notice of Allowance dated Mar. 22, 2018 for U.S. Appl. No. 15/496,668.
Notice of Allowance dated Apr. 19, 2018 for U.S. Appl. No. 15/496,570.
Notice of Allowance dated Apr. 19, 2018 for U.S. Appl. No. 15/496,786.
Non-Final Office Action dated Sep. 5, 2018 for U.S. Appl. No. 15/291,015.
Extended European Search Report dated Aug. 22, 2018 for European patent appln No. 16852212.6.
Office action dated Jun. 5, 2019 for Chinese application No. 2019053101871820, including partial English language translation provided by the foreign associate.
Wikipedia; Embolectomy; retrieved from the internet: https://en.wikipedia.org/wiki/Embolectomy; 4 pgs.; retrieved/printed: Mar. 24, 2016.
O'Sullivan; Thrombolysis versus thrombectomy in acute deep vein thrombosis; Interventional Cardiology; 3(5); pp. 589-596; Oct. 2011.
Capture Vascular Systems; (company website); retrieved from the internet: http://www.capturevascular.com; 3 pgs.; retrieved/printed: Mar. 24, 2016.
Edwards Lifesciences; Fogarty® Occlusion Catheters (product brochure); retrieved from the internet: http://web.archive.org/web/20150228193218/http://www.edwards.com/products/vascular/atraumaticocclusion/pages/occlusioncatheter.aspx; © 2011; 2 pgs.; retrieved/printed: Mar. 24, 2011.
Boston Scientific; Fetch(TM) 2 Aspiration Catheter (product information); retrieved from the internet: http://www.bostonscientific.com/en-US/products/thrombectomy-systems/fetch2-aspiration-catheter.html; 5 pgs.; retrieved/printed: Mar. 24, 2016.
Penumbra, Inc.; Indigo® System (product information); retrieved from the internet: http://www.penumbrainc.com/peripherallpercutaneous-thromboembolectomy/indigo-system; 2 pgs.; retrieved/printed: Mar. 24, 2016.
Youtube; Merci Retrieval System X Series Animation; uploaded Mar. 16, 2009 (product information); retrieved from the internet: https://www.youtube.com/watch?v=MGX7deuFkhc; 3 pgs.; retrieved/printed: Mar. 24, 2016.
Covidien; Solitaire(TM) AS Neurovascular Remodeling Device (product information); retrieved from the internet: http://www.ev3.net/neuro/intl/remodeling-devices/solitaire-ab.htm; © 2015; 2 pgs.; retrieved/printed: Mar. 24, 2016.
Notice of Allowance for U.S. Appl. No. 15/043,996 dated Jun. 9, 2016.
Ex Parte Quayle office action dated Aug. 2, 2019 for U.S. Appl. No. 15/497,092.
Invitation to Pay Additional Fees for International Patent Appln. No. PCT/US2018/059607 dated Jan. 31, 2019.
Japanese Office action dated Mar. 19, 2019 for Japanese Application No. 2018-535810 (with English Language translation).
International Search Report and Written Opinion dated Mar. 28, 2019 for International Appln. No. PCT/US2018/059607.
Notice of Allowance dated Apr. 10, 2019 for U.S. Appl. No. 15/611,546.
Response to Extended European Search Report for EP Patent Appln. No. 16852212.6 dated Mar. 15, 2019.
European Patent Office Communication Rule 161(1) and 162 dated Feb. 5, 2019 for EP Patent Appln. No. 17729703.3.
European Patent Office Communication Rule 161(1) and 162 EPC for EP Patent Appln. No. 17737084.8 dated Dec. 18, 2018.
European Patent Office Communication Rule 161(1) and 162 for EP Patent Appln. No. 17722277.5 dated Dec. 13, 2018.
European Patent Office Communication Rule161(1) and 162 dated Dec. 13, 2018 for EP Patent Appln. No. 17722290.8.
European Patent Office Communication Rule 161(1) and 162 dated Dec. 13, 2018 for EP Patent Appln. No. 17721036.6.
Response to Extended European Search Report for EP Patent Appln. No. 18174891.4 dated May 28, 2019.
Restriction Requirement dated Jun. 28, 2019 for U.S. Appl. No. 15/700,685.
International Search Report and Written Opinion dated May 6, 2016 for PCT/US2016/017982.
Response to European Patent Office Communication Rule 161(1) and 162 EPC filed Jun. 11, 2019, for EP Patent Appln. No. 17737084.8.
Response to European Patent Office Communication Rule 161(1) and 162 filed Jun. 4, 2019 for EP Patent Appln. No. 17722277.5.
Response to European Patent Office Communication Rule161(1) and 162 filed Jun. 4, 2019 for EP Patent Appln. No. 17722290.8.
Response to European Patent Office Communication 161(1) and 162 filed Jun. 11, 2019 for EP Patent Appln. No. 17721036.6.
European Patent Office Communication Rule161(1) and 162 dated Apr. 23, 2019 for EP Patent Appln. No. 17772186.7.
Response to Non-Final Office Action filed Nov. 8, 2017 for U.S. Appl. No. 15/496,570.
Response to Non-Final Office Action filed Feb. 1, 2018 for U.S. Appl. No. 15/496,786.
Restriction Requirement dated Apr. 11, 2019 for U.S. Appl. No. 15/497,092.
Response to Restriction Requirement filed Jun. 11, 2019 for U.S. Appl. No. 15/497,092.
Ex Parte Quayle office action dated Jul. 16, 2019 for U.S. Appl. No. 15/497,092.
Response to Rule 161(1) and 162 EPC filed on Jul. 23, 2019 for EP application No. 17729703.3.
PCT International Search Report and Written Opinion for International Patent Appln. No. PCT/US2019/032601, Applicant Stryker Corporation, dated Jul. 23, 2019 (12 pages).
Response to Ex Parte Quayle office action filed Jul. 23, 2019 for U.S. Appl. No. 15/497,092.
Non-Final Office Action for U.S. Appl. No. 15/496,570, dated Aug. 9, 2017.
PCT International Search Report and Written Opinion for International Appln. No. PCT/US2017/029440, Applicant Stryker Corporation, dated Jul. 7, 2017.
PCT Invitation to Pay Additional Fees for International Appln. No. PCT/US2017/029366, Applicant Stryker Corporation, dated Jul. 7, 2017.
PCT International Search Report and Written Opinion for International Appln. No. PCT/US2017/029472, Applicant Stryker Corporation, dated Jul. 7, 2017.
PCT International Search Report and Written Opinion for International Appln. No. PCT/US2017/035543, Applicant Stryker Corporation, dated Aug. 14, 2017.
PCT International Search Report and Written Opinion for International Appln. No. PCT/US2017/029366, Applicant Stryker Corporation, dated Aug. 29, 2017.

(56) References Cited

OTHER PUBLICATIONS

PCT Invitation to Pay Additional Fees for International Appln. No. PCT/US2017/029345, Applicant Stryker Corporation, dated Oct. 17, 2017.
Non-Final Office Action for U.S. Appl. No. 15/496,786, dated Nov. 1, 2017.
PCT International Search Report and Written Opinion for International Appln. No. PCT/US2017/050933, Applicant Stryker Corporation, forms PCT/ISA/210, 220, and 237, dated Nov. 10, 2017 (16 pages).
Response to Non-Final Office Action for U.S. Appl. No. 14/496,786, filed Feb. 1, 2018.
Non-final office action dated Feb. 1, 2018 for U.S. Appl. No. 15/496,668.
Response to Restriction for U.S. Appl. No. 15/496,668, filed Feb. 21, 2018.
International search report and written opinion dated Feb. 28, 2018 for PCT/US2017/029345, Applicant Stryker Corporation 26 pages.
Non Final Office Action dated Sep. 3, 2019 for U.S. Appl. No. 15/794,939.
Rule 71(3) Allowance for EP Patent Appln. No. 18174891.4 dated Jul. 30, 2019.
Response to Ex Parte Quayle office action filed Sep. 17, 2019 for U.S. Appl. No. 15/497,092.
Office action response filed on Sep. 26, 2019 for Chinese Patent Application No. 2016800567527, no translation received.
Non-Final Office Action dated Oct. 4, 2019 for U.S. Appl. No. 15/795,097.
Response to Restriction filed Oct. 4, 2019 for U.S. Appl. No. 15/795,097.
Notice of Allowance dated Sep. 27, 2019 for U.S. Appl. No. 15/497,092.
Extended European Search Report dated Oct. 8, 2019 for European Patent Application No. 19191925.7.
Office action dated Oct. 7, 2019 for European Patent Application No. 17729703.3.
Office action dated Oct. 7, 2019 for European Patent Application No. 17737084.8.
Response to European Patent Office Communication Rule161(1) and 162 filed Oct. 17, 2019 for EP Patent Appln. No. 17772186.7.
Invitation to Pay Additional Fees for International Patent Appln. No. PCT/US2019/050467 dated Oct. 25, 2019.
International Search Report and Written Opinion for International Patent Appln. No. PCT/US2019/050410 dated Oct. 25, 2019.
Notice of Allowance dated Oct. 24, 2019 for U.S. Appl. No. 15/611,546.
Notice of Allowance dated Nov. 6, 2019 for U.S. Appl. No. 15/795,097.
Rule 71(3) Allowance for EP Patent Appln. No. 17721036.6 dated Oct. 23, 2019.
Rule 71(3) Allowance for EP Patent Appln. No. 17722290.8 dated Nov. 11, 2019.
Amendment Response submitted dated Dec. 3, 2019 for U.S. Appl. No. 15/794,939.

* cited by examiner

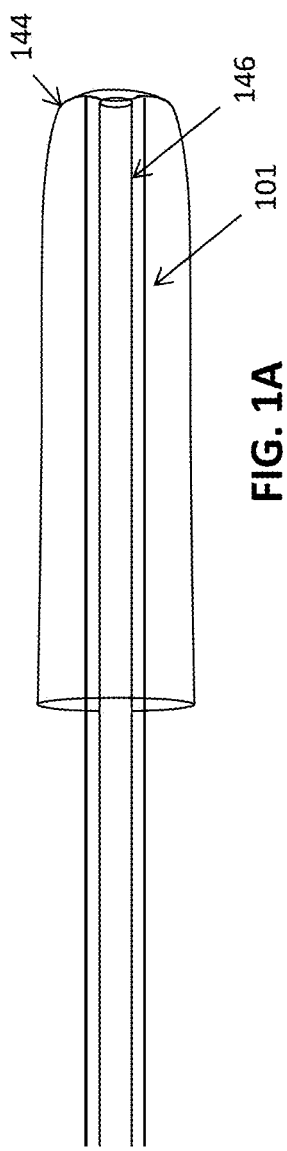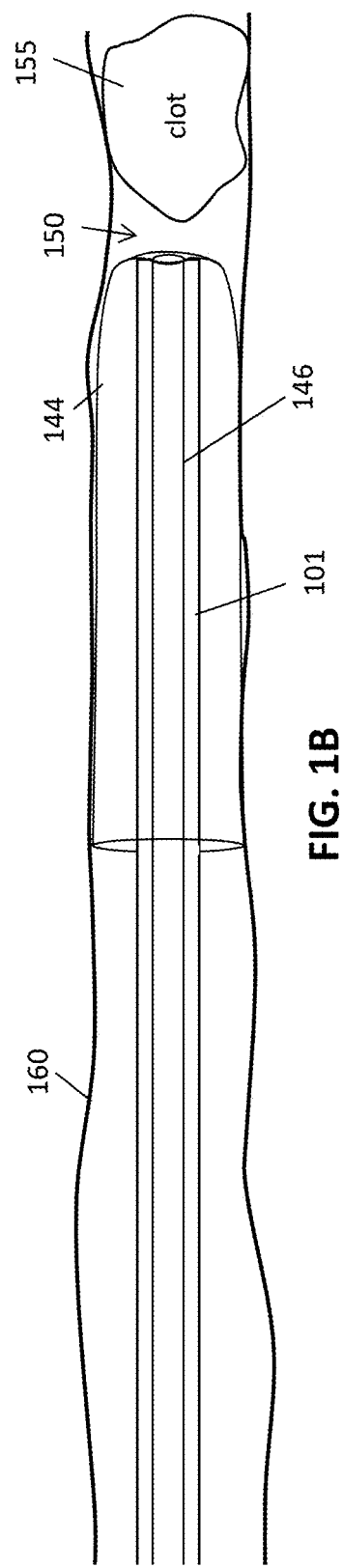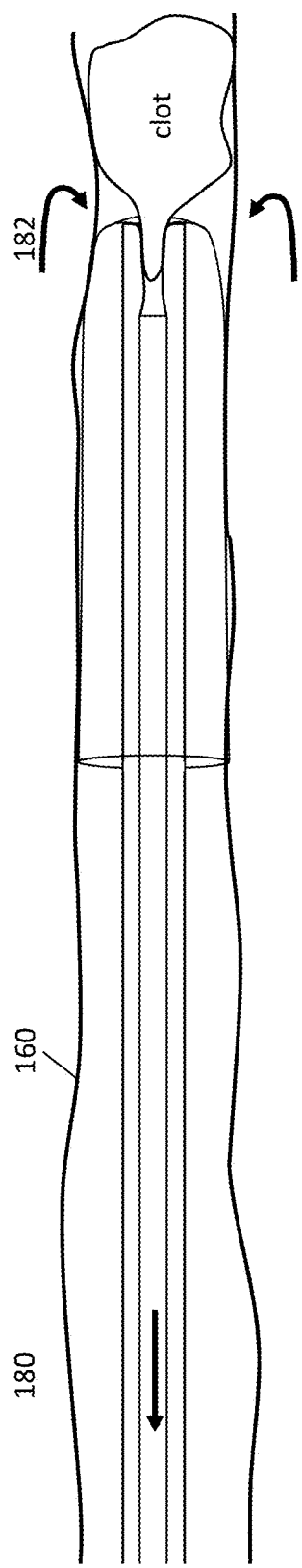

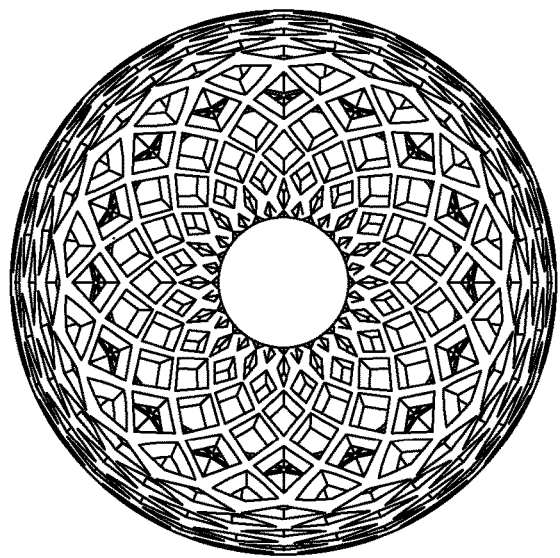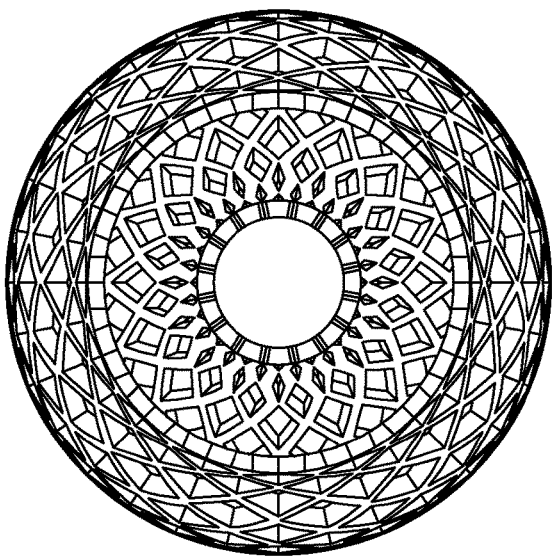
FIG. 27A  FIG. 27B
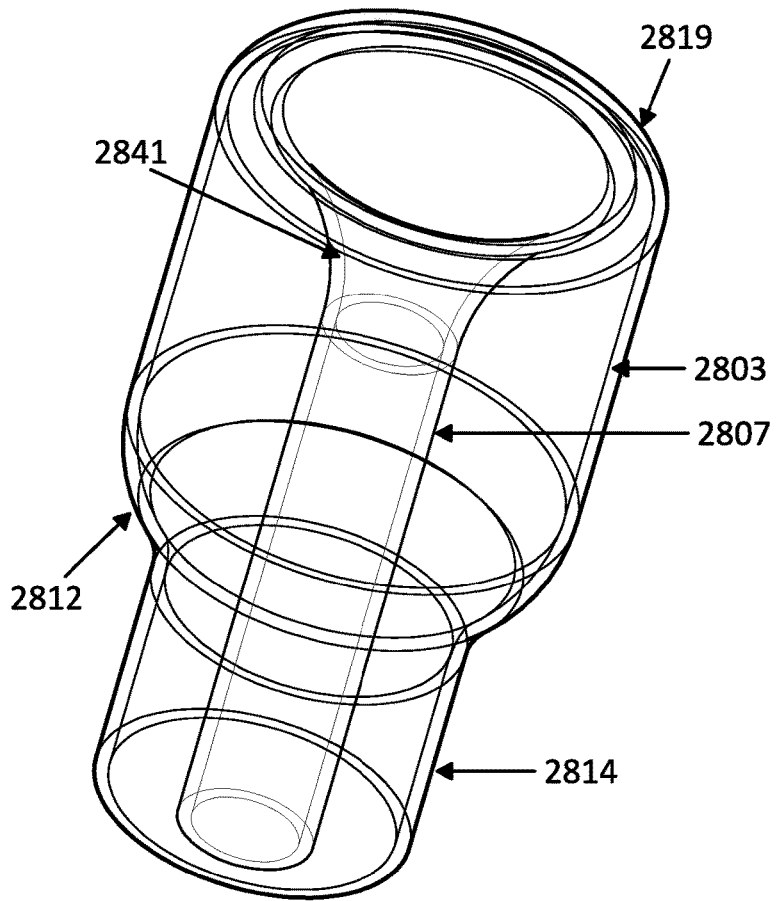
FIG. 28

SELF-ROLLING THROMBECTOMY APPARATUSES AND METHODS

CROSS REFERENCE TO RELATED APPLICATIONS

This patent application claims the benefit of priority to U.S. Provisional Patent Application No. 62/393,460, filed Sep. 12, 2016.

The subject matter of this patent application is related to the subject matter disclosed and described in each of U.S. patent application Ser. No. 15/291,015, filed Oct. 11, 2016; U.S. patent application Ser. No. 15/043,996, filed Feb. 15, 2016, now U.S. Pat. No. 9,463,035, U.S. patent application Ser. No. 15/496,570, filed Apr. 25, 2017; U.S. patent application Ser. No. 15/496,668, filed Apr. 25, 2017; U.S. patent application Ser. No. 15/496,786, filed Apr. 25, 2017; U.S. patent application Ser. No. 15/497,092, filed Apr. 25, 2017; and U.S. patent application Ser. No. 15/611,546, filed Jun. 1, 2017. Each of the foregoing patents and patent applications is incorporated by reference herein in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The apparatuses and methods described herein relate to mechanical removal of objects from within a body. In particular, described herein are mechanical thrombectomy apparatuses and methods.

BACKGROUND

It is often desirable to remove tissue from the body in as minimally invasive a manner as possible, so as not to damage other tissues. For example, removal of tissue from within a patient's vasculature, such as removal of blood clots from veins and arteries, may improve patient conditions and quality of life.

Many vascular problems stem from insufficient blood flow through blood vessels. One cause of insufficient or irregular blood flow is a blockage within a blood vessel referred to as a blood clot, or thrombus. Thrombi can occur for many reasons, including after a trauma such as surgery. For example, a large percentage of the more than 1.2 million heart attacks in the United States are caused by blood clots (thrombi) which form within a coronary artery.

When a thrombus forms, it may effectively stop the flow of blood through the zone of formation. If the thrombus extends across the interior diameter of an artery, it may cut off the flow of blood through the artery. If a coronary artery is 100% thrombosed, the flow of blood is stopped in that artery, resulting in a shortage of oxygen carrying red blood cells, e.g., to supply the muscle (myocardium) of the heart wall. Such a thrombosis can be triggered within an artery by damage to the arterial wall from atherosclerotic disease. Thus, the underlying disease of atherosclerosis may not cause acute oxygen deficiency (ischemia) but can trigger acute ischemia via induced thrombosis. Similarly, thrombosis of one of the carotid arteries can lead to stroke because of insufficient oxygen supply to the brain. Oxygen deficiency reduces or prohibits muscular activity, can cause chest pain (angina pectoris), and can lead to death of myocardium which permanently disables the heart. If myocardial cell death is extensive, the heart will be unable to pump sufficient blood to supply the body's needs.

Clinical data indicates that clot removal may be beneficial or even necessary to improve outcomes in such cases. For example, in the peripheral vasculature, inventions and procedures can reduce the need for an amputation by 80 percent. The ultimate goal of any modality to treat these conditions of the arterial or venous system is to remove the blockage or restore patency, quickly, safely, and cost effectively. This may be achieved by thrombus dissolution, fragmentation, thrombus aspiration or a combination of these methods.

Mechanical thrombectomy devices may be particularly advantageous. Depending on the size, location and extent of a clot, it may also be particularly advantageous to mechanical retrieve and break apart the clot in a manner that is both safe and effective. There is a definite need for a thrombectomy device, and particularly a mechanical thrombectomy device that can be more effective in removing tissue such as clots from within a body. Described herein are systems and apparatuses, and methods of using such systems and apparatuses, that address the needs and problems discussed above.

SUMMARY OF THE DISCLOSURE

Described herein are mechanical thrombectomy apparatuses (devices, systems, etc.) and methods of using and making them.

In general, described herein are self-rolling mechanical atherectomy apparatuses for removing a clot from a vessel. These atherectomy apparatuses, which may also be referred to as thrombectomy apparatuses, typically include a tractor tube portion that rolls and inverts over itself in a continuous motion, tractor-like, to draw material into the tractor tube. The apparatuses described herein may be similar to the mechanical atherectomy apparatuses, systems and methods disclosed and described in the above-list of related U.S. patents and applications, which have been incorporated by reference herein in their entirety. However, the self-rolling mechanical atherectomy apparatuses described herein are configured such that the tractor tube (also referred to as a tractor region) rolls and inverts over itself unsupported at the distal-facing end when the inner tractor tube portion is pulled proximally. Specifically, the apparatuses described herein are configured so that the tractor tube rolls and inverts over itself, unsupported, without the need for an internal catheter extending within the inverting tractor tube providing a support or distal end opening to roll over.

Thus, the tractor tube is inverted over itself to form a distal-facing region at the distal end of the self-rolling mechanical atherectomy apparatus where, in a deployed configuration, the outer tractor tube portion rolls over and into itself, unsupported to become the inner tractor tube portion as the proximal end of the inner tractor tube portion is pulled proximally. At least the distal-most region of the tractor tube (e.g., the region at or near the distal-facing, inverting region of the tractor tube) is unsupported over at least the distal-most 1 or more cm of the apparatus. The tractor tube may be actuated to roll over itself by pulling proximally on the inner tractor tube portion (or an inner tractor puller coupled to the inner tractor tube portion) and/or by pushing distally on a proximal end of the outer tractor tube portion that is braced against an outer tractor pusher. In general, in an expanded configuration, the proximal end of the outer tractor tube portion is braced against a tapered portion of the tractor tube proximal to the outer tractor tube portion.

The tractor tube may be adapted to allow unsupported rolling over itself having a column strength of the outer tractor tube portion that resists buckling and/or collapse when compressed by pulling proximally on the inner tractor tube portion. As described in greater detail herein, this may be accomplished by one or more of forming the tractor tube from a braided material having a compressed braid angle relative to the proximal-to-distal axis that is greater than 80 degrees (e.g., greater than 85 degrees, greater than 90 degrees, greater than 95 degrees, greater than 100 degrees, between 80-170 degrees, between 90-170 degrees, between 95-170 degrees, etc.); the braid angle of the inner tractor tube portion under tension in the proximal-to-distal axis is typically much less than the compressed braid angle of the outer tractor tube portion in compression, and may be, e.g., less than 90 degrees (e.g., less than 85 degrees, less than 80 degrees, less than 75 degrees, less than 70 degrees, less than 65 degrees, less than 60 degrees, less than 50 degrees, less than 45 degrees, less than 40 degrees, between 90-5 degrees, between 80-5 degrees, between 70-5 degrees, between 65-5 degrees, between 60-5 degrees, etc.). The compressed outer tractor tube braid angle refers to the braid angle of the outer tractor tube in the deployed (e.g., radially expanded) configuration; pulling the inner tractor tube portion proximally, e.g., by pulling the inner tractor puller, results in a compressive load on the outer tractor tube portion that is continuous but inverted relative to the inner tractor tube portion.

For example, described herein are self-rolling mechanical atherectomy apparatuses that include: an outer tractor pusher comprising a catheter having a distal end and a distal end opening; a tractor tube comprising an outer tractor tube portion that extends distally in an un-inverted configuration and inverts into itself at a distal-facing region to form an inner tractor tube portion, wherein the tractor tube is configured so that pulling the inner tractor tube portion proximally compresses the outer tractor tube portion so that it has a column strength that resists collapsing, further wherein pulling the inner tractor tube proximally causes a region of the outer tractor tube portion at the distal-facing region to roll over itself, unsupported, and invert into the inner tractor tube portion; and an inner tractor puller coupled to the inner tractor tube portion and extending proximally within the outer tractor pusher.

In general, the outer tractor pusher may be a catheter, tube, cannula, or the like. During delivery or positioning of the apparatus, the tractor tube, and an inner tractor puller, if included, may be held within the outer tractor pusher in an un-deployed configuration. Prior to clot removal, the tractor tube may be deployed out of the outer tractor pusher portion and the outer tractor pusher portion maybe expanded into a deployed configuration that has an outer radial diameter that is greater than the inner radial diameter of the outer tractor pusher. The outer tractor pusher may then be positioned to support or brace the outer tractor tube portion to allow it to roll over and into itself distally when the inner tractor puller is pulled proximally. Alternatively, a separate distal access catheter may be included, and the outer tractor pusher may be held within the distal access catheter along with the tractor tube prior to deployment within the blood vessel.

In any of these apparatuses, the outer tractor pusher may be coupled to a proximal end of the outer tractor tube portion of the tractor tube. Alternatively, the proximal end of the outer tractor tube portion may be unconnected to the outer tractor pusher.

As mentioned, the apparatus may include a distal access catheter. The outer tractor pusher, the tractor tube and inner tractor puller may be held within the distal access catheter in an un-deployed configuration, further wherein the tractor tube may be configured to be pushed distally out of the distal access catheter so that the outer tractor tube portion may expand to a diameter that is greater than an outer diameter of the distal access catheter in a deployed configuration. Alternatively, the outer tractor pusher may be configured as a distal access catheter wherein the tractor tube and inner tractor puller may be held within the outer tractor pusher in an un-deployed configuration, further wherein the tractor tube may be configured to be deployed by being pushed distally out of the outer tractor pusher so that the outer tractor tube portion expands to an outer diameter that is greater than an outer diameter of the outer tractor pusher.

In any of the self-rolling mechanical atherectomy apparatuses described herein, the tractor tube may be configured so that pulling the inner tractor tube proximally compresses the outer tractor tube portion and the column strength of the outer tractor tube portion resists collapsing up to at least 300 g of compression (e.g., at least about 350 g of compression, at least about 400 g of compression, at least about 450 g of compression, at least about 500 g of compression, at least about 550 g of compression, at least about 600 g of compression, at least about 650 g of compression, at least about 700 g of compression, etc.).

In general, the tractor tube comprises a braided or woven material. For example, the tractor tube may be a woven or braided tube, e.g., formed of one or a plurality of filament. The filaments may be monofilaments or bundles of filaments, and may be a polymeric material, a metal material, a natural fiber material, etc. For example, the tractor tube may be formed of between 24-48 filaments. The tractor tube may be formed of a plurality of filaments having a diameter of greater than about 0.003 inches (e.g., greater than 0.0020 inches, greater than 0.0025 inches, greater than 0.0035 inches, greater than 0.0040 inches, greater than 0.0045 inches, greater than 0.0050 inches, etc.).

In particular, the tractor tube may be configured to resist buckling when rolling over itself based in part on the arrangement of the filaments. For example, the outer tractor tube portion may have a braid angle in a proximal to distal axis (in a compressed configuration) that is between 80 and 170 degrees, and the inner tractor tube portion may have a braid angle in the proximal to distal axis (e.g., under tension) of less than 80 degrees.

In any of the apparatuses described herein, the proximal end of the outer tractor tube portion may be configured to have a tapered shape when the outer tractor tube portion is expanded radially outward. This tapered region may be shape set into the tractor tube (e.g., when the tractor tube is formed of a shape-settable material, for example, such as a nickel titanium alloy) and/or it may be formed by attaching a retaining structure to the proximal end of the outer tractor tube portion, such as a retaining band, retaining ring, etc., or by attachment to the outer tractor pusher.

As mentioned, the distal-facing region of the tractor tube may be unsupported, including unsupported over at least 1 cm proximally from the distal-facing region of the tractor tube (e.g., at least 1.5 cm, at least 2 cm, at least 2.5 cm, etc.). Thus, the tractor tube does not roll over a support (such as a catheter) at the distal-facing tractor portion at the distal end of the device.

In general, the tractor tube may be porous. For example, the tractor tube may have a porosity of 50% or greater (e.g., 55% or greater, 60% or greater, 65% or greater, 70% or greater, 75% or greater, etc.).

Any of the apparatuses described herein may be used with a guidewire, for placing the apparatus. For example, the inner tractor puller may include an inner lumen configured to pass a guidewire out of a distal end of the apparatus. In general a guidewire may be included as part of the apparatus.

Any of these apparatuses may include a vacuum source coupled to the tractor tube and configured to apply a vacuum (e.g., aspiration) therethrough. The vacuum source may include a pump.

For example, a self-rolling mechanical atherectomy apparatus for removing a clot from a vessel may include: an outer tractor pusher comprising a catheter having a distal end and a distal end opening; a tractor tube comprising an outer tractor tube portion that extends distally in an un-inverted configuration and inverts into itself at a distal-facing region to form an inner tractor tube portion, wherein the tractor tube is configured so that pulling the inner tractor tube portion proximally compresses the outer tractor tube portion so that it has a column strength that resists collapsing up to at least 500 g of compression and extends the inner tractor tube portion, further wherein pulling the inner tractor tube proximally causes a region of the outer tractor tube portion at the distal-facing region to roll over itself, unsupported, and invert into the inner tractor tube portion; and an inner tractor puller coupled to the inner tractor tube portion and extending proximally within the outer tractor pusher.

Also described herein are methods of removing a clot from a blood vessel using any of the apparatuses described herein. Generally, these methods may include actuating a self-rolling mechanical atherectomy apparatus so that the distal-facing region of the tractor tube is unsupported as the outer tractor tube portion rolls over and into itself and inverts, pulling in any clot or other target material into the tractor tube. The tractor tube is typically configured to roll over itself without support (e.g., be "self-rolling") from any other structure, e.g., by having a sufficient column strength in the outer tractor tube portion in compression to resist or prevent buckling, bending or collapse, yet be sufficiently flexible that it may bend and navigate through the often tortious anatomy of the vasculature (and particularly the neurovasculature), and to roll over itself. Various configurations are described herein to achieve this combination of flexibility and column strength, including forming the apparatus with a braided (or woven) tractor tube having a large braid angle in the outer tractor tube portion (under compression) and a relatively smaller braid angle in the inner tractor tube portion (e.g., under tension).

For example, a method of removing a clot from a blood vessel may include: advancing a distal end of a self-rolling mechanical atherectomy apparatus through the blood vessel to the clot, wherein the self-rolling mechanical atherectomy apparatus comprises a tractor tube, an outer tractor pusher, and an inner tractor puller; pulling an inner tractor puller of the tractor tube proximally to compresses an outer tractor tube portion of the tractor tube, wherein pulling the inner tractor puller proximally causes the outer tractor tube portion at a distal-facing region of the tractor tube to roll over itself, unsupported, and invert into the inner tractor tube portion; and engaging the clot with the tractor tube as it rolls over itself so that the clot is pulled into the tractor tube.

Any of these methods may include deploying the tractor tube of the self-rolling mechanical atherectomy apparatus so that the outer tractor tube portion of the tractor tube expands to have an outer diameter that is greater than an outer diameter of the outer tractor pusher. Pulling the inner tractor puller may include bracing a distal-facing end of the outer tractor pusher against a tapered face of the tractor tube that is proximal to the outer tractor tube portion. Thus, the tapered face or region of the tractor tube may be pushed against the outer tractor pusher when the tractor tube is attached or un-attached to the outer tractor pusher. When attached to the outer tractor pusher, the tapered face region of the tractor tube may still be driven against the opening of the outer tractor pusher.

Any of the methods described herein may include advancing a guidewire within the blood vessel to the clot, wherein advancing the self-rolling mechanical atherectomy apparatus comprises advancing the self-rolling mechanical atherectomy apparatus over the guidewire through the blood vessel until the self-rolling mechanical atherectomy apparatus is proximate to the clot.

Engaging (or "grabbing") the clot may include advancing the outer tractor pusher distally while pulling the inner tractor puller proximally. Alternatively or additionally, engaging the clot may include advancing the outer tractor pusher distally at a first rate while pulling the inner tractor puller proximally at a second rate that is different (e.g., faster) than the first rate.

In general, advancing may include advancing the self-rolling mechanical atherectomy apparatus distally with the tractor tube and inner tractor puller within the outer tractor pusher, wherein the tractor tube is in an un-deployed configuration. Once near (e.g., adjacent) the clot or other target, the tractor tube may be deployed from the inner tractor puller and/or distal access catheter.

Any of these methods may include applying aspiration through the tractor tube.

Advancing the self-rolling mechanical atherectomy apparatus may include advancing a distal access catheter enclosing the tractor tube, outer tractor pusher and inner tractor puller, wherein the outer tractor tube portion is inverted over the inner tractor puller in an un-deployed configuration within the distal access catheter.

Pulling the inner tractor puller may include applying up to 500 g of compressive force on the outer tractor tube portion without collapsing the outer tractor tube portion.

For example, a method of removing a clot from a blood vessel may include: advancing a distal end of a self-rolling mechanical atherectomy apparatus through the blood vessel to the clot, wherein the self-rolling mechanical atherectomy apparatus comprises a tractor tube, an outer tractor pusher, and an inner tractor puller; deploying the tractor tube of the self-rolling mechanical atherectomy apparatus so that an outer tractor tube portion of the tractor tube expands to have an outer diameter that is greater than an outer diameter of the outer tractor pusher, wherein a distal-facing end of the outer is braced against a tapered face of the tractor tube proximal to the outer tractor tube portion, and wherein the outer tractor tube portion inverts over itself at a distal-facing region of the tractor tube and extends proximally within the outer tractor tube portion as an inner tractor tube portion that is coupled to the inner tractor puller; pulling the inner tractor puller proximally to compresses the outer tractor tube portion of the tractor tube, and to cause the outer tractor tube portion of the tractor tube to roll over itself, unsupported, at the distal-facing region and to invert into the inner tractor tube portion; engaging the clot with the tractor tube as it rolls over itself so that the clot is pulled into the tractor tube; and withdrawing the self-rolling mechanical atherectomy holding the clot from the blood vessel.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1C illustrate an example of an apparatus for mechanically removing an object such as a clot form a body region that include an inverted tube (e.g., "tractor" tube) of material that rolls and inverts over the distal end of an inner catheter. FIG. 1A shows the device, including the tractor tube portion connected to a puller that is within the catheter. The tractor tube may be deployed in a vessel near a clot, as shown in FIG. 1B. To activate this type of mechanical thrombectomy device the end of the tractor tube in the catheter, which is shown connected to a puller also within the catheter, is pulled proximally away from the clot, rolling the tractor tube over the distal end of the catheter and inverting it, as shown in FIG. 1C. The clot may then be drawn into the catheter by the rolling and inverting action of the tractor tube.

In FIG. 2A, the apparatus includes an outer tractor pusher (e.g., catheter, cannula, tube, etc.), a tractor tube that is inverted over itself at a distal-facing portion of the apparatus, and an inner tractor puller (e.g., rod, catheter, cannula, tube, etc.) connected to an inner tractor tube portion of the tractor tube that is inverted relative to the outer tractor tube portion and extends inside of the outer tractor tube portion.

In FIG. 3A, the tractor tube is formed of as a woven structure that is configured to compress with a large braid angle under tension, e.g., when pushing the outer tractor tube portion distally and/or pulling the inner tractor tube portion proximally, and is further configured to have a small braid angle in the inner tractor tube portion. Thus, the tractor tube supports itself so that it may roll over itself and invert at a distal-facing region when either the inner tractor tube portion of the tractor tube is pulled proximally (and the outer tractor tube portion of the tractor tube is held in position or pushed distally), or when the outer tractor tube portion of the tractor tube is pushed distally (and when the inner tractor tube portion is pulled proximally or held in position). The tractor tube rolls over itself at the distal-facing region of the tractor tube and this rolling action may draw material into the inner tractor tube portion. FIG. 3B is similar to FIG. 3A, except that one end of the tractor tube (the region adjacent to the outer tractor tube portion) is constrained within the outer tractor pusher, and the outer tractor pusher pushes or braces against the tapered surface between the constrained region and the outer tractor tube portion.

In FIG. 4A, the self-rolling mechanical atherectomy apparatus has a tractor tube is inverted over itself at a distal-facing region, and includes an inner tractor rube portion that is connected to an inner tractor puller. The inner tractor puller shown may be a rod, catheter, or cannula (e.g., hypotube). In this example, the end of the outer tractor tube portion of the tractor tube is connected to an outer tractor pusher (catheter). FIG. 4B illustrates the self-rolling mechanical atherectomy apparatus being actuated to roll and invert the tractor tube over itself, unsupported, at its distal-facing region. In FIG. 4B, the outer tractor tube region has sufficient column strength to prevent buckling, or collapse of the tractor tube under the applied tension. The apparatus is actuated in FIG. 4B by pushing the outer tractor pusher distally (to the right) while holding the inner tractor puller fixed relative to the patient's body (e.g., the vessel). FIG. 4C shows actuation of the self-rolling mechanical atherectomy apparatus of FIG. 4A so that the tractor tube rolls and inverts from the outer tractor tube portion to the inner tractor tube portion at the distal-facing region by holding the outer tractor pusher and pulling proximally on the inner tractor puller. FIG. 4D illustrates actuation of the self-rolling mechanical atherectomy apparatus of FIG. 4A by both pulling the inner tractor tube portion proximally (e.g., by pulling the inner tractor puller proximally) and by pushing the outer tractor tube portion distally (e.g., by pushing the outer tractor pusher distally).

In FIG. 5A, the apparatus includes an outer catheter (e.g., distal access catheter), a tractor tube having an outer tractor tube portion that inverts at a distal-facing region into an inner tractor tube portion, an inner tractor puller connected at the proximal end of the inner tractor tube portion of the tractor tube, and an outer tractor pusher connected at the proximal end of the outer tractor tube portion of the tractor tube. The apparatus is in a vessel and is maneuvered so that the distal-facing end region of the tractor tube is adjacent to the clot. Once positioned, the outer catheter may be withdrawn, and tension may be applied (e.g., by pushing distally on the outer tractor pusher), expanding the tractor tube within the vessel, as shown in FIG. 5B. The tractor tube may be positioned at or against the clot. Thereafter, the tractor tube may be rolled on itself, unsupported by any internal catheter at the distal-facing end region, as shown in FIG. 5C, by pulling the inner tractor puller proximally and/or pushing the outer tractor pusher distally, drawing the clot into the inner tractor tube portion. This process may be continued until the entire clot is pulled into the inner tractor tube portion, as shown in FIG. 5D. Thereafter the tractor tube, outer tractor pusher and inner tractor puller may be withdrawn back into the distal access catheter and withdrawn from the vessel.

In FIG. 6A, the apparatus includes a tractor tube having an outer tractor tube portion, distal-facing region where the outer tractor tube portion inverts into an inner tractor tube portion, and an inner tractor puller that is connected to the inner tractor tube portion. The tractor tube and the inner tractor puller are held within a distal access catheter, and the outer tractor tube portion is unattached. The self-rolling mechanical atherectomy apparatus is positioned within a vessel near a clot. In FIG. 6B the outer distal access catheter is withdrawn proximally and/or the inner tractor puller is advanced distally, so that the tractor tube is partially extended from the distal end of the outer distal access catheter and adjacent to the clot. The outer tractor tube portion is placed under tension, e.g., by pulling the inner tractor puller proximally, as shown in FIG. 6B, expanding the outer tractor tube portion so that it is jammed against the distal opening of the outer distal access catheter. As the inner tractor puller is pulled proximally, the tractor tube rolls and inverts at the distal-facing region, drawing the inner tractor tube portion proximally and engaging the clot, as shown in FIG. 6C. The inner tractor tube portion is withdrawn proximally by pulling the inner tractor puller until the clot is engulfed, as shown in FIG. 6D. The self-rolling mechanical atherectomy apparatus, holding the clot, may then be withdrawn.

In FIG. 7A, the tractor tube (e.g., the outer tractor tube portion) is shown collapsed when applying tension by pulling the inner tractor puller proximally. In FIG. 7B, the tractor tube (e.g., the outer tractor tube portion) is shown collapsed when applying tension by pushing the outer tractor pusher (e.g., an outer catheter) distally. The configuration of the tractor tube may be configured to avoid this failure mode, including adjusting the braid angle of the outer and/or inner tractor tube portions, the amount of expansion of the tractor in the outer tractor tube portion, the number of strands (or strand equivalents) forming the tractor tube, the minimum length of expanded tractor tube, the material used for the tractor tube, the thickness of the strands or strand equivalents of the tractor tube, the porosity of mesh forming the tractor tube, or combinations of these.

FIG. 8A shows an example of a self-rolling mechanical atherectomy apparatus. FIG. 8B show the apparatus of FIG. 8A when the outer tractor tube portion is placed under tension by advancing the outer catheter (e.g., outer tractor pusher) relative to the inner tractor puller, collapsing the proximal end of the outer tractor pusher portion FIG. 9 schematically illustrates a self-rolling mechanical atherectomy apparatus showing examples of internal and external braid angles for the outer tractor tube portion and the inner tractor tube portion, respectively.

In FIG. 14A the self-rolling mechanical atherectomy apparatus, which is held within a distal access catheter, is positioned adjacent to a clot within a blood vessel. Once positioned, distal access catheter is withdrawn, allowing the outer tractor tube portion of the tractor tube to expand, as shown in FIG. 14B. The proximal end of the outer tractor tube portion is tapered, as shown, and may present a face that the distal access catheter, acting as an outer tractor pusher, may push against, as shown in FIG. 14C. The proximal end may be shape-set into this tapered shape, or it may be formed in this shape. Thereafter, the proximal end of the inner tractor tube portion may be pulled proximally to roll the outer tractor tube portion over itself (unsupported) so that it inverts into the inner tractor tube portion, capturing and drawing the clot with it, as shown in FIG. 14D. The inner tractor tube may be pulled fully back into the outer tractor pusher (in this example, the distal access catheter) and withdrawn from the body.

FIG. 16B illustrates the use of the self-rolling mechanical atherectomy apparatus of FIG. 16A to grab and withdraw a clot from a vessel by pulling the inner tractor tube portion of the tractor tube proximally, so that the outer tractor tube portion rolls over itself, unsupported, at the distal-facing region of the tractor tube, and inverts to become more inner tractor tube portion. FIG. 16C illustrates the fully withdrawing the tractor tube into the outer tractor pusher, releasing the end of the tractor tube that is attached to the outer tractor pusher and allowing the entire (now inverted) tractor tube to be withdrawn into the apparatus.

FIG. 20B is an enlarged view of the pattern of FIG. 20A.

FIG. 21B is an enlarged view of the pattern of FIG. 21A.

FIG. 22B is an enlarged view of the pattern of FIG. 22A.

FIG. 23B is an enlarged view of the pattern of FIG. 23A.

FIG. 24B is an enlarged view of the pattern of FIG. 24A.

FIG. 26B shows a side perspective view, while FIG. 26C shows a sectional view though the self-rolling mechanical atherectomy apparatus of FIG. 26B during operation of the apparatus.

FIG. 27A shows a top view looking proximally on the distal-facing region of the tractor puller of FIGS. 26A-26C, showing the change in the braid angle from the high column strength (large braid angle) outer tractor tube portion in compression, to the elongated (small braid angle) inner tractor tube portion in extension, when pulling the inner tractor tube portion proximally.

FIG. 27B shows a bottom view looking distally from the constrained region at the proximal end of the outer tractor tube portion, showing the inside of the distal-facing region of the tractor tube.

FIG. 28 illustrates a shape outline of a tractor tube of a self-rolling mechanical atherectomy apparatus, showing a funnel shape that may be formed as the tractor tube is rolled over itself, unsupported, at the distal-facing region. The tractor tube may be configured to form this funnel shape; the tractor tube may be a braided, woven, knit, solid, or some combination of these.

DETAILED DESCRIPTION

Figure 2A:
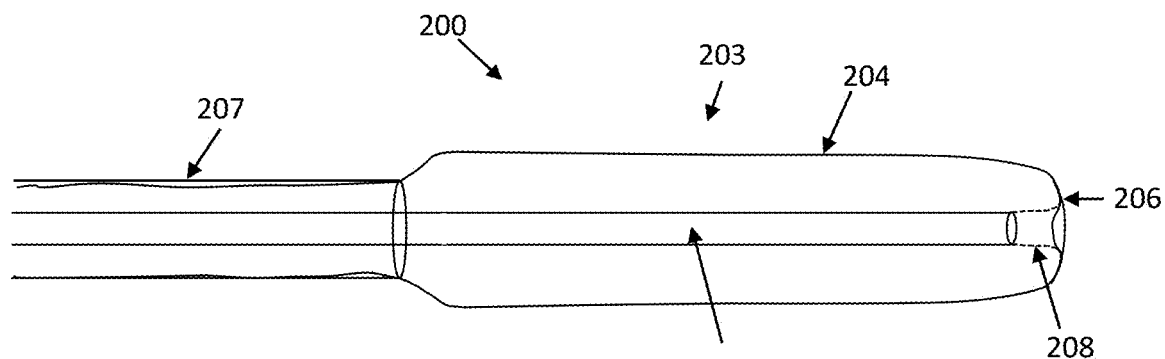
FIG. 2A illustrates one example of a self-rolling mechanical atherectomy apparatus that is configured so that the distal-facing portion of the tractor tube inverts over itself, unsupported, when the internal tube portion of the tractor tube is pulled proximally.

In general, described herein are self-rolling mechanical thrombectomy apparatuses having an inverting tractor tube that is configured to roll over and into itself at an unsupported distal-facing region that is at the very distal end of the apparatus, which may be used to capture and remove a blood clot from a blood vessel. These apparatuses may include a tractor tube that comprises a flexible tube that doubles back over (e.g., inverts) over itself so that an outer portion (e.g., an outer tractor tube portion) rolls and inverts, becoming an inner portion (e.g., an inner tractor tube portion) as this inner portion is pulled proximally. The apparatus typically includes an outer tractor pusher that supports and/or pushes the tractor tube just proximal to the proximal end of the outer tractor tube portion. The tractor tube may taper from the outer tractor tube diameter (which is typically larger than the diameter of the outer tractor pusher) to a diameter that is smaller than the inner diameter of the outer tractor pusher. The end of the tractor tube may be attached to the outer tractor pusher or it may be unattached to the outer tractor pusher. Any of these apparatuses may also include an inner tractor puller that is coupled to the other end of the tractor tube (e.g., the end that become the proximal end of the inner tractor tube portion when operating as described herein). Thus, the apparatus may be actuated to cause the tractor tube to roll and invert over itself, unsupported at the distal-most end, by pulling directly on the inner tractor tube portion or by pulling on an inner tractor puller that is coupled to the proximal end of the inner tractor tube portion.

Thus, in general, the inner tractor tube portion may therefore be pulled proximally to roll and invert the tractor tube over itself, without the need to roll over an annulus at the distal end of an elongate inverting support, since the apparatus may be configured to have a sufficient column strength on the outer portion of the tractor tube (the radially-expanded and longitudinally compressed outer tractor tube portion) to prevent buckling, bending or failure of the tractor tube when compression force (e.g., up to 300 g or more, 350 g or more, 400 g or more, 500 g, etc.) is applied to the outer tractor tube region by pulling the inner tractor tube region proximally. This is an improvement compared to other mechanical atherectomy apparatuses, including those described and shown in FIGS. 1A-1C, which typically include an elongate support that includes an annulus over which the tractor inverts at the distal end. The support (e.g., catheter) is typically positioned in the distal end region (e.g., the distal-facing tractor tube region) of the apparatus and the tractor tube inverts over it, rather than over itself; such embodiments may therefore require that the support be maneuvered with the tractor, any outer catheter and any inner puller.

For example, FIGS. 1A-1C shows an example of a mechanical thrombectomy apparatus that is not self-rolling. In this variation, an elongate inversion support is included (shown here as catheter 101) as a part of the mechanical thrombectomy apparatus. In this example, the elongate inversion support catheter 101 has a distal end region 103 that includes a distal end opening. The distal end region may have an increasing softness (measured by durometer, e.g., shore durometer) except that the very distal-most end region may be substantially less soft than the region immediately proximate to it.

In FIG. 1A, the elongate inversion support (e.g., catheter 101) is an elongate hollow catheter having a column strength that is sufficient to prevent buckling when the catheter is pulled over the distal annulus (distal end opening). Thus, the elongate inversion support may be configured so that it does not collapse (e.g., buckle) when 500 g or more of compressive force is applied (e.g., at least about 700 g, 600 g, 500 g, 400 g, 300 g, etc. of compressive force), for neurovascular applications. For peripheral vascular applications the elongate inversion support may be selected or configured to withstand a higher force (e.g., at least 1500 g of compressive force, at least about 2000 g, 1900 g, 1800 g, 1700 g, 1600 g, 1500 g, 1400 g, etc. of compressive force). The elongate inversion support may not be a full-length catheter, but may include a portion of a catheter, typically at the distal end, connected to a rod, wire, hypotube, or the like or may be skived. However, in each of these example, the support extends to the distal end region of the apparatus to provide a supporting surface over which the tractor tube can roll.

In FIG. 1A the support catheter 101 of the elongate inversion support may be any appropriate type of catheter or portion of a catheter, including microcatheters appropriate for neurovascular use.

FIG. 1B shows an example of a flexible tractor 144 coupled to a puller 146. In this example to form a pullable tractor assembly 140, the tractor is shown integrated with the puller, forming the assembly, however the support catheter 101 extends between the outer tractor tube portion and the inner tractor tube portion all the way to the distal-facing tractor portion at the distal-most end of the apparatus. In FIG. 1C, the tractor is a tube of material (e.g., wove, knitted, braided, etc.) that is flexible and elongate. In general, it may be particularly beneficial if the relaxed outer diameter of the flexible tractor in this first configuration has a greater outer diameter than the outer diameter of the catheter of the elongate inversion support into which the tractor will be positioned prior to inverting. The flexible and tubular tractor 144 may be sufficiently soft and flexible (e.g., having a low collapse strength) so as to easily roll and fold over the distal aperture of the elongate inversion support. The puller 146 may typically be a less-expandable (or non-expandable) structure (tube, puller, etc.). In the example shown in FIG. 1C, the tractor 144 is configured, e.g., by shape-setting (heat setting, etc.), to expand in the relaxed first configuration to a radial diameter that is between 1.1 and 10 times the diameter of the inner diameter of the catheter of the elongate inversion support when unconstrained, as shown in FIG. 1C. In FIG. 1C, the tractor of FIG. 1C is shown in an expanded, relaxed, configuration. Thus the expandable tractor may be biased to expand open. The tractor may be formed of a mesh, braided, woven, knitted, or sheet of material and is generally adapted to grasp the object to be removed (e.g., blood clot).

In FIG. 1C, the flexible tractor of FIG. 1B is shown with the tractor doubled back over itself and over the distal end of the catheter of the elongate inversion support 101. The distal end region is collapsed down, e.g., onto the puller and the elongate inversion support, and may be held collapsed. In this example a tractor hold 188 may be used to hold the tractor collapsed down onto the outer diameter of the elongate inversion support. However, in an unconstrained or deployed configuration the tractor (e.g., the portion that is inverted over the distal end of the catheter) has an outer diameter that is greater than the outer diameter of the catheter of the elongate inversion support. Thus, the tractor 144 may be biased so that it has a relaxed expanded configuration in the first configuration (as shown in FIG. 1C) that is greater than the inner diameter (ID) of the catheter of the elongate inversion support portion of the apparatus and the relaxed expanded configuration of the second configuration inverted over the catheter has an OD that is greater than the OD of the catheter. The tractor is expandable and may be coupled to the puller. In some variations the flexible tractor and the puller may comprise the same material but the tractor may be more flexible and/or expandable, or may be connected to a push/pull wire or catheter.

FIG. 1C illustrates the removal of a clot using this supported tractor apparatus shown in FIGS. 1A and 1B. In this example the apparatus is configured as a thrombectomy apparatus including a catheter of an elongate inversion support 101 and a flexible tractor that extends over the distal end region of the catheter and doubles-over itself at the distal end of the catheter to invert so that the external tractor end region is continuous with an inner less-expandable (in this example, less-expandable includes non-expandable) second distal end region 146 (puller) that extends proximally within the catheter and forms an inner lumen that may pass a guidewire. The pusher/puller member that may be a rod or other member that is continuous with the distal end region of the tractor.

However, described herein are self-rolling atherectomy (thrombectomy) apparatuses that do not need to roll over a support such as an elongate inversion support catheter. Instead, these apparatuses are configured to roll over just themselves, unsupported at their distal end. FIGS. 2A-2D illustrate examples of self-rolling thrombectomy apparatuses 200. Any of these apparatuses may include a tractor tube 206 (e.g., having, in a deployed configuration, an outer tractor tube portion 204, an inner tractor tube portion 208, and a distal-facing region 206 at which they invert) that may be configured to prevent collapse when under compression. In FIG. 2A, the apparatus also includes an inner tractor puller 205 coupled to the proximal end of the inner tractor tube portion 208, and an outer tractor pusher 207 which is shown (in this example) unconnected to the tractor tube.

Figure 2B:
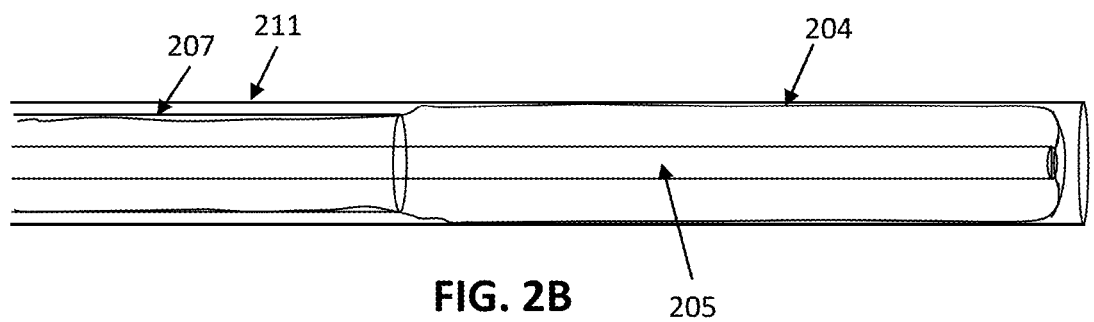
FIG. 2B shows the apparatus of FIG. 2A within a delivery catheter (e.g., a distal access catheter).
Figure 2C:
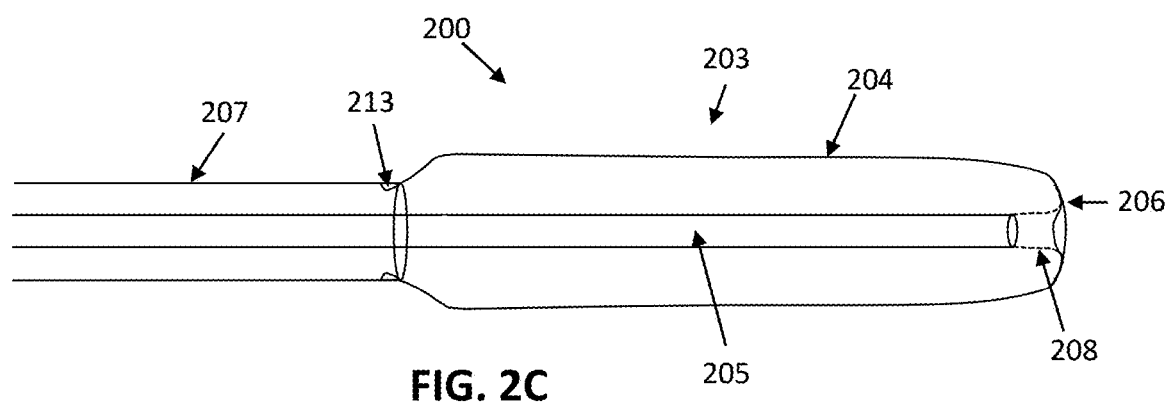
FIG. 2C is another example of a self-rolling mechanical atherectomy apparatus similar to the one shown in FIG. 2A, in which the end of the outer tractor tube portion of the tractor tube that is on the outside of the inverted tractor tube is attached to the outer tractor pusher.
Figure 2D:
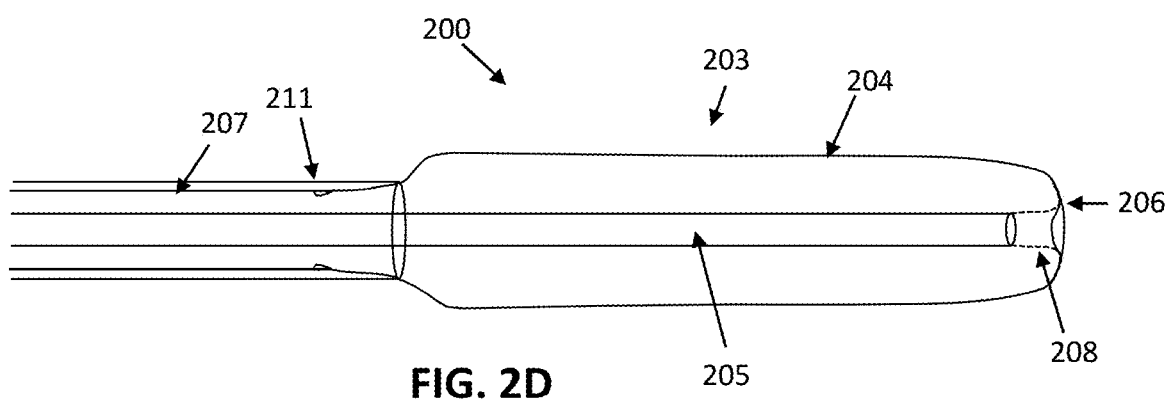
FIG. 2D is another example of a self-rolling mechanical atherectomy apparatus similar to the apparatus shown in FIG. 2D, in which the end of the outer tractor tube portion of the tractor tube that is on the outside of the inverted tractor tube is attached to an outer tractor pusher that is internal to an outer (e.g., distal access) catheter, and may be used to push or pull the tractor tube from the proximal end. The outer catheter may be slid distally to protect the tractor portion, or it may be held proximally relative to the outer tractor pusher to help support the proximal end of the outer tractor tube portion of the tractor tube.

FIGS. 2B-2D illustrate other variations of the self-rolling atherectomy apparatuses. In FIG. 2B, the apparatus of FIG. 2A is shown in a separate distal access catheter 211. The tractor tube is in an un-deployed configuration, within the distal access catheter; once deployed, the outer tractor tube portion may expand as shown in FIG. 2A. The self-rolling atherectomy apparatus shown in FIG. 2C is similar to that shown in FIG. 2A, however the proximal end of the outer tractor tube 204 is attached 213 to the outer tractor pusher 207. In FIG. 2D, the apparatus of FIG. 2C is shown including both an outer tractor pusher 207 as well as a distal access catheter 211.

Any of these apparatuses may include a guidewire lumen extending through the tractor tube and/or inner tractor puller that is configured to pass a guidewire.

Any of these apparatuses may include one or more projections that are configured to enhance engaging and/or maceration of a clot. Engaging the clot may be particularly, but not exclusively, helpful when the tractor is lubricious. It may also be particularly helpful to include projections that are retracted along the length of the tractor adjacent to the outer diameter of the elongate inverting support (e.g., catheter), for example, when positioning the apparatus within a vessel, but extend the projections outward from the tractor when rolling and inverting to grab a clot.

In many of the examples described herein, the tractor tube and/or inner tractor puller may extend for any appropriate distance (including between 1-100 cm, between 2-100 cm, greater than 1 cm, 2 cm, 3 cm, 4 cm, 5 cm, 6 cm, 7 cm, 8 cm, 9 cm, 10 cm, 11 cm, 12 cm, 15 cm, 20 cm, etc.). Similarly, the outer tractor pusher may extend to the same length or longer. The tractor tube may form an elongate lumen that is configured to allow passage of a guidewire, as mentioned. The tractor tube may also be configured to slide along the long axis within a distal access catheter (and/or an outer tractor pusher) lumen, e.g., during initial placement in the vessel. The tractor tube may therefore be longitudinally slideable within the distal access catheter, and may be arranged so a portion of the tractor tube (the distal-facing tractor region) doubles back over itself within the distal access catheter/outer tractor pusher or after being deployed from the distal access catheter or outer tractor pusher.

In general the self-rolling mechanical thrombectomy apparatuses described herein may be highly flexible, both before actuating and during operation.

The self-rolling mechanical thrombectomy apparatuses described herein typically create a rolling cylinder (tractor or tractor tube) that may be used to entrap or ensnare foreign objects from the human body.

The structure of the tractor tube may be formed from wires, threads, filaments, laser slotted tubing, or the like. The tractor tube may be braided, or may have a braided appearance. See, e.g., FIG. 3. When activated to roll and invert over itself, the tractor tube may produce a center-grabbing effect, similar to conveyor belt. The self-rolling mechanical thrombectomy apparatus may be delivered via a catheter (e.g., distal access catheter and/or outer tractor pusher) to a site of interest (peripheral vessel, neuro vascular, MIS surgical procedure, etc.). When the apparatus is in place, the device may be pushed and/or pulled, as described and illustrated below to activate the tractor tube so that it acts like a grabbing conveyor belt.

Figure 3A:
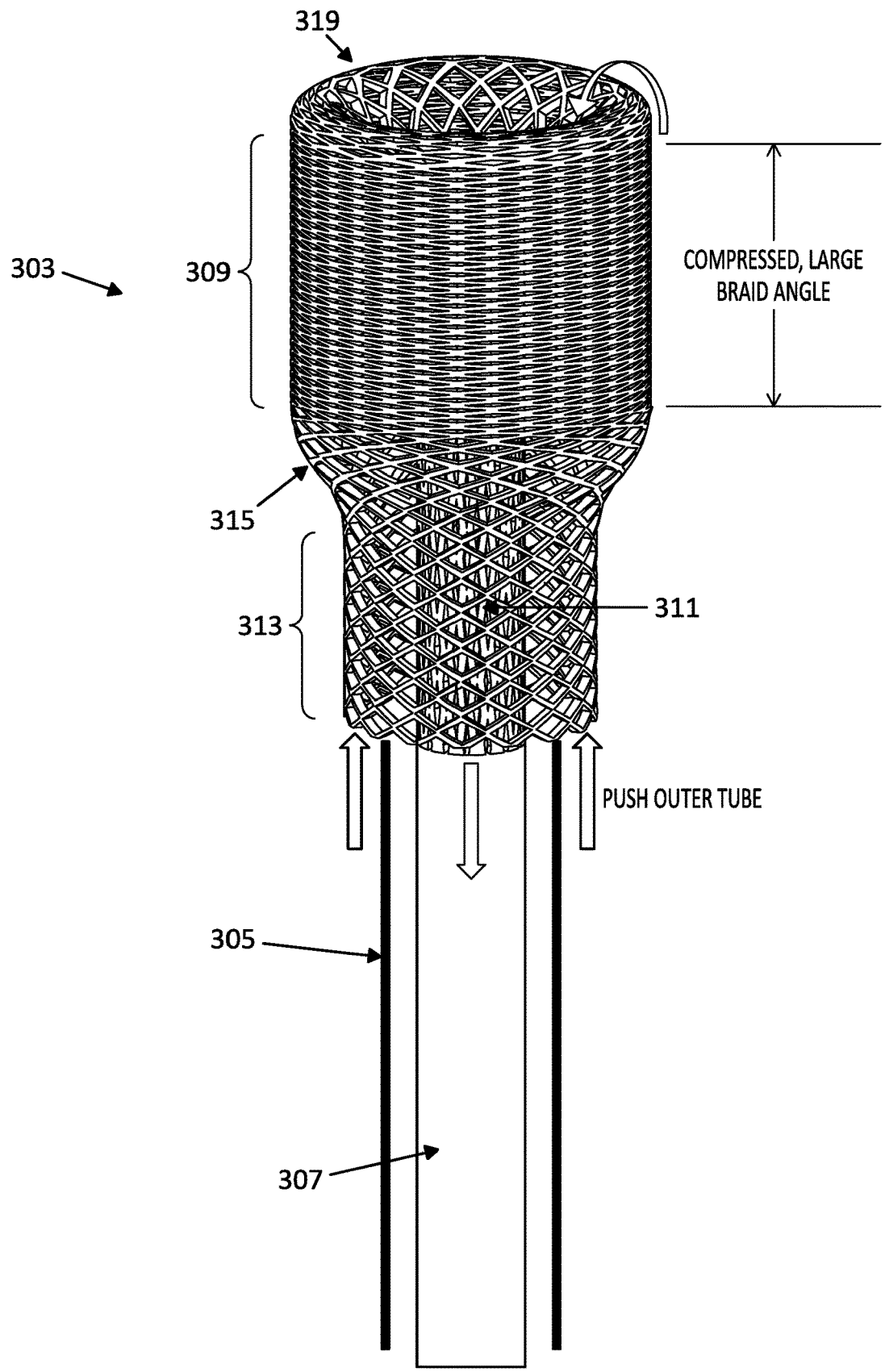
FIGS. 3A and 3B show examples of self-rolling mechanical atherectomy apparatuses.
Figure 3B:
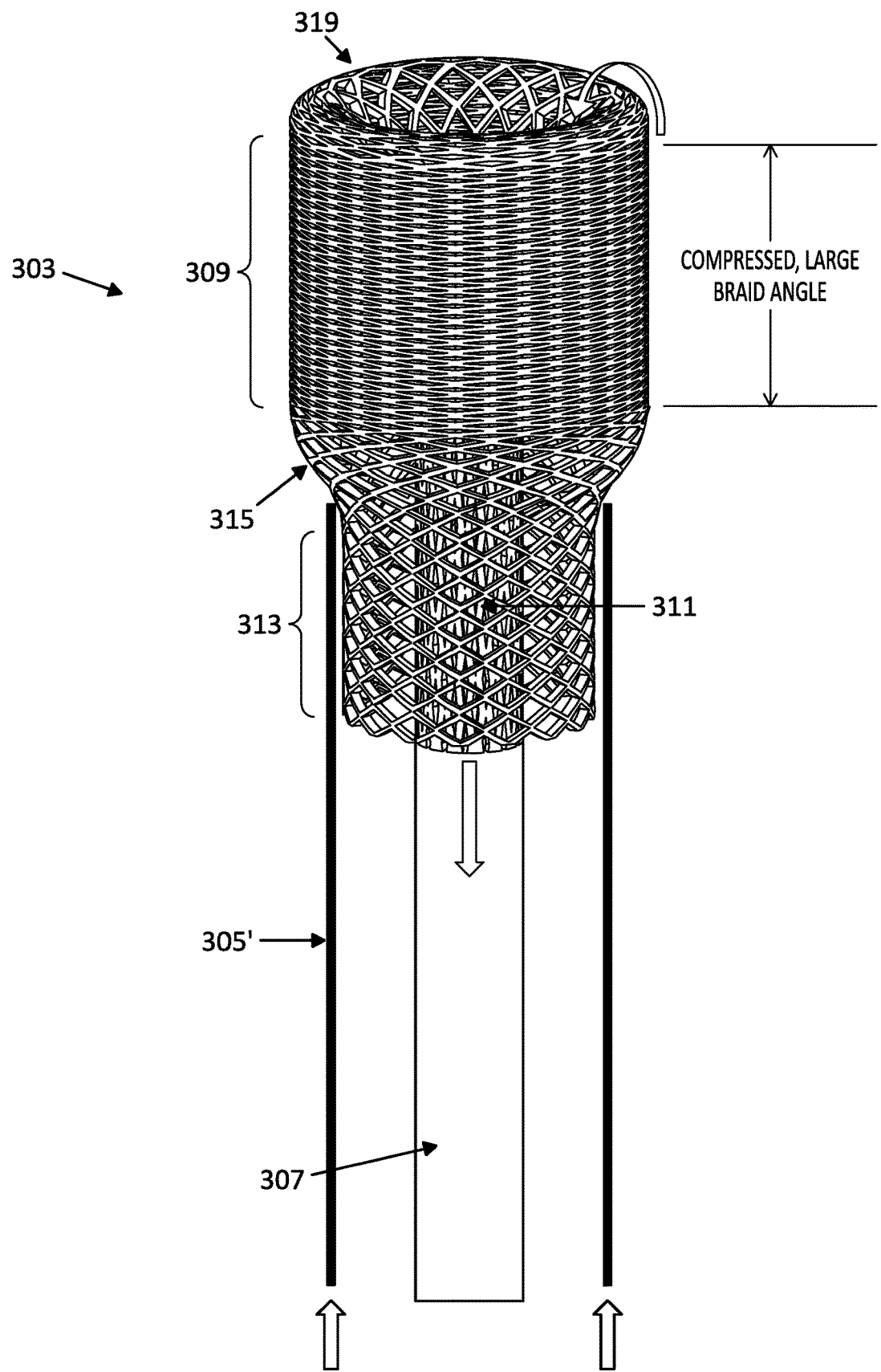

For example, FIG. 3A illustrates an apparatus including a tractor tube 303, outer tractor pusher 305 and inner tractor puller 307. The tractor tube is shown in a deployed configuration. In this example, the tractor tube 303 includes an outer tractor tube portion 309 that is shown in a compressed configuration having a large braid angle (e.g., greater than 150 degrees in this example). The tractor tube 303 also includes an inner tractor tube portion 311 that has a much smaller braid angle (e.g., less than 45 degrees in this example). The portion of the tractor tube proximal to the outer tractor tube portion 309 is a constrained region 313 that may be held (e.g., by shape setting, by a mechanical or structural constraint, such as a ring or catheter, etc.) in an intermediate configuration that is not as radially expanded as the outer tractor tube portion 309. A tapered region 315 is formed between the constrained region 313 of the tractor tube and the outer tractor tube portion 309 and may act as a bracing surface for an outer tractor pusher 305' (as shown in FIG. 3B). In FIG. 3A, the outer tractor pusher is shown pushing against 317 the end of the constrained region 313 of the tractor tube 303.

In FIGS. 3A and 3B, the tractor tube includes a distal-facing region 319 where the tractor tube rolls and inverts over itself. As will be illustrated below (e.g., in FIGS. 26A-26C), when the outer tractor pusher pushes against the end of the tractor tube closest to the outer tractor tube portion and the inner tractor tube portion is pulled proximally, the resulting compressive force compresses the outer tractor tube region 309, resulting in a column strength that prevents buckling and failure of the tractor tube while driving rolling of the outer portion of the tractor tube over and into itself at the distal-facing region 319 of the tractor tube.

Thus, any of these apparatuses may include a patterned (e.g., braided) tractor tube that may be shape set (e.g., heat set). The inner tractor tube region may be configured to have a lower column strength that allows it to expand to adjust to the clot diameter as it is drawn into the tractor tube.

Figure 4A:
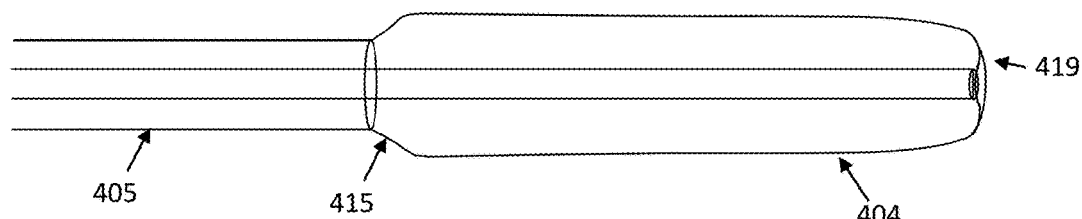
FIGS. 4A-4D illustrates the operation of a self-rolling mechanical atherectomy apparatus such as those shown in FIGS. 2A-3.
Figure 4B:
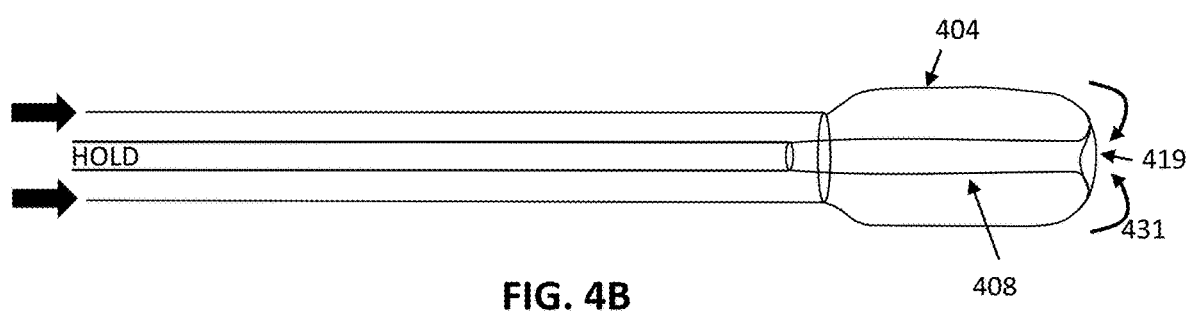
Figure 4C:
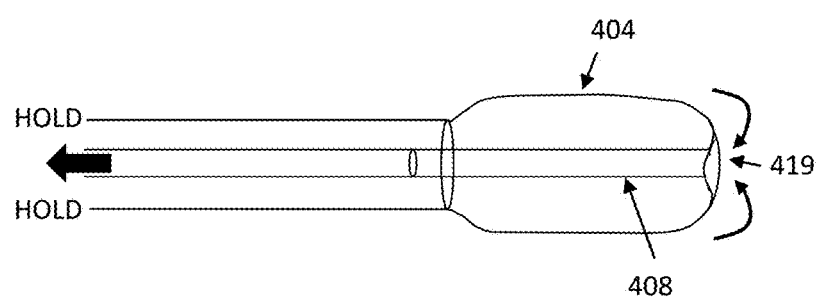
Figure 4D:
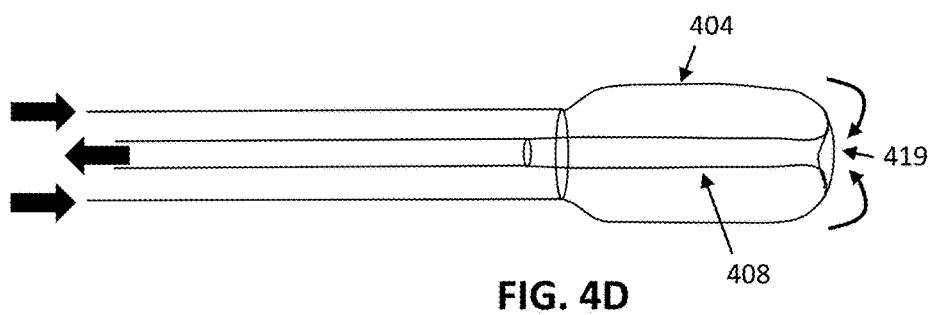

FIGS. 4A-4D illustrate examples actuating a self-rolling mechanical atherectomy apparatus. For example, in FIG. 4A, similar to that shown in FIG. 2A-2D, the self-rolling mechanical atherectomy apparatus includes a tractor region (having an expanded/deployed outer tractor region 404 that is continuous with an inner tractor region 408 after rolling and inverting over itself at the distal-facing region. In FIG. 4D the apparatus is shown deployed, with the outer tractor tube portion 404 expanded radially, having an outer diameter that is greater than the inner diameter of the outer tractor pusher 405. The outer tractor pusher is braced against the tapered region 415 proximal to the outer tractor tube region.

FIGS. 4B-4D illustrate alternative methods of actuating the tractor tube so that it rolls over itself and inverts, unsupported, only at the distal end. For example, in FIG. 4B, the outer tractor pusher 405 is pushed distally while the inner tractor puller is held, causing the outer tractor tube portion to roll over itself 431 and invert into the inner tractor tube portion, as shown. Similarly, in FIG. 4C, the tractor tube is actuated by pulling proximally on the inner tractor tube portion while holding the outer tractor pusher in place. FIG. 4D illustrates a combined method including both pushing the outer tractor pusher distally while pulling the inner tractor puller proximally; the two may be operated at different rates or distances. For example, the inner tractor puller may be pulled more proximately than the outer tractor pusher is pushed. In some variations, the entire apparatus may be advanced distally by pushing the outer tractor pusher distally, while still pulling the inner tractor puller proximally to roll the tractor tube into itself, as shown.

Figure 5A:
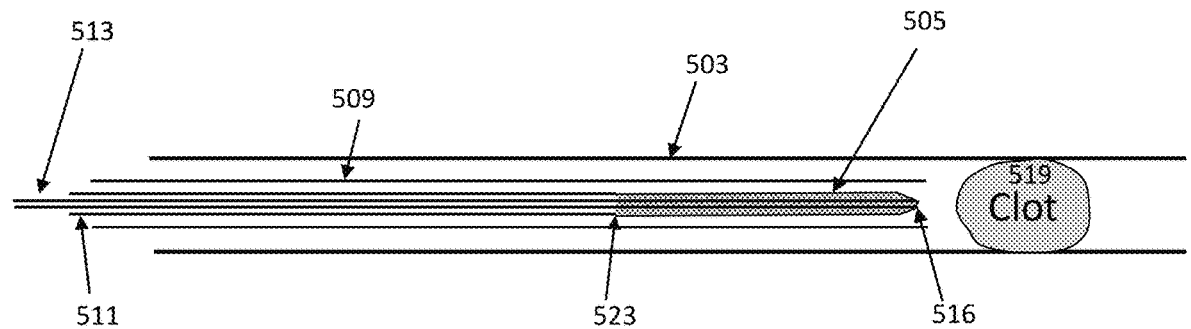
FIGS. 5A-5D illustrate the use of a self-rolling mechanical atherectomy apparatus such as those shown schematically above, to remove a clot (thrombus) from within a vessel.

FIGS. 5A-5D illustrate removal of a clot using a self-rolling mechanical atherectomy apparatus as described herein. In this example, the self-rolling mechanical atherectomy apparatus is a co-axial system including both a distal access catheter 509 and an outer tractor pusher 511, as well as an inner tractor puller 513. The apparatus is deployed in a blood vessel 503. In FIG. 5A, the self-rolling mechanical atherectomy apparatus is shown in an un-deployed configuration in which the tractor tube 505, which is connected at one end 523 to the outer tractor pusher, and at the other (inner) end to the inner tractor puller 513, is in a collapsed configuration within the lumen of the distal access catheter 509. The apparatus is initially positioned adjacent to the clot 519 (FIG. 5A). The distal-facing end 516 of the tractor tube is shown initially inside the distal end of the distal access catheter 509. The tractor tube 505 can either be preloaded in the distal access catheter 509 during access or delivered through the distal access catheter after the distal access catheter is positioned adjacent to the clot. The inner tractor puller can be cannulated (like a catheter) to allow delivery of a guidewire through its self to aid in delivery of the system to the clot. In FIG. 5A, the distal-facing region 516 of the tractor tube is the distal-most end of the assembly. Alternatively the distal-facing region 516 of the tractor tube can be inverted on itself (not shown) prior to delivering the system up to the clot.

The tractor tube may be made of a braid structure as described above. In this example, when constrained, it may have low braid angles (e.g., between 5-90 degrees, between 5-45 degrees, between 5-30 degrees, etc.). After it is released from the distal access catheter and deployed, the braid angle would may be much larger; once compression is applied to the outer tractor tube portion, e.g., by pulling on the inner tractor puller, the braid angle will be much larger (e.g., between 80-170 degrees), while the braid angle in the portion under tension (e.g., the inner tractor tube portion) may be much lower (e.g., less than 90 degrees, less than 80 degrees, less than 70 degrees, etc.). In this context, the braid angle referred to herein may refer to the braid angle relative to the proximal-to-distal axis, and the angle formed between intersecting strands of the mesh forming the tractor tube. This is illustrated below, in FIG. 9.

Figure 5B:
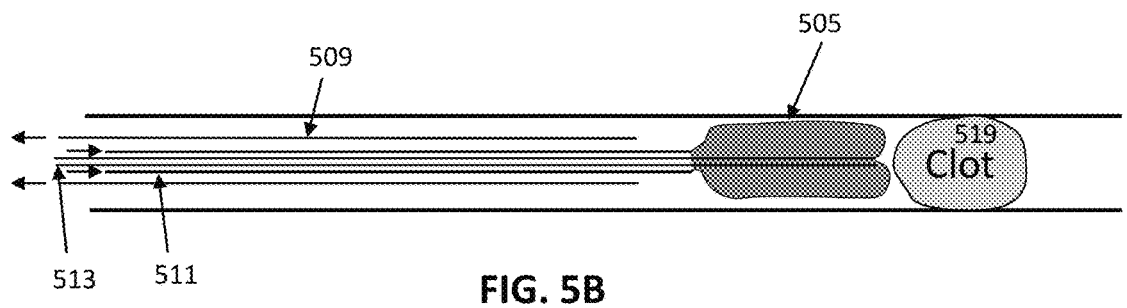

In FIG. 5B, the apparatus is shown deployed from the distal access catheter by pulling back on the distal access catheter to release the tractor tube, allowing it to expand radially to an outer diameter that is larger than the inner diameter of both the distal access catheter and the outer tractor pusher. Alternatively or additionally, the tractor tube can be driven forward out of the distal access catheter, (e.g. and into or towards the clot) rather than pulling back the distal access catheter.

Figure 5C:
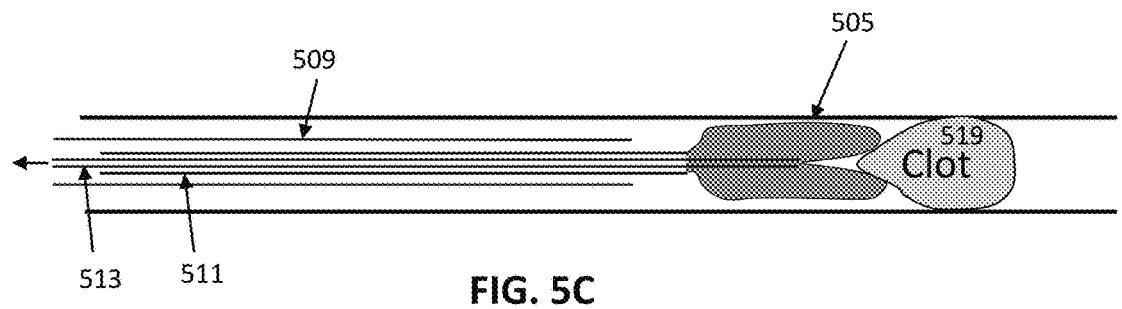
Figure 5D:
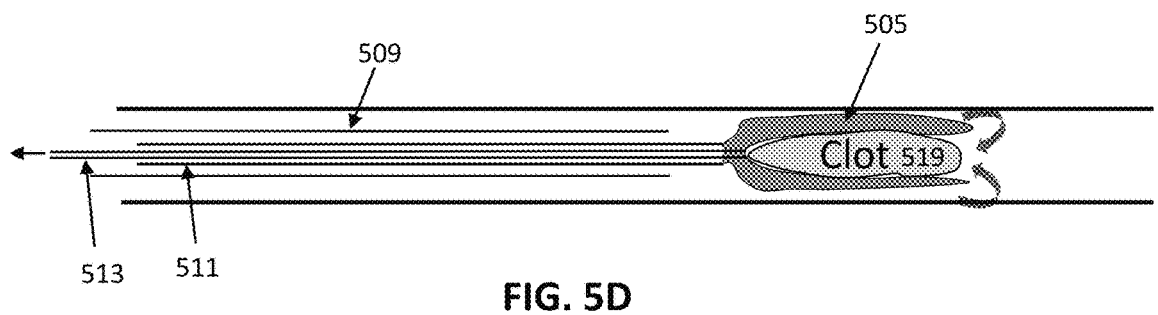

In FIG. 5C, the inner tractor puller 513 is retracted proximally to cause the tractor tube to invert over and into itself, unsupported at the distal-facing region of the tractor tube, so that it can grab clot and pull the clot into the tractor tube, as shown. The distal facing region of the of tractor tube forms a conical shape as it inverts on its self. By continuing to pull the inner tractor puller or fix the inner tractor puller and push the outer tractor pusher (or some combination of both movements), the conical shape formed on the tractor tube behaves like a conveyor, engaging (i.e., "grabbing") the clot 519 and pulling it into the tractor tube, engulfing the clot and capturing it, as shown in FIG. 5D.

Pushing the outer tractor pusher and/or pulling the inner tractor puller may be continued until the clot is fully captured. The clot can be removed from the vessel by either withdrawing the entire system, or by pulling the tractor tube into the distal access catheter and then pulling out the tractor tube while leaving the distal access catheter in place. The distal access catheter and or other components (e.g., the inner tractor puller and/or tractor tube) can have vacuum applied during, before and/or after clot engagement by the tractor tube. Alternatively, while pulling the inner tractor puller and pushing the outer tractor pusher, the tractor tube may be withdrawn inside the distal end of the outer tractor pusher with the clot.

FIGS. 6A-6D illustrate the operation of an alternative variation of a self-rolling mechanical atherectomy apparatus, in which the same catheter acts as both the distal access catheter (e.g., delivering the apparatus to the clot) and the outer tractor pusher, e.g., pushing or bracing the tractor tube from the proximal end to allow it to rollover itself distally.

Figure 6A:
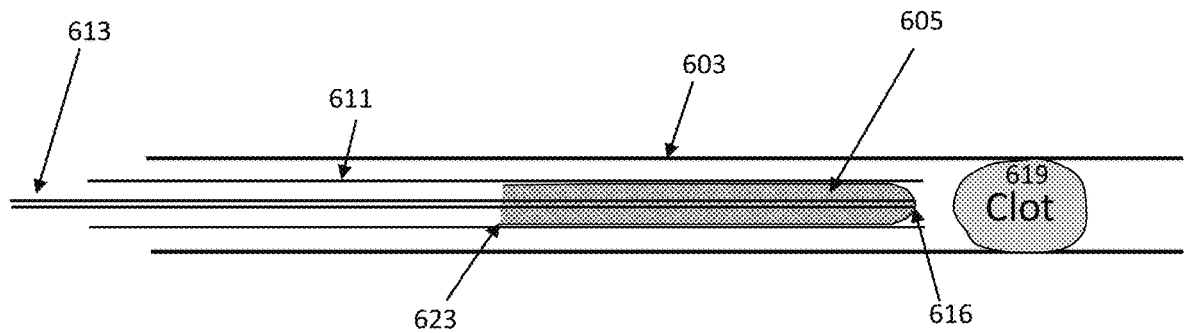
FIGS. 6A-6D illustrate a method of removing of a clot using a self-rolling mechanical atherectomy apparatus.
Figure 6B:
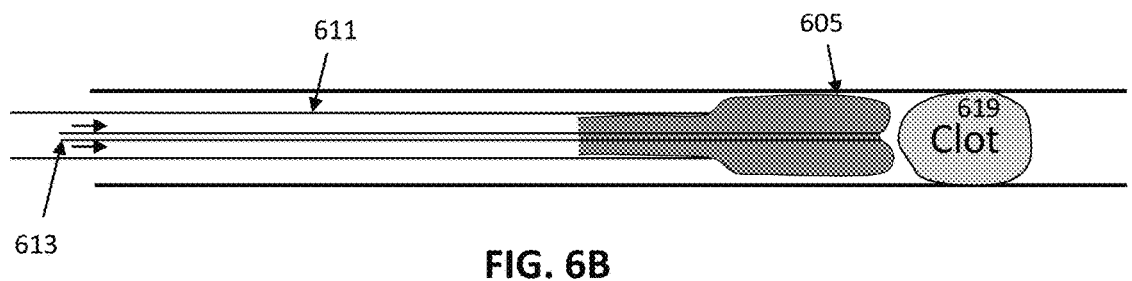

In FIG. 6A, the apparatus includes a tractor tube 605 that is connected at one end to an inner tractor puller 613; both the tractor tube and the inner tractor puller are held within the outer tractor pusher 611 (acting as a distal access catheter). This configuration may be referred to as a single axial system. The tractor tube is not attached 623 to the outer tractor pusher in this example. In FIG. 6B, the tractor tube may be deployed by pulling back the outer tractor tube (distal access catheter) 611 and allowing the outer tractor tube portion of the tractor tube to expand radially, as shown. The tractor tube 605 can be fully deployed into vessel or the proximal end of the tractor tube can remain in the outer tractor pusher, as shown. The outer tractor pusher braces against the tractor tube at a tapered end before (e.g., just proximal to) the outer tractor tube portion. Alternatively, the tractor tube can be driven forward into the clot and out of the outer tractor pusher rather than pulled back to deploy the tractor tube in the vessel.

Figure 6C:
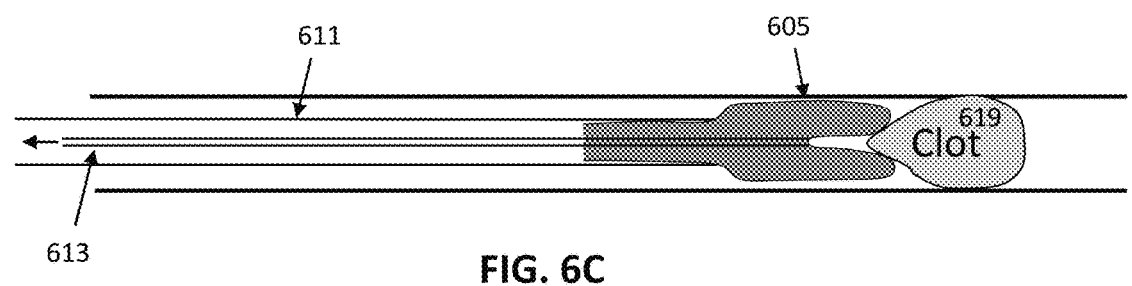
Figure 6D:
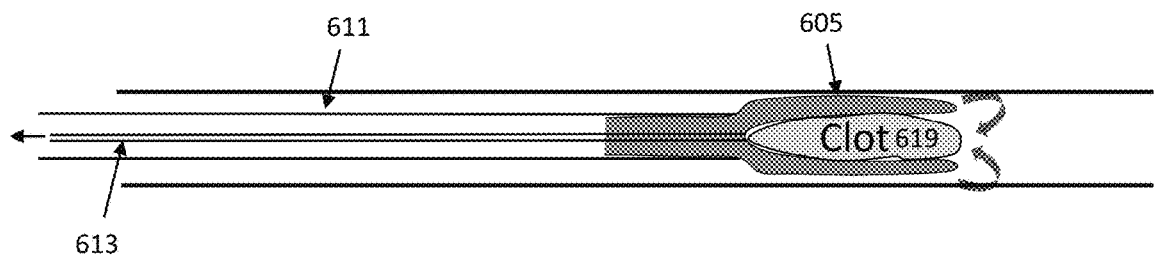

In FIG. 6C, the inner tractor tube portion is retracted proximally so as to invert the tractor tube over and into itself, thereby engaging the clot 619. The distal-facing region of the tractor tube forms a conical shape as it inverts on itself when pulling the inner tractor puller and/or pushing the outer tractor pusher. By continuing to pull inner tractor puller or holding the inner tractor puller fixed and pushing the outer tractor pusher (or some combination of both movements), the conical shape formed on the tractor tube may act like a conveyor, engaging and pulling the clot into tractor tube (i.e., engulfing and capturing the clot). As shown in FIG. 6D, the clot may be engaged/grabbed and enclosed at least partially, within the tractor tube and removed from patient.

The self-rolling mechanical atherectomy apparatuses described herein may provide improved clot engagement with lower grabbing forces, and without jamming. As will be described in greater detail below, these apparatuses may be tuned to provide sufficient column strength so that they do not fail during operation, and the forces required to invert the tractor tube are relatively small. The high column stiffness of the expanded tractor tube acts like a catheter-tube, enabling it to be easily advanced forward in a vessel. Finally, these apparatuses can be used with or without aspiration.

As mentioned above, the self-rolling mechanical atherectomy apparatuses described herein are specifically configured so that the tractor tube portion rolls over itself, unsupported, at its distal end when pulling the inner tractor tube portion proximally and/or pushing the outer tractor tube portion distally. Generally, when pushing and/or pulling a flexible tube that is woven, braided, knitted, or even solid, the tractor tube will bend, buckle or collapse. This is particularly true of flexible tractor tubes that inverted over themselves and biased to expand radially outward in either or both the outer tractor tube configuration and the inner tractor tube configuration). Buckling and collapsing are therefore failure modes for such tractor tube which must be avoided if operating a self-rolling mechanical atherectomy apparatus.

Figure 7A:
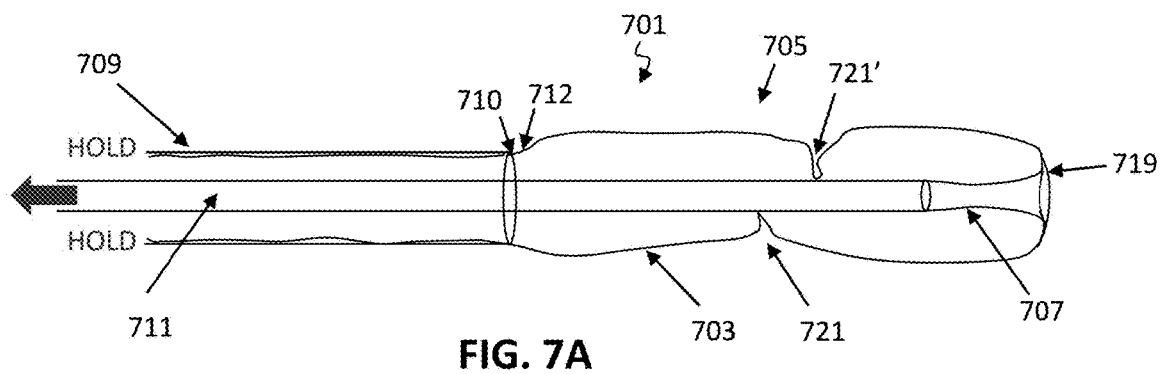
FIG. 7A-7B illustrate possible failure modes for the operation of a self-rolling mechanical atherectomy apparatus.

FIGS. 7A-7B and 8A-8B illustrate these common failure modes. In FIG. 7A, self-rolling mechanical atherectomy apparatus 701 similar to those shown in FIGS. 2A-2D, 3A-3D, 4A-4D, 5A-5D, and 6A-6D are shown buckling or collapsing when either or both the inner tractor tube portion is pulled proximally (e.g., by pulling an inner tractor puller) or the outer tractor tube portion is pushed proximally (e.g., by pushing an outer tractor pusher). In FIG. 7A, a distal access catheter 709 is configured as an outer tractor pusher because a tapered portion 712 of the tractor tube that is proximal to the outer tractor tube portion 703 of the tractor tube 705 is pushed against the distal opening face 710 of the distal access catheter when the outer tractor pusher (distal access catheter 709) is pushed distally while holding the inner tractor puller 711 fixed relative to the vessel wall as indicated (or alternatively pulling it proximally). In this example, although the outer tractor tube portion 703 may being rolling over itself, unsupported, at its distal end (distal facing end 719), the outer tractor tube portion 803 in the expanded configuration (e.g., not constrained within the distal access catheter) does not have sufficient column strength to prevent the outer tractor tube portion from compressing and buckling. One or more outer tractor tube regions buckle 721, 721', collapsing under the compressive force on the outer tractor tube portion. In some variations, the tractor tube will roll slightly, as shown in FIG. 7A; alternatively, the tractor tube will not roll at all, but will immediately collapse or buckle.

In FIG. 7A, the force required to roll and invert at the distal end is greater than the force that will causes the expanded outer tractor tube region to buckle; as a result, the outer tractor tube buckles. Once the tractor tube 705 begins to buckle or collapse, it will no longer roll over the distal end region, may lead to further collapse. In addition, the force required to advance the increasingly collapsed tractor tube distally by pushing the outer tractor pusher/distal access catheter may increase substantially.

Figure 7B:
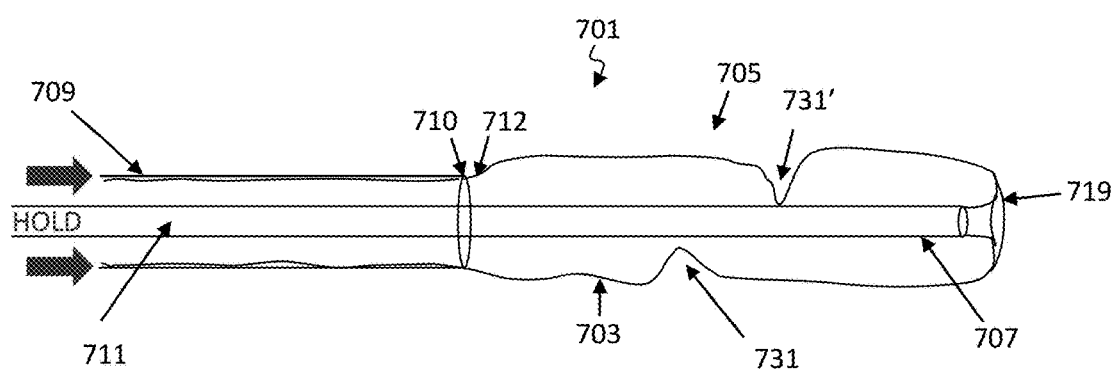

A similar failure may occur when pulling the inner tractor tube region proximally, as illustrated in FIG. 7B. In FIG. 7B, a distal access catheter 709 is braced against the distal opening face of the distal access catheter and the inner tractor tube portion 707 is pulled proximally, by pulling on the inner tractor puller 711. The outer tractor tube portion 703 is in the expanded configuration (e.g., not constrained within the distal access catheter). Because the tractor tube 705 is unsupported at the distal-facing end 719, pulling on the inner tractor tube portion 707 compresses the outer tractor portion 705. In this case, as in FIG. 7A, the compressive force is greater than column strength of the outer tractor tube portion. Typically, the force applied to actuated the devices described herein may be up to a maximum of about 400 g of force, (e.g., 300 g of force, 350 g of force, 400 g of force, 450 g of force, 500 g of force, 550 g of force, 600 g of force, etc.), particularly in neurovascular applications. When the applied actuating force, which becomes the applied compressive force, is greater than the column strength of the outer tractor tube portion, the outer tractor tube portion buckles 731, 731' as shown in FIG. 7B.

Thus, in general, for any of the apparatuses described herein to operate, they must be configured so that the column strength of the expanded outer tractor tube portion, which may be a braided or woven material, is greater than at least the maximum force in the range of forces used to actuate the apparatus so that the tractor tube rolls and inverts over itself, unsupported, at its distal-facing end region. For example, the apparatuses described herein may be configured so that the outer tractor tube portion has a column strength that is sufficient to resist buckling or collapse under a compressive force of least about 500 g.

In addition to the column strength of the outer tractor tube under compression, which may lead to buckling or collapse around the longitudinal length of the apparatus, as shown in FIGS. 7A-7B, FIGS. 8A-8B illustrate another failure mode causing collapse at the proximal end of the outer tractor tube portion, which may occur when the proximal tapered portion of the expanded tractor tube buckles against the outer tractor pusher/distal access catheter.

Figure 8A:
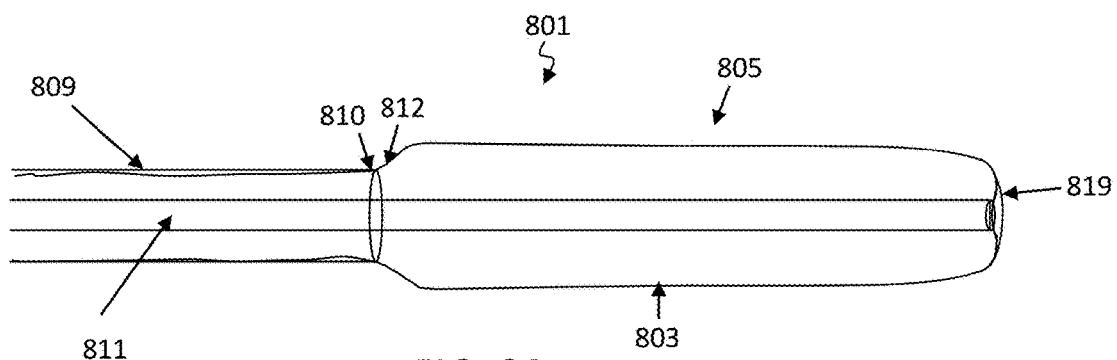
FIGS. 8A and 8B illustrate another example of a possible failure mode of a self-rolling mechanical atherectomy apparatus.

For example, in FIG. 8A, a self-rolling mechanical atherectomy apparatus 801 is shown in an expanded or deployed configuration. The tractor tube 805 includes an outer tractor tube region 803 that is expanded out of the distal end of the distal access catheter. The tractor tube includes a proximal tapered region 812 that is braced against the distal end opening 810 of the distal access catheter 809. The apparatus also includes an inner tractor puller 811 that is connected to an end of the tractor tube 805; when the tractor tube rolls and inverts over itself at the distal-facing end 819, the inner tractor puller 811 will be attached to the proximal end of the inner tractor tube region. FIG. 8A shows the apparatus prior to actuating by either or both pulling the inner tractor puller and/or pushing the outer tractor pusher (in this configuration, the distal access catheter).

Figure 8B:
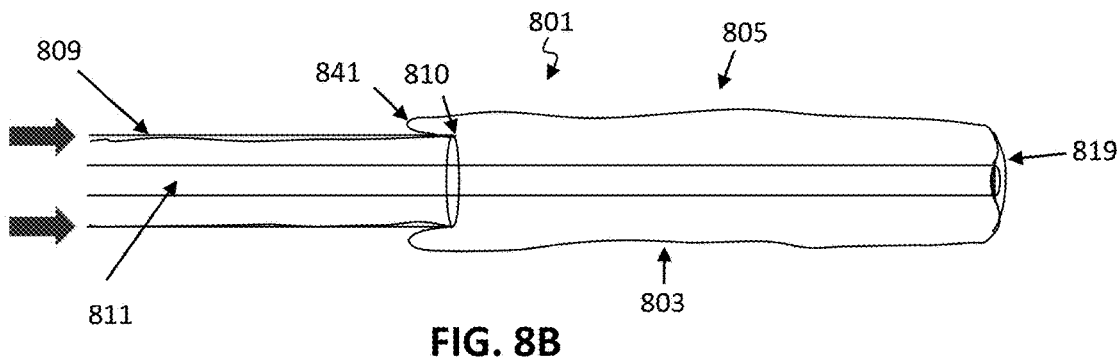

In FIG. 8B, upon actuating the apparatus, e.g., by either or both pulling or pushing, the tapered region 812 at the proximal end of the outer tractor tube portion 803, against which the distal end opening 810 of the outer tractor pusher 809 pushes or braces collapses, folding the proximal end of the outer tractor tube portion over the distal access catheter. In this example, the relative weakness of the proximal tapered region between the expanded outer tractor tube portion and the distal end opening of the outer tractor pusher/distal access catheter causes this tapered region to fail, so that the tractor tube rolls over 841 the open end 810 of the distal access catheter (and therefore over itself proximally), rather than rolling over itself distally at the distal-facing opening 819.

As illustrated by FIGS. 7A-7B and 8B-8B, the apparatus, and particularly the tractor tube, should preferably be configured so that the column strength of the expanded outer tractor tube portion is greater than the maximum applied compressive force (e.g., actuating force), and the strength of the tapered region should resist the force applied by the outer tractor pusher.

Thus, a functional self-rolling mechanical atherectomy apparatus for removing a clot from a vessel should be configured to avoid at least these failure modes. Specifically a self-rolling mechanical atherectomy apparatus should have a tractor tube with a sufficient column strength in an expanded outer tractor tube portion so as to resist a compressive force of greater than at least some minimum threshold (e.g., 400 g of force, 500 g of force, 600 g of force, etc.). Alternatively or additionally, the tractor tube should have a tapered region proximal to the expanded outer tractor tube portion that is configured to resist the distally directed force applied by the outer tractor pusher.

Described herein are configurations and parameters for forming a tractor tube meeting these criterion. For example, the tractor tube may be formed of a material (and particularly a mesh, e.g., braided or woven material) having a braid angle in the expanded tractor tube, when compressed by pushing and/or pulling, in a proximal-to-distal axis that is between about 80 and about 170 degrees. The inner tractor tube portion may have a braid angle in the proximal to distal axis under tension of less than 80 degrees (e.g., less than 75 degrees, less than 70 degrees, less than 65 degrees, less than 60 degrees, less than 50 degrees, less than 45 degrees, less than 40 degrees, less than 35 degrees, etc.). In addition, the amount of expansion f the outer tractor tube portion may be between +/−about 30% of the outer diameter of the outer tractor pusher. In addition, for woven or braided configurations, the number of strands (or strand equivalents) may be at least 12 (e.g., 12 or more, 16 or more, 18 or more, 24 or more, 36 or more, 40 or more, 50 or more, 60 or more, 72 or more, etc.). The expanded tractor tube may also be configured to have a minimum length (e.g., of 0.7 cm or greater, e.g., 0.8 cm or greater, 0.9 cm or greater, 1 cm or greater, 1.2 cm or greater, etc.). For example, the unsupported tractor tube length may be ≥1 cm. When the tractor tube is formed of a woven or braided material, the material used for the tractor tube may be a monofilament or a collection of filaments. The tractor tube may also include a number of pores (e.g., cells) formed by the strands; the porosity of the mesh may be, for example, 70% or less (e.g., 65% or less, 60% or less, 55% or less, 50% or less, 45% or less, etc.) and in particular, 60% or less.

In general, the applicants have found that, for braided or woven tractor tubes having the following ranges of parameters, a self-rolling (e.g., unsupported) tractor tube apparatus will not kink or collapse or otherwise fail as described in FIGS. 7A and 7B and 8A-8B: the tractor tube may be formed of a least 10 strands and have a distal-to-proximal facing braid angle for the expanded configuration of the outer tractor tube portion of between about 80 and about 170 degrees, a distal-to-proximal facing braid angle of the tensioned inner tractor tube portion that is always less than the braid angle of the expanded outer tractor tube portion and is about 80 degrees or less, further wherein the outer tractor tube portion of the tractor tube is configured to expand to between about +/−30% of the outer diameter of the outer tractor pusher. Such tractor tubes may have sufficient column strength to resists collapsing when actuated (e.g., with at least 500 g of force) and under compression so as to roll over the distal-facing end of the tractor tube, unsupported.

For example, it may be preferable that, for braided or woven tractor tubes, the tractor tube is formed of a least 10 strands of materials (more preferably at least 12 strands of material, still more preferably at least 16 strands of material), where the strands have a thickness of about 0.003 inches or greater. The fibers forming the tractor tube may have a distal-to-proximal facing braid angle of between about 80 and about 170 degrees in the expanded outer tractor tube portion under compression and a braid angle in a distal-to-proximal direction of the tensioned inner tractor tube portion that is less than the braid angle of the expanded outer tractor tube portion and is 80 degrees or less. The outer tractor tube portion of the tractor tube may be configured to expand to within +/−about 30% of the outer diameter of the outer tractor pusher. The length of the tractor tube may be at least 1 cm or more.

Thus, in any of the apparatuses described herein, the tractor tube may be flexible enough to be pushed through a catheter located in the tortuous neuro vasculature anatomy. The tractor may be delivered partially inverted (e.g., rolled on itself) to the clot face through a catheter. The distal-facing end of the tractor tube is generally unsupported (e.g., the tractor tube does not roll over and against the distal opening of a catheter or other support). The unsupported outer tubular length of the tractor tube may be of adequate length when in its axial compressed form to grab typical clot lengths seen in stroke patients (e.g., 1 cm or greater) in a single pass/pull. Typically, the outer tractor tube portion rolls around the distal-facing end of the tractor tube when the distal-facing end of the tractor tube is adjacent and may be in contract (e.g., jammed up against) a clot. The user may then drive the outer tube distally by (or while) pulling the inner tractor puller, and therefore the inner tractor tube portion, proximally, and either supporting or pushing the outer tractor pusher distally. The axial pushing forces on the tractor tube generate an axial compressive load on the expanded outer tractor tube portion and, as long as the column strength is greater than the compressive load, and as long as the strength of the tapered region against the outer tractor pusher is sufficient, the tractor tube will roll over itself, unsupported, without kinking, collapsing or otherwise failing. Thus, the flexible tractor tubes described herein are configured to have sufficient axially columnar stiffness that when axially compressive forces are applied, the outer tractor tube portion rolls and inverts rather than bunch, buckle, accordion or collapse.

In general, the outer tractor tube portion may be configured so that the maximum expansion relative to the outer diameter of the outer tractor pusher that it is supported against is sized appropriately so device doesn't jam in vessel when pushed & axially compressed, or collapse as shown in FIG. 8B. If the expanded outer diameter (OD) of the outer tractor tube portion is too big, the tractor tube may lock in the vessel when being pushed, rather than advancing in the vessel or driving the rolling/inverting action. Similarly, if the tractor tube OD is too small, the tractor tube may not be large enough to grab the clot sufficiently (e.g., it may core out center of clot only, leaving some of the clot behind or requiring additional removal steps. Thus, in general, the tractor tube may be configured so that it does not over-expand, e.g., due to compressive forces are applied by user to the tractor tube.

In any of the apparatuses described herein, the tractor tube may have sufficient coarseness at its rolling tip to engage and grab a clot. For example, when the tractor tube rolls over the distal end of the apparatus, the inner tractor tube portion may maintain an adequate inner diameter (ID) to leave room for clot. Thus, the inner tractor tube portion may also be configured to expand radially outwards somewhat, rather than collapse onto itself when pulled and tensioned proximally. For example, the inner tractor tube portion may be biased radially outwards to have an inner diameter that is 30% or more of the inner diameter of the expanded outer tractor tube portion (e.g., 35% or more, 45% or more, 50% or more, 55% or more, 60% or more, etc.). The tractor tube may generally be porous, which may provide additional coarseness. For example, it may be beneficial to have a porous structure that has relatively small pores (e.g., small enough to capture all the clot when inverting/rolling), and a sufficient number of pores (e.g., less than 70%, less than 65%, less than 60%, less than 55%, less than 50%, etc. porosity).

Any of the apparatuses described herein can be used in combination with vacuum/aspiration. For example a vacuum may be applied through the inner tractor puller and/or the tractor tube. Further, any of the apparatuses described herein may be configured so that they are visible under fluoroscopy; in particular, the tractor tube or a portion of the tractor tube may be configured so that it is visible under fluoroscopy.

Figure 9:
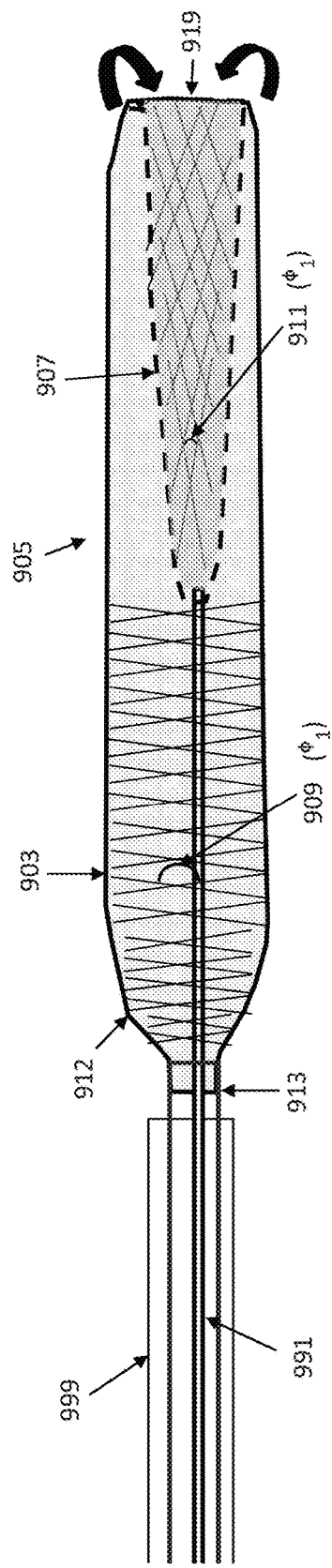

FIG. 9 shows one example of a self-rolling thrombectomy apparatus with a braided tractor tube that is configured to provide sufficient column strength in the outer tractor tube portion when compressed to as to prevent failure by kinking, bending, collapsing or otherwise failing. In FIG. 9, the apparatus includes a distal access catheter 999, an outer tractor pusher 913, and a braided tractor tube 905. The braided tractor tube has an expanded, outer tractor tube portion 903, a tapered portion 912 proximal to the outer tractor tube portion, and an inner tractor tube portion 907 that is connected to an inner tractor puller 991. The tractor tube 905 inverts over itself so that the outer tractor tube portion rolls and inverts to become the inner tractor tube portion at the distal-facing end region 919.

Figure 10:
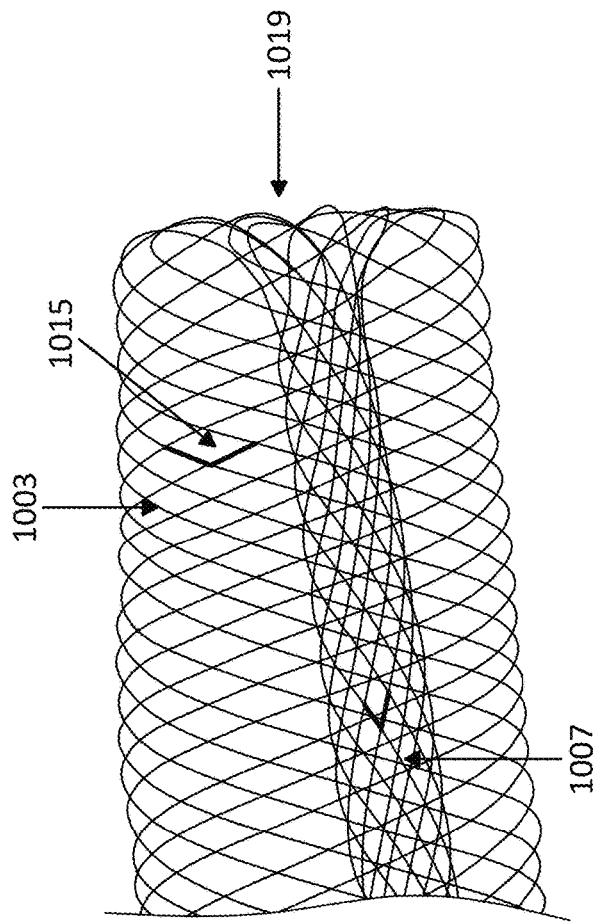
FIG. 10 is an example of the distal-facing region of a self-rolling mechanical atherectomy apparatus.

In FIG. 9, an exemplary distal-to-proximal facing braid angle 909 ($\Phi_1$) for the outer tractor tube portion is illustrated. This $\Phi_1$ angle may be between 80 degrees and 170 degrees, but is more preferably >90 degrees. In the example shown in FIG. 9, it is between 110 degrees and 160 degrees. FIG. 10 shows an example of a distal-facing end region 1019 of a prototype tractor tube 1003 that is configured as described above, including having a distal-to-proximal facing angle ($\Phi_1$) 1015 of between 80 degrees and 70 degrees; in this example, the $\Phi_1$ angle is approximately 130 degrees. Returning to FIG. 9, the outer tractor tube portion in the expanded state has a high braid angle, jammed braid state, and max diameter that provide a high resistance to axial compressive force (e.g., column strength in compression), which makes it easy to advance/push braid structure forward, as well as resisting kinking and failure of the tractor tube. In FIG. 9, the distal-to-proximal braid angle of the inverted, inner tractor tube region 911 (shown as $\Phi_2$) is typically much smaller than $\Phi_1$, and may be, e.g., less than 90 degrees (e.g., less than 80 degrees, less than 70 degrees, less than 60 degrees, etc.). In FIG. 10, the distal-to-proximal facing braid angle of the inner tractor tube portion 1007 ($\Phi_2$) is also shown, and in this example is about 35 degrees. The low braid angle of the inner tube region is formed as the braid collapses to a small diameter when the tractor tube rolls around distal-facing end, and inverts inside the larger outer tractor tube portion. In FIG. 10, the braided tractor tube is formed of 24 strands ("24 end") of 0.0005"×0.0010" NiTi ribbon that is braided to have a maximum OD (when axially compressed of 2.5 mm.

Figure 11:
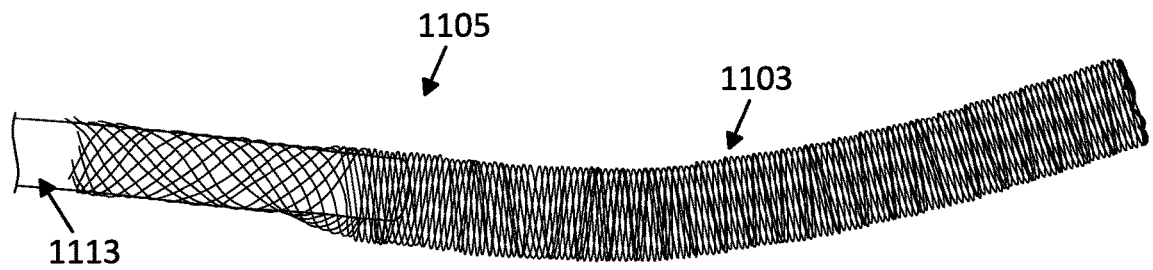
FIG. 11 is an example of a self-rolling mechanical atherectomy apparatus including a tractor tube that is inverted over itself, and an inner tractor puller.
Figure 12:
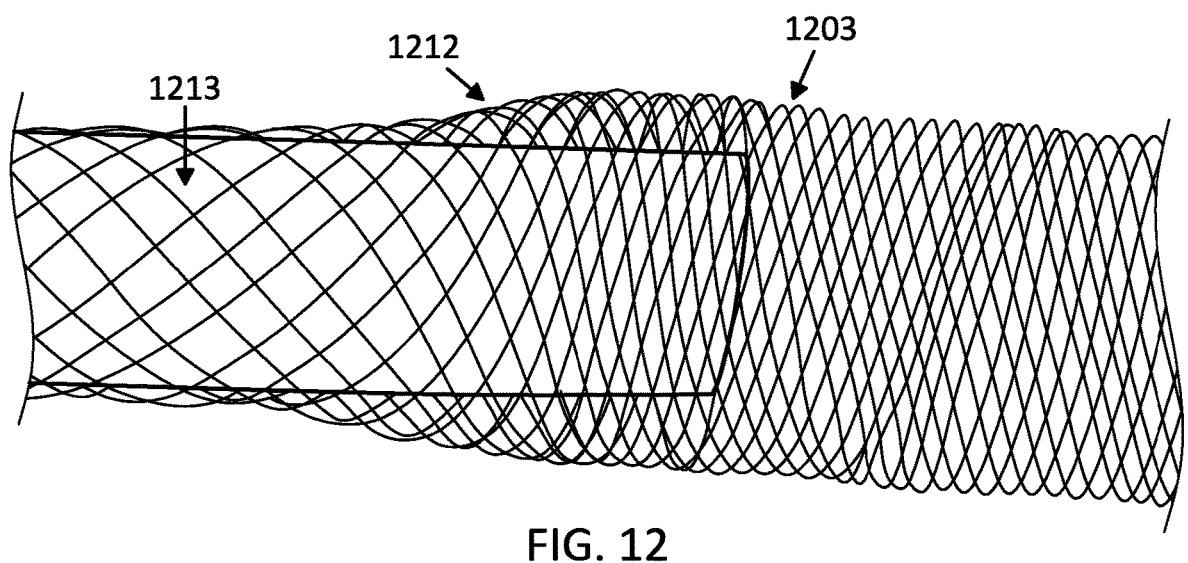
FIG. 12 shows an example of the attachment of an outer tractor tube portion of a tractor tube connected to an outer tractor pusher, showing the braid angle of the outer tractor tube portion.
Figure 13:
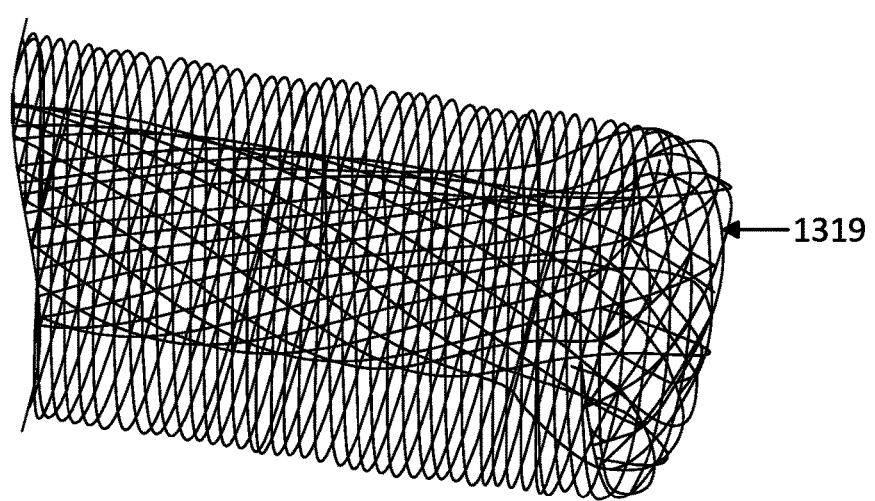
FIG. 13 is another example of a distal-facing region of a self-rolling mechanical atherectomy apparatus, similar to that shown in FIG. 10.

FIGS. 11, 12 and 13 illustrate other examples of tractor tubes that may be used as part of a rolling mechanical atherectomy apparatus as described. In FIG. 11, the tractor tube 1105 is shown inverted over itself. The outer tractor tube portion is expanded to a large braid angle. As described and shown above, the braid angle is the distal-to-proximal facing angle formed between intersecting strands of the braid. In FIG. 11 and FIG. 12, the braid angle is greater than 120 degrees for the fully expanded outer tractor tube portion 1103. The inner tractor tube portion is not easily visible in FIG. 11. The proximal end of the outer tractor tube portion is tapered, and has a smaller braid angle as it tapers down (e.g., the tapering braid angle goes from the expanded outer tractor tube portion braid angle of >120 degrees to approximately 90 degrees where it is attached to the outer surface of the outer tractor pusher 1113. The tractor tube in FIG. 11 is formed of a braided Nickle titanium (NiTi) material. In FIG. 12 a similar tractor tube is shown, including a braid angle (distal-to-proximal facing) of the expanded outer tractor tube portion 1203 that is approximately 150 degrees. The tapered region 1212 proximal to the outer tractor tube portion transitions to a smaller braid angle (e.g., between about 100 and 70 degrees), where it is attached to the outer tractor pusher 1213. FIG. 13 shows a distal-facing end of a tractor tube of a self-rolling apparatus that is unsupported. The distal-facing end 1319 of the tractor tube shown illustrates the inverted, rolling end of the tractor tube. The tractor tube does not enclose or surround a support element (e.g., catheter, loop, etc.) at or near the distal-facing end that is rolling.

Figure 14A:
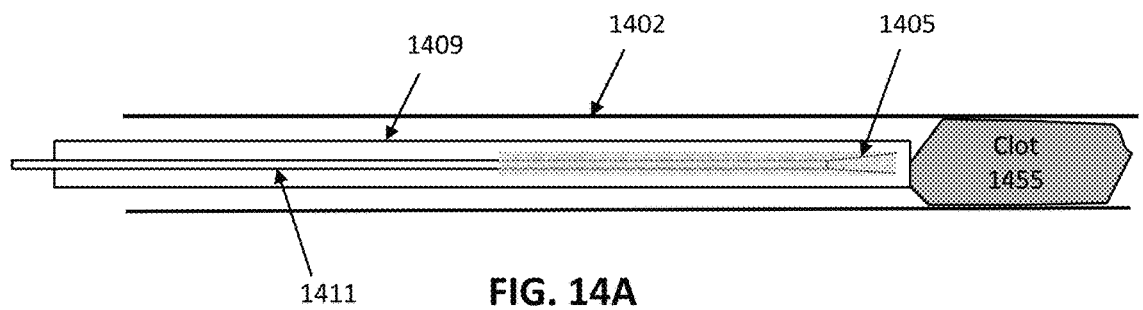
FIGS. 14A-14D show examples of a method of using a self-rolling mechanical atherectomy apparatus having a pre-shaped tractor tube.
Figure 14B:
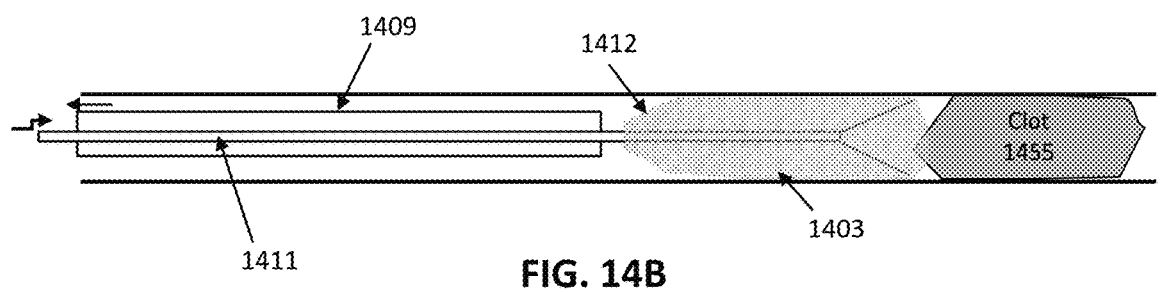
Figure 14C:
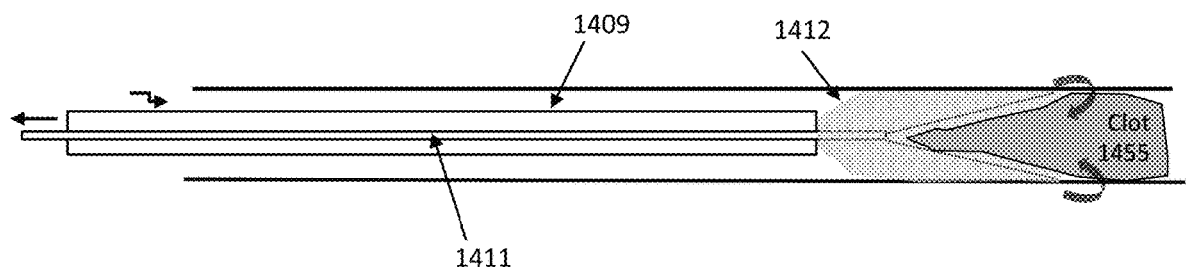

FIGS. 14A-14D illustrate and alternative to the "clot grabbing" tractor tube in which the region of the tractor tube that is proximal to the expanded outer tractor tube portion is shape set into a taper in the relaxed, otherwise expanded, configuration. For example, in FIG. 14A, the apparatus is configured as a single-axis system within a vessel 1402. In operation, the apparatus is delivered within the vessel 1402 through a distal access catheter 1409. A guidewire may also be used to position the apparatus. In FIG. 14A, the apparatus is compressed within the distal access catheter and slid or otherwise driven through the vessel to the clot 1455. The tractor tube 1405 is compressed, but is pre-rolled around itself with a distal-facing end region at the distal end of the device that may be positioned in proximity to the clot 1455 in the vessel. The inner tractor tube portion is attached to an inner tractor puller 1411. In this single axial system shown, the distal access catheter 1409 also acts as the outer tractor pusher once the tractor is pushed out of the catheter and expanded, as shown in FIG. 14B.

Figure 14D:
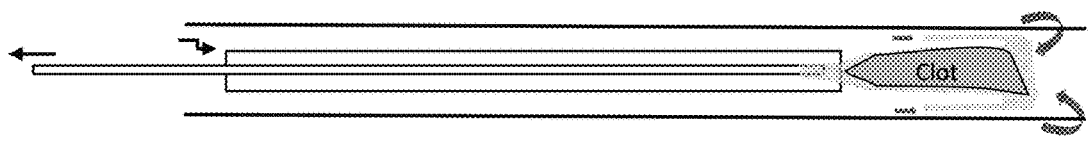

In FIG. 14B, the distal access catheter may be withdrawn proximally and/or the rest of the apparatus may be pushed distally, allowing the distal access catheter to release and deploy the apparatus so that the outer tractor tube portion 1403 can expand to a diameter that is within +/−30% of the outer diameter of the distal access catheter/outer tractor pusher 1409. In this example, the distal access catheter is withdrawn proximally past the outer, proximal end of the tractor tube portion, showing that this end of the tractor tube is pre-set to a tapered shape 1412. Thus, in FIG. 13C, the distal access catheter (outer tractor pusher) may be advanced distally back over this tapered region, to either drive the outer tractor tube portion distally or to brace against the tapered portion and hold the outer tractor tube portion in position while pulling the inner tractor tube portion proximally, as shown. Thus, in FIG. 14C, the distal-facing region of the tractor tube forms a conical shape as it inverts on itself when the inner tractor puller is pulled proximally and/or the outer tractor pusher (distal access catheter) is pushed distally. By continuing to pull inner tractor puller and/or hold the inner tractor puller and push the outer tractor pusher (or some combination of both movements), the conical shape formed on the tractor tube behaves like a conveyor, thereby "grabbing" the clot and pulling the clot into tractor tube (e.g., engulfing the clot/capturing the clot). Once the tractor tube is inverted, it (along with the captured clot) can be pulled into the distal access catheter, as shown in FIG. 14D. In FIG. 14D, the inner tractor puller can be fully retracted and the tractor tube can be removed from the patient out of the distal access catheter.

Figure 15A:
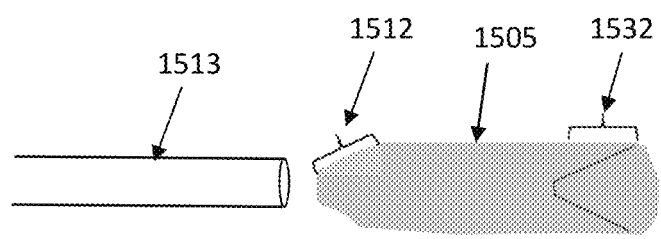
FIG. 15A illustrates an example of a tractor tube including an outer tractor tube portion that is tapered forming a face that me braced against an outer tractor pusher. The distal end of an exemplary outer tractor pusher is shown for reference.
Figure 15B:
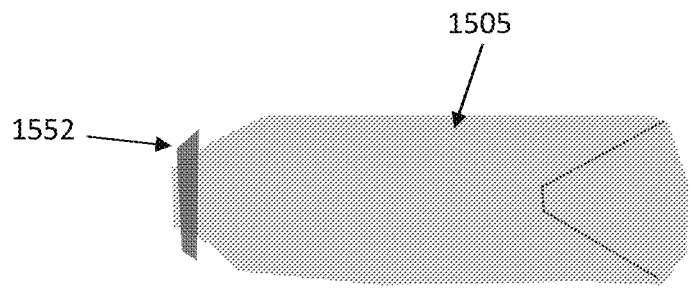
FIG. 15B is an example of another example of an outer tractor tube portion including a collar (shown as a ring) that forms a tapered shape at the proximal end of the outer tractor tube portion or a tractor tube.

FIGS. 15A and 15B illustrate variations for forming the pre-set tapered regions of the tractor tube proximal to the expanded outer tractor tube portions. In FIG. 15A, the tapered proximal region 1512 is shown with a rolled distal-facing end region 1532. In this example, the maximum outer diameter is within a predefined range of the outer diameter of the outer tractor pusher catheter 1513 is within a pre-defined percentage (e.g., between about +/−5%, 10%, 15%, 20%, 25%, 30%, 35%, 40%, 45%, 50%, etc. of the outer diameter of the distal access catheter 1513). The tapered distal region 1512 may be formed by shape setting to the tapered shape. Alternatively, as shown in FIG. 15B, the apparatus may include a limiter, such as a ring, neck, band, etc. 1552 that limits the expansion of the tractor tube portion.

For example, in FIG. 15B, the proximal end of the tractor tube 1505 on the outside of the tractor tube includes a polymer and/or metal ring 1552 or bulking agent to increase the effective wall thickness of the proximal end of the tractor tube, making it easier for the distal end opening of the distal access catheter to engage with this proximal end of the tractor tube, and may also support and allow for easier pushing of the construct, and/or prevent the failure mode shown in FIG. 8B, above. This can be achieved by bonding, fusing or integrating a separate element into the proximal end of the tractor tube (e.g., stent, O ring, beading of glue/adhesive, fusing or melting a polymer ring or by inverting the braid so the braid is doubled up on the proximal end, making the wall thickness thicker). Alternatively or additionally, the ends of the braid at this proximal end may be left open and even purposely frayed to provide filaments that would easily catch on the distal end of the distal access catheter when trying to push the tractor tube distally.

In general, the self-rolling apparatuses described herein may have a jammed braid angle on the outside of the tractor tube (e.g., a maximum diameter of the braid). The braid's maximum diameter during axially compression may be slightly smaller and/or larger than the vessel ID (e.g., it may have the same OD, >5% bigger, >10% bigger, <5% smaller, <10% smaller, <20% smaller, <30% smaller, etc.). This may facilitate the structure advancing when pushed forward. Examples of high braid angles range from 80-170 deg, or by an increment within that range by 10 deg or more. For example, a tractor tube for an M1 vessel (e.g., 2-2.5 mmID) may have 36 braid ends of 0.001" NiTi wire formed onto a 2 mm mandrel at max braid angle. This tractor tube may be annealed to this shape on the 2 mm mandrel. In another example, a tractor tube may be formed for an M1 vessel (e.g., 2-2.5 mmID), from 48 braid ends of 0.0005" by 0.001" of flat wire onto a 2.5 mm mandrel, at max angle. In another example, a tractor tube for an M1 vessel (e.g., 2-2.5 mmID) may have a braid of 48 ends of 0.0005" by 0.001" flat NiTi wire onto a 2.5 mm mandrel, near max angle, that is removed from mandrel, and slid over a larger mandrel of 2.75 mm (e.g., to increase braid angle to a jammed braid angle). In another example, for a larger vessel (e.g., 3-3.5 mm ID), a braid having 72 ends of 0.0005" by 0.001" of flat NiTi wire may be formed onto a 3 mm mandrel, near max angle, removed from the mandrel, and slid over a larger mandrel of 3.5 mm (to increase braid angle to a jammed braid angle). For much larger vessels (e.g., 5-8 mm) a 72 ends 0.002"-0.003" NiTi wire, having a max braid angle on 5-8 mm mandrel may be formed.

In general, the tractor tube may be formed of flat wires; this may help create a grabbing edge when the braid rolls. In addition, radiopaque wires can be mixed into the pattern for visibility under flouro (e.g., platinum, platinum iridium, DFT wire, gold, marker bands or beads, etc.). Any of these apparatuses can be delivered pre-loaded inside the distal access catheter and/or separately (e.g., using a secondary catheter after the distal access catheter is in position) delivered.

Any of the tractor tubes may be coated with a flexible material like urethane, silicone or other elastic element. A coating can be throughout the entire tractor tube length and/or thickness or partially on the length, e.g., just on one surface (such as inside or outside of the structure). In one embodiment, the tractor tube surface that touches ID of the distal access catheter wall when rolled around the catheter tip may not have a coating (as this surface touches the clot), while the other surfaces may have a coating or lamination. These coatings may cover all the interstices of the structure so aspiration/vacuum could be applied through the inner tractor puller and/or the distal access catheter to get a vacuum force to the clot. The coating could also include a hydrophilic coating to help make the CGS more lubricous for rolling on itself.

Figure 16A:
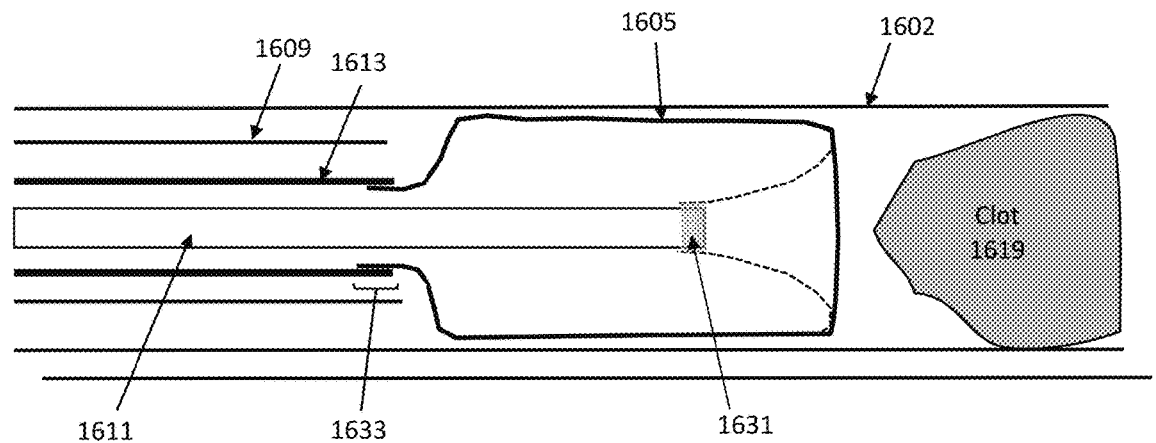
FIGS. 16A-16C illustrate another example of a self-rolling mechanical atherectomy apparatus in which the proximal end of the outer tractor tube portion of the tractor tube of the apparatus is releasably attached to an outer tractor pusher, e.g., by bonding with a frangible material, mechanical connection, dissolvable connection, etc. In contrast, the proximal end of the inner tractor tube portion of the tractor tube may be permanently bonded to an inner tractor puller, as shown in FIG. 16A.
Figure 16B:
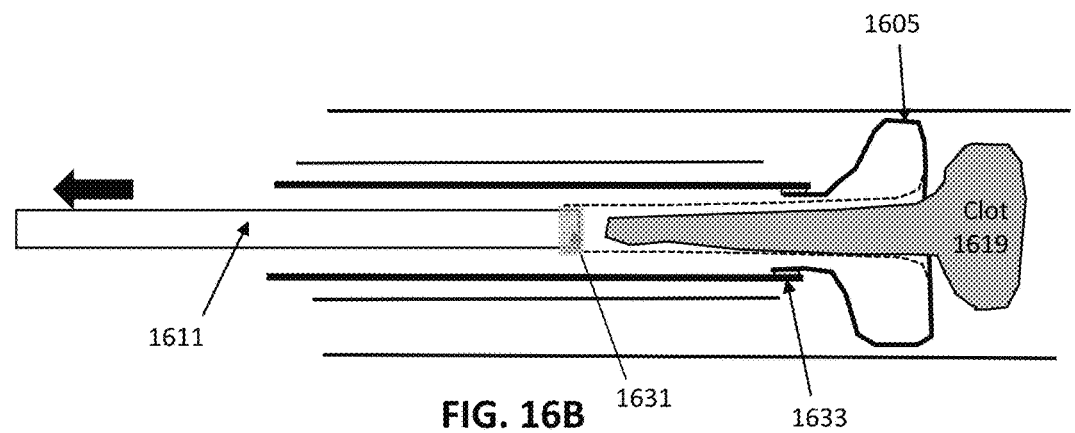
Figure 16C:
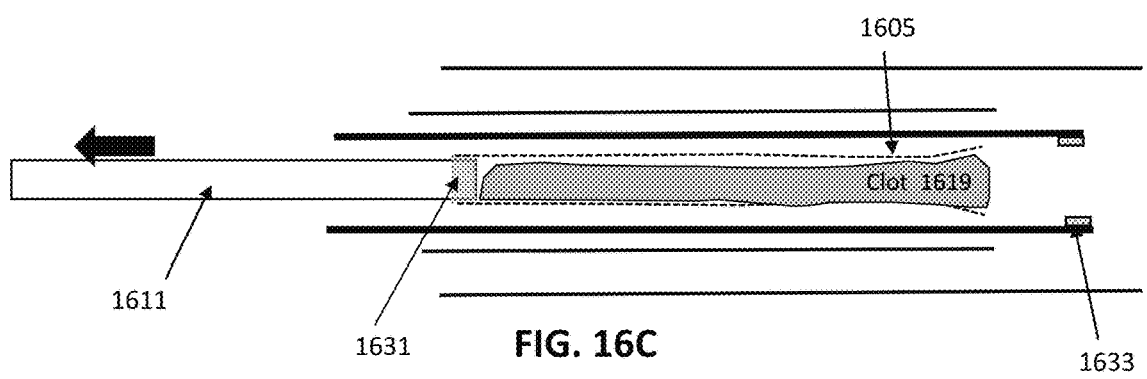

In any of the apparatuses described herein, the proximal end of tractor tube may be temporarily attached to the distal end of the outer tractor pusher (in some variations, the distal access catheter). For example, a temporary bond or connection between the end of the tractor tube and the outer tractor pusher may allow the tractor tube to push and maybe pull the tractor tube distally and proximally; however, when the tractor tube is fully inverted, the tractor tube may be released from the distal end of the outer tractor pusher, allowing the user to pull out both elements separately (e.g., the outer tractor pusher and the tractor tube). FIGS. 16A-16C illustrate one example of this. In FIG. 16A, the apparatus includes a distal access catheter 1609 that has been withdrawn over a separate outer tractor pusher 1613 within the blood vessel 1602. The outer tractor pusher is temporarily attached 1633 (e.g., by a frangible bond or connection that is fused, adhesive and/or a mechanical connection) to and end of the tractor tube 1605, and particularly the end that is proximal to the outer tractor tube portion, which is shown expanded in this example. The opposite end of the tractor tube is permanently attached 1631 to the distal end of an inner tractor puller 1611. The apparatus is shown deployed within the vessel adjacent to a clot 1619.

In FIG. 16B, the inner tractor puller may be withdrawn proximally as describe above to grab the clot and withdraw it into the tractor tube as it is rolled from the outer tractor tube portion into the inner tractor tube portion. Once the entire outer tractor tube portion has been rolled and inverted into itself, the connection to the outer tractor pusher may be broken, as shown in FIG. 16C, so that the entire tractor tube may be withdrawn into the outer tractor pusher and distal access catheter, as shown.

Figure 26A:
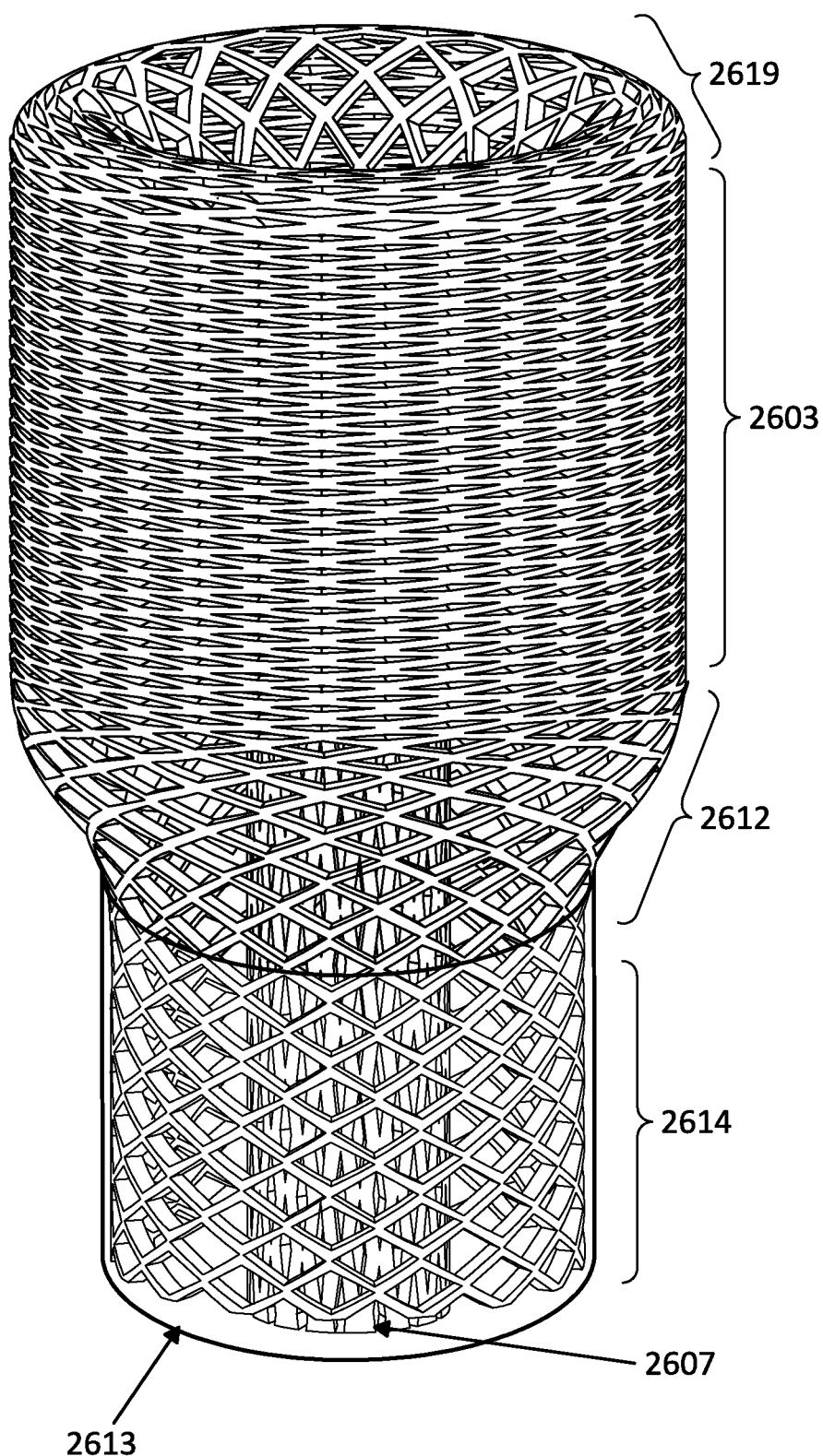
FIG. 26A illustrates another example of a tractor portion of a self-rolling mechanical atherectomy apparatus, showing properties of different regions ("zones") of the tractor tube in different configurations, including an inner tractor tube portion that stretches in tension, a distal-facing region between the inner tractor tube portion and the outer tractor tube portion, a high column strength outer tractor tube portion, a constrained region at the proximal end of the outer tractor tube portion, and a transition zone between the high column strength outer tractor tube portion and the constrained region.

FIGS. 26A-26C and 27A-27B illustrate examples tractor tubes that are formed from slotted tubes (e.g. tubes formed with slot or openings cut through them). The same general properties described above for woven/braided tractor tubes may be applied to rolled/cut or otherwise formed tractor tubes. For example, in FIG. 26A, the tractor tube may be formed of a tube of material into which slots and pores (windows) through the tube have been laser cut. The material may initial be a sheet of solid (e.g., nickel titanium) material. In FIG. 26A, the tractor tube includes a distal-facing region 2619 is the rolling zone of the tractor tube, the region where the outer tractor tube portion 2603 rolls and inverts to become the inner tractor tube portion 2607. The cuts in the sheet of material form quadrilaterals arranged with a "braid angle" (in this variation, a cut angle) that converts from the very large braid angle in the compressed outer tractor tube portion 2603 to a much smaller braid angle in the inner tractor tube region.

The expanded outer tractor tube region 2603 shows that the angles of the pores (the braid angle) arranged in the proximal-to-distal axis have an angle of between 80-170 degrees, as described above. In This example, the angle is approximately 165 degrees. The cut-out pores are approximately diamond shapes and the entire circumference is cut with these shapes, forming a larger diameter, flexible cylindrical column structure that has a very high column strength. Just proximal to the expanded outer tractor tube region 2603 is a tapered region 2612 that is a transition zone between a smaller diameter region that is constrained to have a smaller diameter (e.g., by the outer tractor pusher and/or the distal access catheter). The length (along the distal-to-proximal axis) of this tapering transition region 2612 may be approximately 0.25× to 2× the diameter (outer diameter) of the outer tractor tube region 2603.

As mentioned, the constrained region 2614 may be constrained so that it cannot expand radially (unlike the expanded outer tractor tube region), and may also be held to the outer tractor pusher by a releasable bond, as described above in FIGS. 16A-16D. This region may be held within the outer tractor pusher 2613.

Figure 26B:
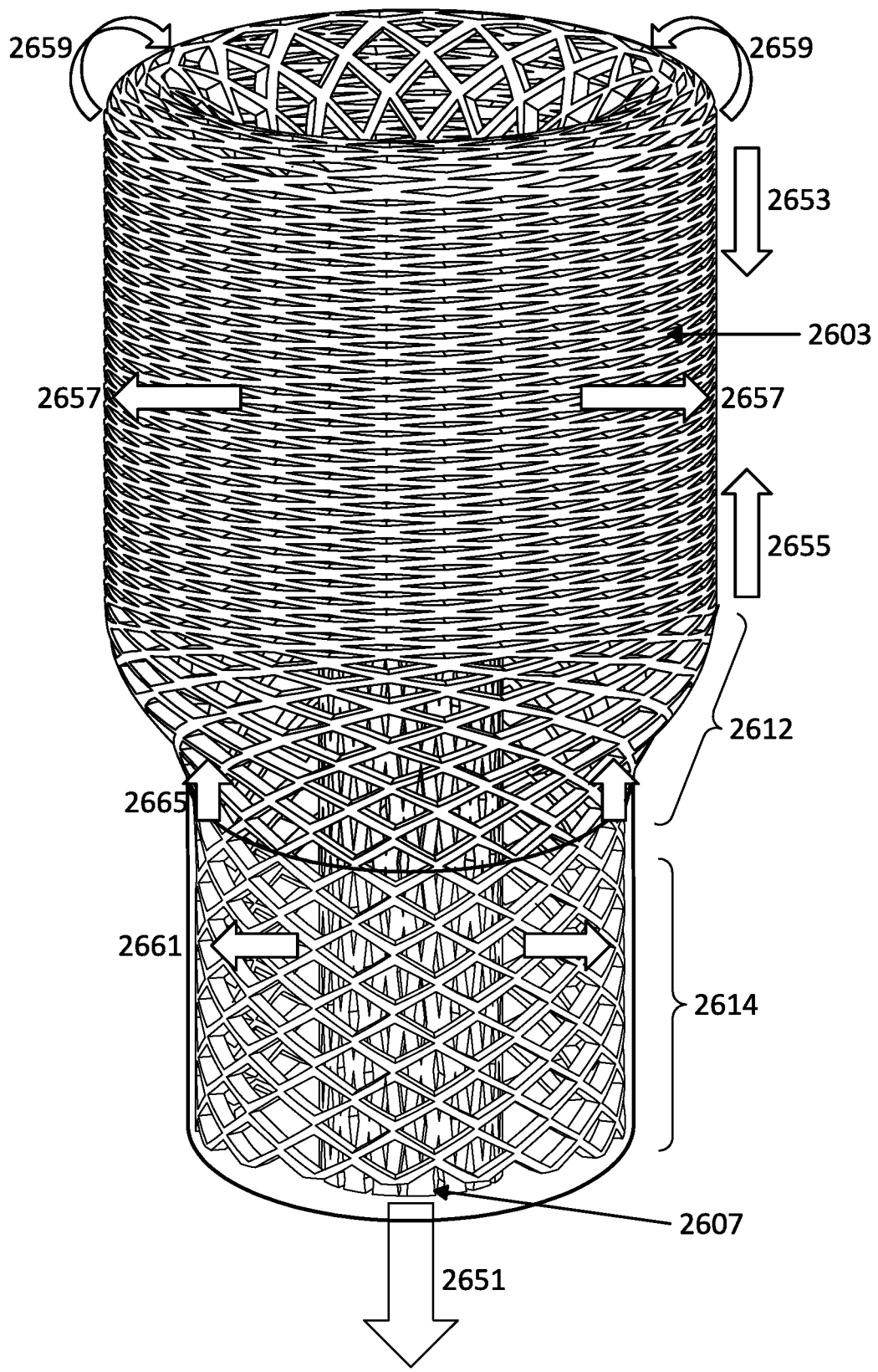
FIGS. 26B and 26C illustrate the functional operation of the different regions ("zones") of the self-rolling mechanical atherectomy apparatus shown in FIG. 26A. Pulling on the inner tractor tube portion (e.g., by pulling on the inner tractor tube portion itself or on an inner tractor puller to which it is attached) causes the outer tractor tube portion closest to the distal-facing region of the tractor tube to roll over itself and invert into the inner tractor tube portion; at least in part because of the high column strength of the outer tractor tube portion and the strength of the transition zone preventing the tractor tube from collapsing (as shown in FIGS. 7A-7B and 8B).

FIG. 26B illustrates the rolling movement of the variation shown in FIG. 26A when the inner tractor tube portion 2607 is pulled proximally 2651. In this example, pulling the inner tractor tube portion proximally results in the elongation and tension on the inner tractor tube portion, putting compression (by the forced pulling down 2653 from the inner tractor tube portion, and the opposing force 2655 from the outer tractor pusher 2613) on the outer tractor tube portion 2603. The compressive force as well as the biasing force from the tractor tube maintains the expansion 2657 of the outer tractor tube portion. Pulling the inner tractor tube proximally and holding the outer tractor pusher (or pushing it distally) results in rolling 2659 of the distal-facing region of the tractor tube, causing it to collapse and fold back onto itself, as shown. The outer diameter of the outer tractor tube portion is therefore compressed to a minimum axial (distal-to-proximal) length, and a jammed maximum diameter, as shown. The constrained region 2614 is held within the outer tractor pusher 2613 by the constraining force 2661 against the inner diameter of the outer tractor pusher. The outer tractor pusher also applies a force 2665 against the tapered region 2612.

Figure 26C:
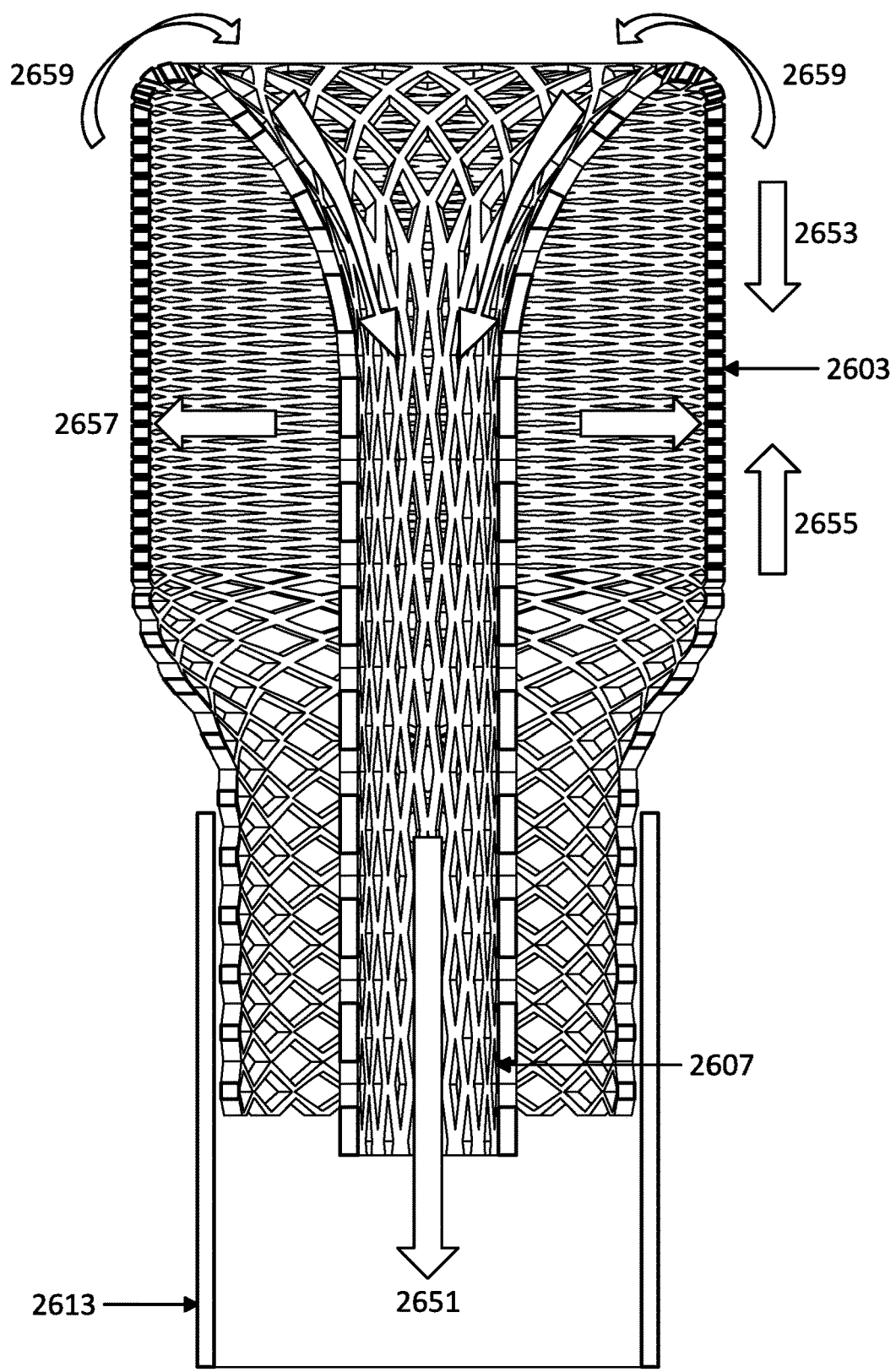

The sectional view of FIG. 26C provides additional detail, showing the transition between the outer tractor tube portion 2603 and the inner tractor tube portion 2607. As shown, the outer regions of the tractor tube (e.g., the constrained region, the tapered region and the outer tractor tube portion 2603)

are all in compression while the inner regions (e.g., the inverting region and the inner tractor tube portion 2607) are in tension, causing rolling of the tractor tube.

FIGS. 27A-27B show views looking down the long axis of the tractor tube form the distal end and the proximal ends, respectively. In FIG. 26C, the transition in the cut angles ("braid angles") between the outer tractor tube portion and the inner tractor tube portion at the distal-facing region of the tractor is apparent. FIG. 28 is a transparent view of a tractor tube showing the regions discussed above. In FIG. 28, the tractor tube includes the distal-facing region 2819 which forms a funnel-shape 2841 as it transitions from the expanded outer tractor tube portion 2803 to the inner tractor tube portion 2807. The inner funnel region could be formed/shaped and/or laser cut to be more similar in diameter to the ID of the outer tube, as described above. Thus, the inner tractor tube diameter could be biased to expand to a particular diameter (e.g., a fraction of the constrained tractor tube region, such as 30%, 40%, 45%, 50%, 60%, 65%, 70%, 80%, etc., or a fraction of the unconstrained outer tractor tube portion, etc.). In FIG. 28, the shape outline also shows the constrained region 2814, and a tapered region 2812 that is proximal to the expanded outer tractor tube region 2803. As already mentioned above, the tractor tubes may be formed from braid, knit, fabric tube, polymer extrusion, etc.

For example, any of the tractor tubes described herein may be formed from a laser-cut tube material. Examples of slotted laser cut tubes forming a tractor are provided herein, including those shown in FIGS. 17A-25B. The starting tubes may be flexible or rigid. For example, a soft flexible tube, strip, or roll of material such as ePTFE or a dense fabric (e.g., knit or weave or braid) may be used. Flexible tubes may provide tractors and/or combinations of tractors and catheters that allow tracking of the apparatus to the treatment site even in tortious vessels. Tracking allows pushing of the apparatus through tortuous vessels of small caliber over long distances from their introduction site to the human body, over length that can exceed 1 meter in some uses. A flexible tube (pre-laser cutting to form the tractor) may have a softness resulting in a low radial crush force, such as a micro-porous, polymer based tube. The tube may be processed (e.g., by cutting or any of the other techniques mentioned herein) to provide flexibility (e.g., the ability to pull the tractor into catheter, invert, and expand over catheter outer diameter) and/or to create a textured/porous surface that may aid in engaging/grabbing a clot (e.g., emboli) and may provide free spaces (voids) that may help store and/or masticate emboli, making them easier to store within the apparatus and transport. Prior to forming into the tractors the sheets or tubes (e.g., films, rolls, etc.) may have a smooth surface. Patterns may be formed into the sheet or tube to form the tractor. For example, laser slot patterns may be formed in the material to increase macro-surface roughness. Holes, slots, edges, divots, and bumps may be formed on the material. In addition to helping grab and hold emboli, such holes or slots may create free space in the tube wall to cut the clot and/or carry it away. The patterns used to form any of the tractors described herein may have a shorter strut length to strut width ratios. Short, wider struts may create tractors that are stiffer and may grab clot better. In combination with strut length to width, in some variations, thicker walls may be preferred. Thicker slotted walls may create stiffer struts and more aggressive surface texture to grab clots. Furthermore, thicker slotted walls may enhance clot storage capacity within the slot gaps.

In some variations, it may be beneficial to provide slot designs which do not foreshorten. For example, if the slotted tube design is pulled axial (e.g., down its length), the tube diameter may not decrease. A decreasing diameter slotted tube may grab the outside of the catheter and cleat, increasing drag force when the tube is pulled.

In variations in which the initial tube or sheet of material used to form the tractor tube is relatively rigid (e.g., formed of a material such as Steel, Nitinol, Polyester, PTFE, Nylon, etc.), the initial tube stiffness/hardness may enhance the clot-grabbing ability when the tractor is slotted properly, to allow both increased flexibility, expansion and rolling. For example, a rigid tube may include slot designs that focuses in catheter tracking and creates a flexibly bending tractor with minimal foreshortening, that is able to be pulled into a catheter (inverting) structure. As with the more flexible starting tubes discussed above, tractors formed of more rigid starting materials may grab and transfer a clot, and the number of slots and/or voids may be increased to increase clot grabbing and/or carrying capacity. A slotted tube forming a tractor may include surface grabbing features, such as channels/corrugations (e.g. any of the microstructures such as those shown in FIGS. 12A-12I above. More rigid tubes may create harder or stiffer slotted tractors. For example, when struts are formed into the tractor (e.g., by cutting, etc.), the slot strut length to strut width may be greater than with less rigid starting materials, and may be a function of the rigid tubes elastic modulus. Higher elasticity materials (e.g., Niti, PET, PTFE) may have strut length to width ratios from 10 to 100. Stiffer materials (e.g., steel, MP35N) may have a length to width ratio greater than 50. The wall thickness to strut width ratio for elastic materials may be, for example, between 0.5 to 10. For stiffer materials, the wall thickness to strut width ratio may be, for example, between 0.25 to 5.

As mentioned, any of the apparatuses described herein may include a tractor region that is non-foreshortening. The foreshortening of the tractor may depend at least in part on the slot designs for non-woven, non-braided, non-knitted designs (e.g., tractors that are not formed of a strand or strands of material). FIGS. 17A-17D illustrate an example of non-foreshortening design. Also, for both flexible and rigid starting tubes forming a non-woven tractor, the tube inner diameter can be slightly bigger then catheter tube outer diameter pre-slotting. Slotted tube designs which foreshorten may reach their smallest diameter limit when tensioned axially. If the tube is sized to be slightly larger than the catheter outer diameter, then it may jam (preventing any foreshortening) before it cleats to the catheter outer diameter. Tractor regions formed of an initially rigid material may grab clot more efficiently than tractors having an equivalent thickness but formed of a more flexible material, although more flexible materials may deform as a function of stiffness.

Figure 17A:
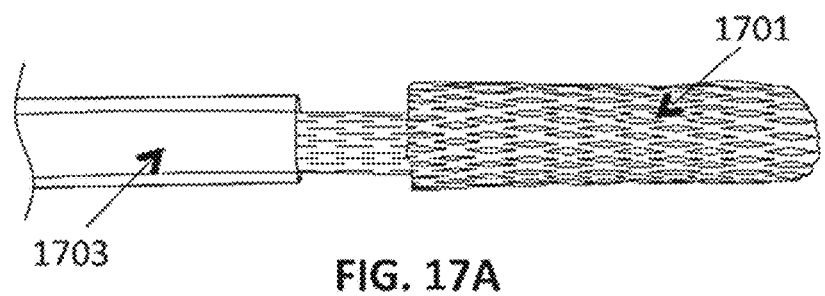
FIGS. 17A-17D illustrate exemplary tractor tubes formed by cutting (e.g., laser cutting) a tubular material.

FIGS. 17A-17D illustrate an example of tractors that are formed by cutting slots and/or windows into tubes of material. In FIGS. 17A-17D, an initially soft material (e.g., ePTFE) was formed by a subtractive manufacturing technique to from, slots, pores and textures in the soft flexible tube. In FIGS. 17A-17D, a 3 mm ID ePTFE tube (configured to be used with a 2.9 mm OD catheter) was made to be highly flexible and have some level of column stiffness and radial/hoop stiffness by laser-cutting slot patterns into the tube wall to create textures and bend zones which impart clot grabbing and rolling. The ePTFE itself is highly lubricous. Addition of a lubricant (e.g., hydrophilic coating) may improve tracking and rolling. Lubricant can be applied to ID and OD or to either separately. FIG. 17A shows a first pattern 1701, having minimal cuts to create a smooth rolling of the tractor around the catheter 1703 portion of the apparatus.

Figure 17B:
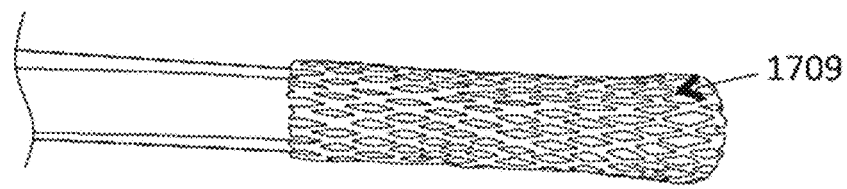

A second exemplary pattern is shown in FIG. 17B. In this example, the apparatus slightly larger cut-out regions 1709 (removed by laser cutting in this example), which may create better clot grabbing properties and more clot holding capacity. In FIG. 17B, the ePTFE tube forming the tractor region is slotted on the outside of the catheter. Note that the porosity (14 holes around the circumference) may help grab and hold colt. In both FIGS. 17A and 17B, the laser pattern may foreshorten, but may jam before it grips/cleats the catheter outer surface.

Another example of a tractor was made from a 2.9 mm OD ePTFE tube (configured for use with a 3 mm ID catheter). This example was made to be highly flexible and have some level of column stiffness and radial/hoop stiffness by laser-cutting slot patterns into the tube wall in a pattern to create textures and configured to include bend zones which impart clot grabbing and rolling. Similarly, a tractor may be made of, e.g., a 2.9 mm OD PET woven fabric tube (for use with a 3 mm ID catheter). The tractor may be formed of 30 Denier PET multi-filaments, 0.003" thickness. The resulting tractor may be configured to be soft and have some level of column stiffness and radial/hoop stiffness by laser cutting slot patterns into the tube wall in a patterns providing texture and bend zones which may impart clot grabbing and rolling. As with ePTFE, the PET material may itself be lubricous although additional lubricant may be added to improve tracking and rolling. Lubricant can be applied to ID and OD or to either separately.

An example of a tractor made from a somewhat rigid starting material was formed from a nickel titanium (NiTi) tube having a 3 mm OD (which may be used with, e.g., a 2.9 mm ID catheter). The wall thickness in these examples was between 0.001" and 0.002". Laser slot patterns were cut into the tube wall in various patterns to create textures and purpose-designed bend zones which may help impart clot grabbing and rolling. A lubricant may be applied, e.g., as a coating, to the ID and OD or to either separately. A first pattern similar to that shown in FIG. 17A was made by minimal laser cutting to create a smooth rolling tractor, with a strut length to width ratio between 25-50. A second pattern having larger slots/openings (similar to that shown in FIG. 17B) was formed by laser cutting. These patterns may foreshorten, but typically minimize or stop foreshortening before the tractor grips/cleats the catheter outer surface (which may result in jamming). The Niti design has the additional benefits of radiopacity, thermal shaping and super elasticity.

Any of these designs or patterns may for projections that may extend from the rolling distal-facing and inverting portion of the tractor, as discussed above. Such projection may be cut out as "teeth" or elongate members. The regions forming the projections may be sharp, e.g., pointy and/or cutting. Sharp projections may be chew and cut a mature clot. These projections regions may be short or long, may extend in one or more directions (e.g., forward or backward or bidirectional), and may be scoop-shaped (e.g., paddle-shaped). The number of projections may be selected based on the desired coarseness, e.g., the number of projections, the size (length/width/thickness), etc. The projections may change density down their length. For example, the laser pattern can be designed to allow tractor rolling (e.g., long struts) more easily initially, then have grabbing teeth at higher density; alternatively the tractor may be configured for greater initially grabbing, having a pattern with more and/or larger projections initially (distally) then transitioning to more slits (and flexibility) toward the proximal end, which may make it easier to pull. Further, the distribution of projections can be uniform around the tube perimeter and/or non-uniform (e.g., forming a spiral pattern, distributed in patches, having open areas, etc.).

Any of the tractors described herein may include a marker or makers (e.g., radiopaque markers, such as gold, Pt, etc.). When forming the tractor from a tube or sheet, the tubes may be be cut, then shaped to have any profile, such as straight, rolled over the tip, flaring at the proximal end, etc. Any of the microstructure described herein may be included or formed, as mentioned above, e.g., wells on the struts may help carry and grab clot. Tractors formed of tubes from which material was removed (or sheets formed into tubes) may be configured to have less cleating of the tractor onto the outer diameter of the clot, preventing jamming, particularly compared to woven or braided or knitted materials. However any of the slotted tube tractor configurations described herein may be used with, e.g., in combination with, a braid or knit or polymer sleeve, including either in parallel or in series. In general, any of these tractors may be formed as multi-layers, particular these slotted tube tractors.

For example, a tractor portion of an apparatus may be formed by removing material from a Niti tube that is slightly smaller than the inner diameter of the catheter that it will be used with, or it may be made from a tube that is slightly larger than the outer diameter of the catheters. The tube may be cut with a pattern that increase the coarseness of the outer surface (e.g., to include projections such as struts/scoops/teeth). For example a 0.001" tube wall thickness or smaller may be used.

Figure 17C:
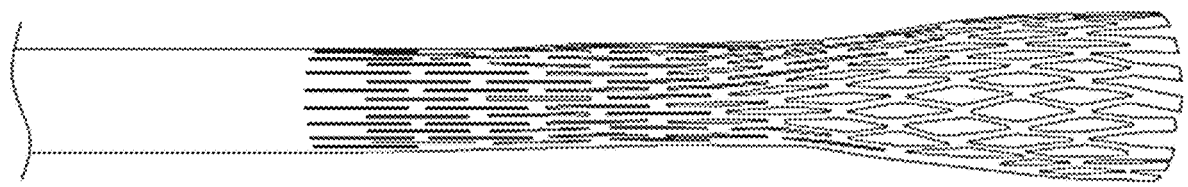
Figure 17D:
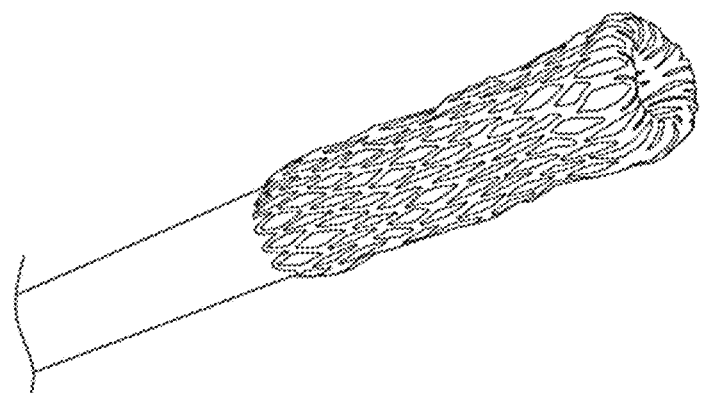

FIGS. 17C and 17D illustrate an example of a tractor region cut from paper. In FIG. 17C a rigid paper tube was cut to include slots and the distal end expanded, a shown. It may be inverted over itself and used as a tractor region. This paper prototype was prepared to illustrate the effectiveness of this pattern. Similarly, FIG. 17D is an example of a prototype tractor region.

Figure 18A:
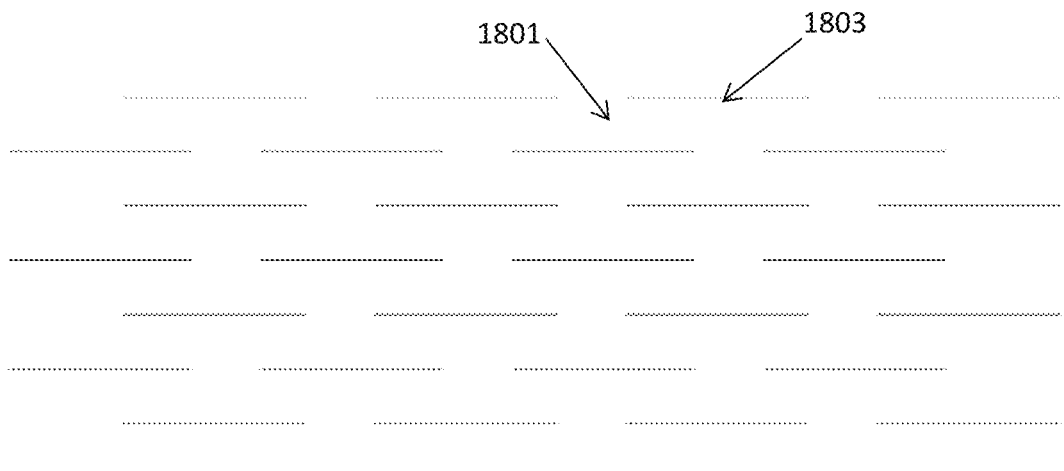
FIGS. 18A-18C illustrate different slotted patterns that may be cut into a tube (or sheet) to form a tractor tube or portion of a tractor tube.
Figure 18B:
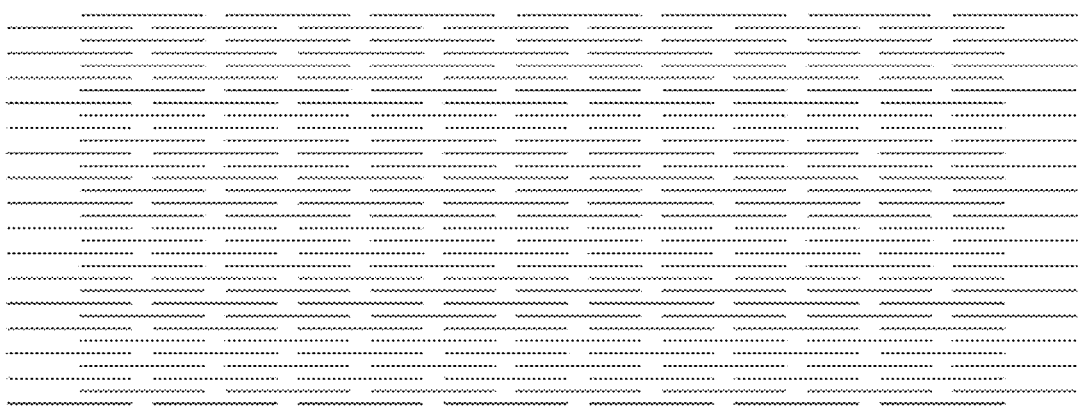
Figure 18C:
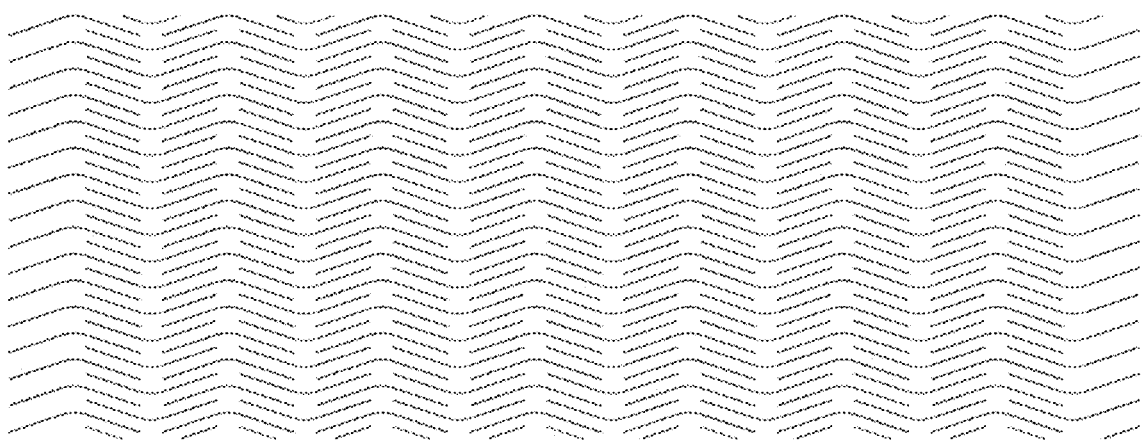

FIGS. 18A-18C illustrate examples of patterns that may be formed into a flat sheet or tubular member to form a tractor (e.g., slotted tractor). Similar to those shown in FIGS. 17A-17D. In FIG. 18A, the pattern may be cut to form the tractor. White regions 1801 may represent or form struts, while the lines indicate slots 1803 from which material is removed. This pattern is one of many resulting in a flexible tube having stout struts. FIG. 18B shows a similar example having a higher density of slots forming thinner struts and potentially higher porosity, which may result in a larger clot-carrying capacity. FIG. 18C illustrates an example of a pattern having curves that may produce a slightly more bendable (flexible in bending stiffness) slotted tractor. In FIGS. 18A-18C, the pattern is oriented so that the distal direction of the tractor formed by the pattern is at the right or left of the pattern shown (e.g., the tube is oriented right and left, relative to the figures, so that the tube is formed by rolling up from the bottom of the figure).

Figure 19:
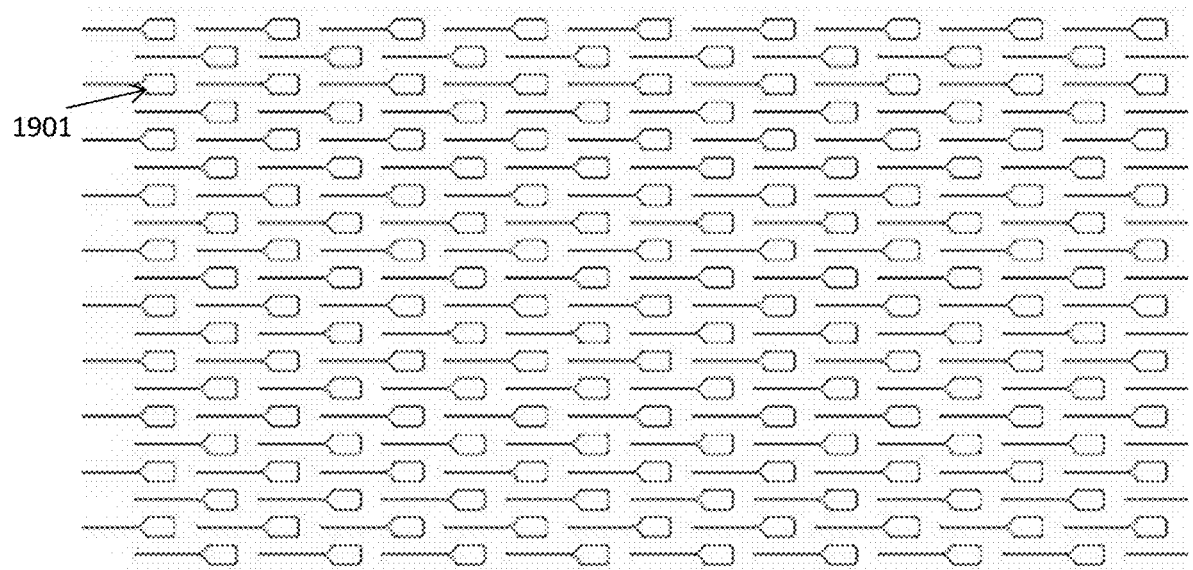
FIG. 19 is another example of a pattern that may be use to form a tractor tube.
Figure 20A:
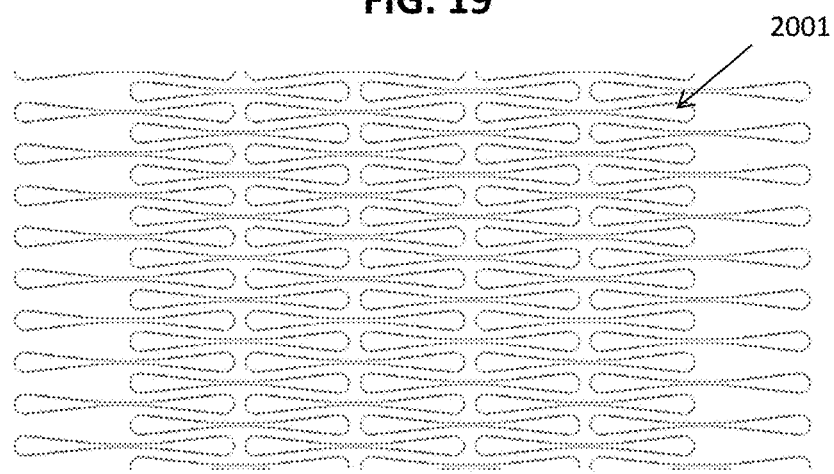
FIGS. 20A-20B show an example of a pattern that may be use to form a tractor tube.
Figure 20B:
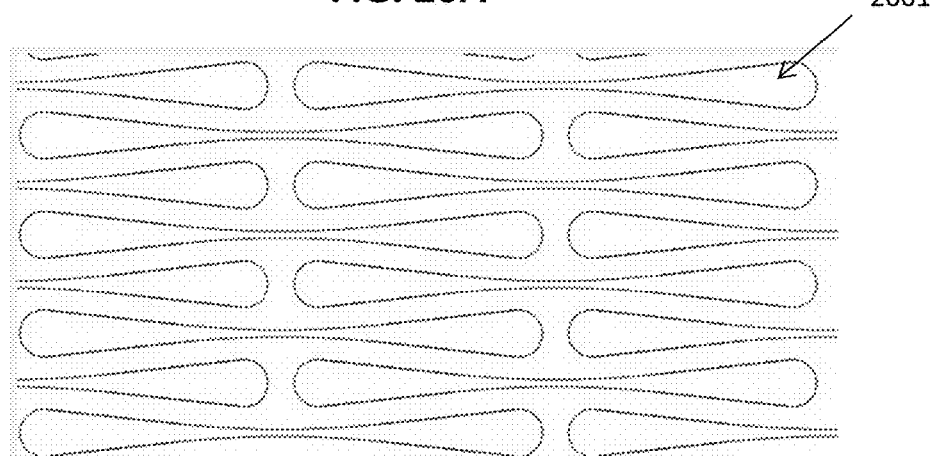
Figure 21A:
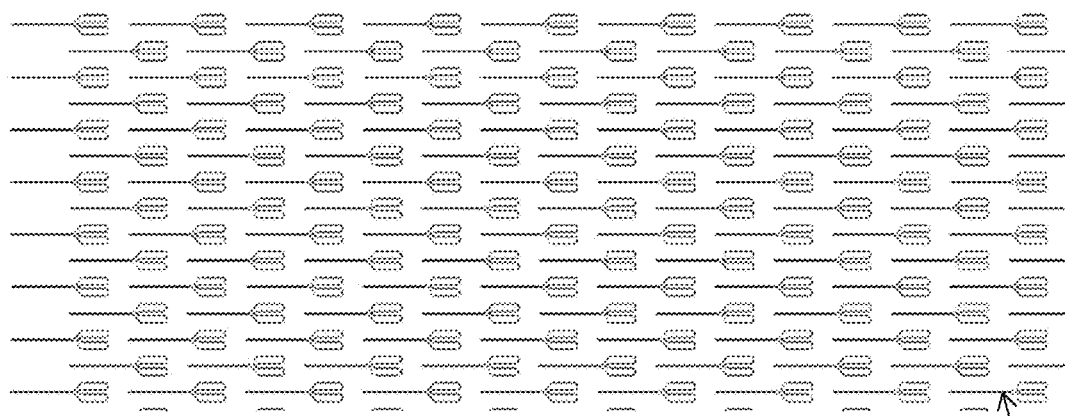
FIGS. 21A-21B show an example of a pattern that may be use to form a tractor tube.
Figure 21B:
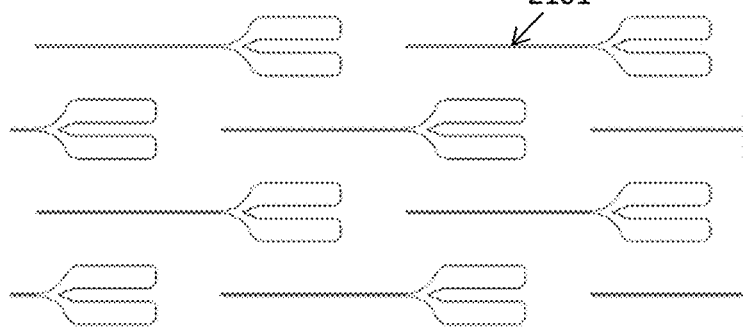

FIG. 19 is an example of a pattern that may be formed into a tube as part of a tractor having a plurality of both slots 1903 and cut-out regions 1901 (holes). Another example of a pattern having a plurality of cut-out holes 2001 formed into it is shown in FIGS. 20A and 20B. FIG. 20B shows an enlarged view.

An example of a pattern having a plurality of projections is shown in FIGS. 21A-24B. For example in FIGS. 21A and 21B, the pattern includes a plurality of slots 2101 and cut-out regions that leave a projecting strut or tooth 2105 behind. In these examples, the tooth 2105 is pointed and oriented to the left of the page, which may be the distal end direction of the tractor. (e.g., the left side of the image may correspond to the distal end of the tractor); thus when the pattern is formed into a tubular body to form the tractor, and the tractor is inverted over itself (e.g., rolling over the distal end opening of a catheter) the plurality of pointed projections 2105 may extend out of the tractor, and may help grab and draw clot into the catheter.

Figure 22A:
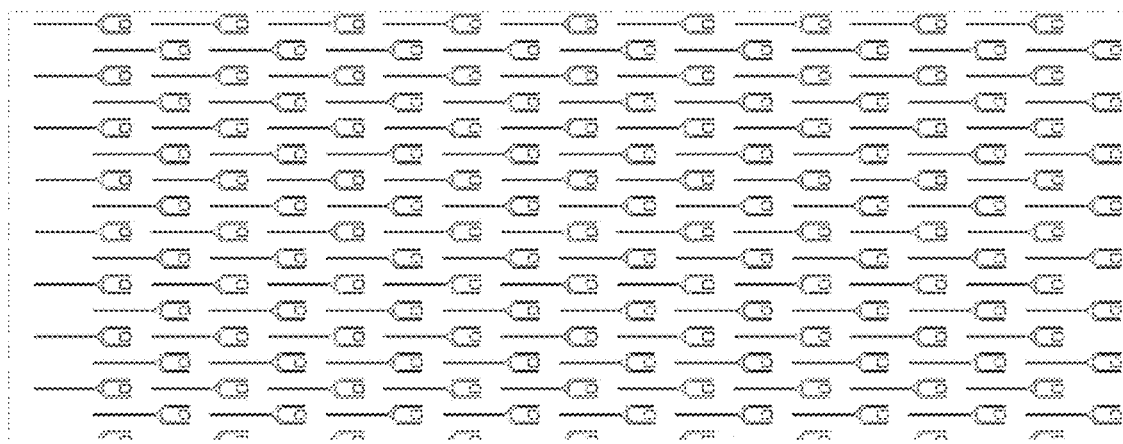
FIGS. 22A-22B show an example of a pattern that may be use to form a tractor tube.
Figure 22B:
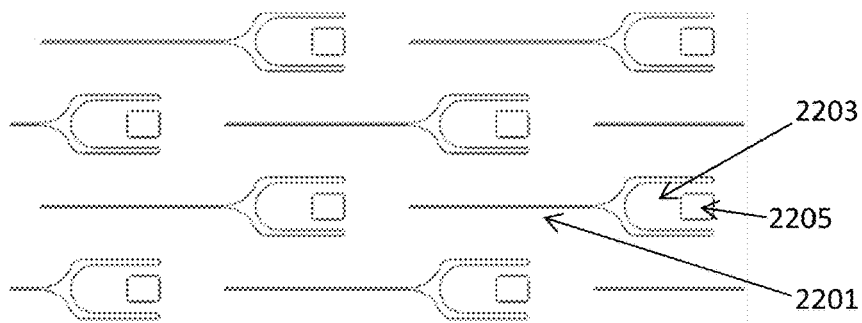
Figure 23A:
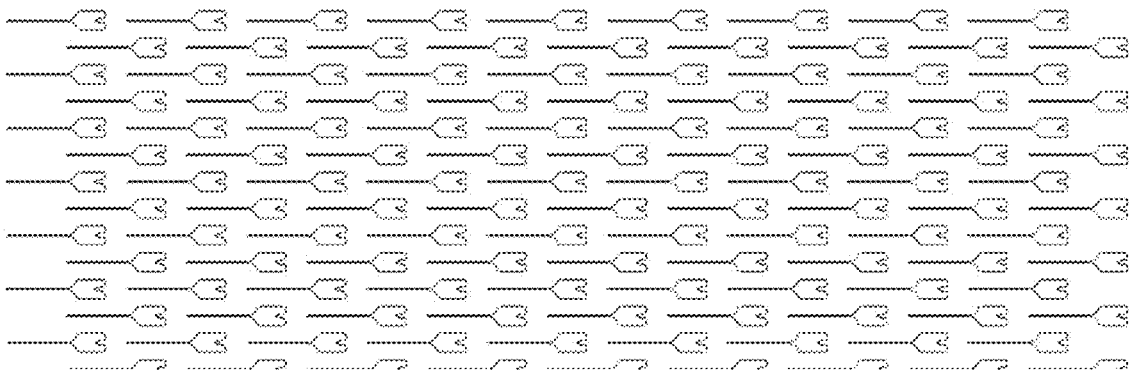
FIGS. 23A-23B show an example of a pattern that may be use to form a tractor tube.
Figure 23B:
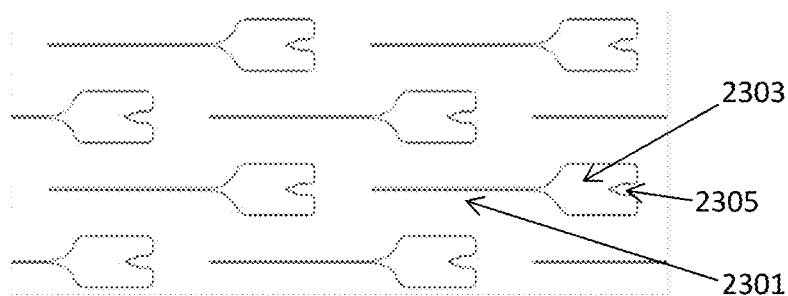
Figure 24A:
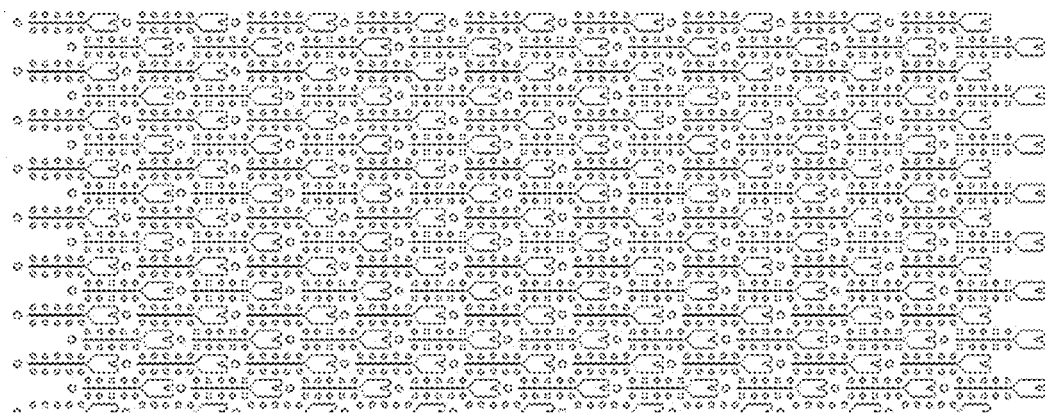
FIGS. 24A-24B show an example of a pattern that may be use to form a tractor tube.
Figure 24B:
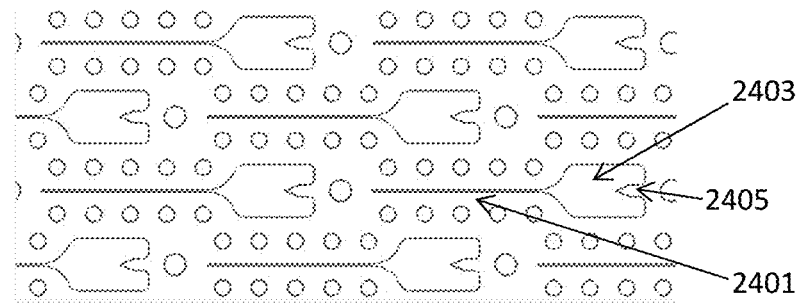

Similarly, the pattern shown in FIGS. 22A-22B illustrate another example include a slot 2201, a projection 2203 and a cut-out portion 2205. As in FIGS. 21A and 21B, the projection may extend out of the plane of the tubular tractor (shown here as the plane of the paper, even when rolled up to form the tractor region). FIG. 23A, and enlarged view of FIG. 24B, shows another example of a pattern for a tractor that is similar to that shown in FIG. 21A-21B, but with smaller projecting regions. In this example, the projections 2305 are sharp, and open into an opening 2303 connected to a slot 2301. The pattern shown in FIGS. 24A-24B is similar to that shown in FIG. 23A-23B but with additional openings (cut out regions 2407) which may increase the carrying capacity (e.g., clot carrying capacity) of the tractor region.

Figure 25A:
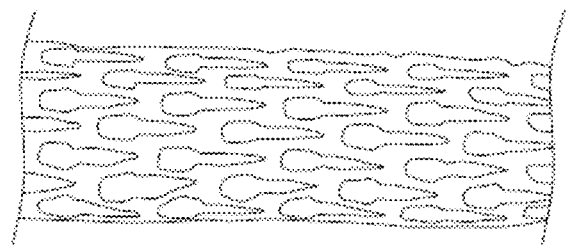
FIGS. 25A-25B illustrate tractor regions having different patterns of slots and openings.
Figure 25B:
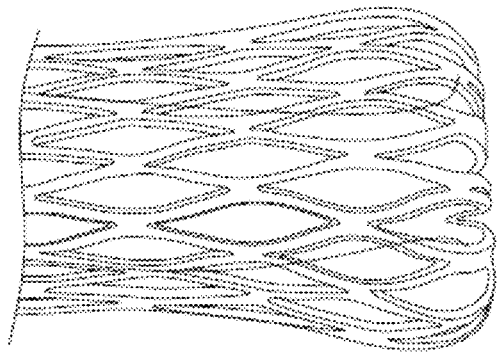

FIGS. 25A-25B are examples of laser-cut tube prototypes of tractor regions. In FIG. 25B the tractor region is inverted over the distal end opening of the catheter.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A self-rolling apparatus, comprising:
    an outer tractor pusher comprising a catheter having a distal end and a distal end opening;
    a tractor tube comprising an outer tractor tube portion that extends distally in an un-inverted configuration and inverts into itself at a distal-facing region to form an inner tractor tube portion,
    wherein the tractor tube is configured such that pulling the inner tractor tube portion proximally (i) compresses the outer tractor tube portion into a configuration having a column strength that resists collapsing, and (ii) causes a region of the outer tractor tube portion at the distal-facing region to roll over itself, unsupported, and invert into the inner tractor tube portion,
    the tractor tube comprising a braided material, wherein the outer tractor tube portion has a braid angle in a proximal to distal axis in a compressed configuration that is between 80 and 170 degrees, and the inner tractor tube portion has a braid angle in the proximal to distal axis under tension of less than 80 degrees; and
    an inner tractor puller coupled to the inner tractor tube portion and extending proximally within the outer tractor pusher.

2. The apparatus of claim 1, wherein the outer tractor pusher is coupled to a proximal end of the outer tractor tube portion of the tractor tube.

3. The apparatus of claim 1, further comprising a distal access catheter, wherein the outer tractor pusher, the tractor tube, and inner tractor puller are held within the distal access catheter in an un-deployed configuration, and wherein the tractor tube is configured to be deployed by being pushed distally out of the distal access catheter so that the outer tractor tube portion expands to a diameter that is greater than an outer diameter of the distal access catheter in a deployed configuration.

4. The apparatus of claim 1, wherein the outer tractor pusher is configured as a distal access catheter in which the tractor tube and inner tractor puller are held within the outer tractor pusher in an un-deployed configuration, and wherein the tractor tube is configured to be deployed by being pushed distally out of the outer tractor pusher so that the outer tractor tube portion expands to an outer diameter that is greater than an outer diameter of the outer tractor pusher.

5. The apparatus of claim 1, wherein the tractor tube is configured so that pulling the inner tractor tube proximally compresses the outer tractor tube portion into a configuration in which the column strength of the outer tractor tube portion resists collapsing up to at least 500 g of compression.

6. The apparatus of claim 1, wherein the outer tractor tube portion of the tractor tube is configured to expand to between about +/−30% of an outer diameter of the outer tractor pusher.

7. The apparatus of claim 1, wherein the tractor tube is formed of between 24-48 filaments.

8. The apparatus of claim 1, wherein the tractor tube is formed of a plurality of filaments, each having a diameter of greater than 0.003 inches.

9. The apparatus of claim 1, wherein the proximal end of the outer tractor tube portion is configured to have a tapered shape when the outer tractor tube portion is expanded radially outward.

10. The apparatus of claim 1, wherein the distal-facing region of the tractor tube is unsupported over at least 1 cm proximally from the distal-facing region of the tractor tube.

11. The apparatus of claim 1, wherein the tractor tube has a porosity of 60% or greater.

12. The apparatus of claim 1, wherein the inner tractor puller comprises an inner lumen configured to pass a guidewire out of a distal end of the apparatus.

13. The apparatus of claim 1, further comprising a vacuum source coupled to the tractor tube and configured to apply a vacuum therethrough.

14. A self-rolling apparatus, comprising:
    an outer tractor pusher comprising a catheter having a distal end and a distal end opening;
    a tractor tube comprising an outer tractor tube portion that extends distally in an un-inverted configuration and inverts into itself at a distal-facing region to form an inner tractor tube portion, wherein the tractor tube is configured so that pulling the inner tractor tube portion proximally (i) compresses the outer tractor tube portion into a configuration having a column strength that resists collapsing up to at least 500 g of compression, and (ii) causes a region of the outer tractor tube portion at the distal-facing region to roll over itself, unsupported, and invert into the inner tractor tube portion; and
    an inner tractor puller coupled to the inner tractor tube portion and extending proximally within the outer tractor pusher.

15. The apparatus of claim 14, wherein the outer tractor pusher is coupled to a proximal end of the outer tractor tube portion of the tractor tube.

16. The apparatus of claim 14, further comprising a distal access catheter, wherein the outer tractor pusher, the tractor tube, and inner tractor puller are held within the distal access catheter in an un-deployed configuration, and wherein the tractor tube is configured to be deployed by being pushed distally out of the distal access catheter so that the outer tractor tube portion expands to a diameter that is greater than an outer diameter of the distal access catheter in a deployed configuration.

17. The apparatus of claim 14, wherein the outer tractor pusher is configured as a distal access catheter in which the tractor tube and inner tractor puller are held within the outer tractor pusher in an un-deployed configuration, and wherein the tractor tube is configured to be deployed by being pushed distally out of the outer tractor pusher so that the outer tractor tube portion expands to an outer diameter that is greater than an outer diameter of the outer tractor pusher.

18. The apparatus of claim 14, wherein the tractor tube comprises a braided material.

19. The apparatus of claim 18, wherein the outer tractor tube portion has a braid angle in a proximal to distal axis in a compressed configuration that is between 80 and 170 degrees, and the inner tractor tube portion has a braid angle in the proximal to distal axis under tension of less than 80 degrees.

20. The apparatus of claim 14, wherein the outer tractor tube portion of the tractor tube is configured to expand to between about +/−30% of an outer diameter of the outer tractor pusher.

21. The apparatus of claim 14, wherein the tractor tube is formed of between 24-48 filaments.

22. The apparatus of claim 14, wherein the tractor tube is formed of a plurality of filaments, each having a diameter of greater than 0.003 inches.

23. The apparatus of claim 14, wherein the proximal end of the outer tractor tube portion is configured to have a tapered shape when the outer tractor tube portion is expanded radially outward.

24. The apparatus of claim 14, wherein the distal-facing region of the tractor tube is unsupported over at least 1 cm proximally from the distal-facing region of the tractor tube.

25. The apparatus of claim 14, wherein the tractor tube has a porosity of 60% or greater.

26. The apparatus of claim 14, wherein the inner tractor puller comprises an inner lumen configured to pass a guide-wire out of a distal end of the apparatus.

27. The apparatus of claim 14, further comprising a vacuum source coupled to the tractor tube and configured to apply a vacuum therethrough.

28. A self-rolling apparatus, comprising:
an outer tractor pusher comprising a catheter having a distal end and a distal end opening;
a tractor tube formed from 10 or more strands, the tractor tube comprising an outer tractor tube portion that extends distally in an un-inverted configuration and inverts into itself at a distal-facing region to form an inner tractor tube portion, wherein the tractor tube is configured such that pulling the inner tractor tube portion proximally (i) compresses the outer tractor tube portion into a configuration having a column strength that resists collapsing, and (ii) causes a region of the outer tractor tube portion at the distal-facing region to roll over itself, unsupported, and invert into the inner tractor tube portion,
wherein the outer tractor tube portion has an expanded configuration with a distal-to-proximal facing braid angle for the expanded configuration of between about 80 and about 170 degrees; and wherein the outer tractor tube portion of the tractor tube is configured to expand to between about +/−30% of an outer diameter of the outer tractor pusher; and
an inner tractor puller coupled to the inner tractor tube portion and extending proximally within the outer tractor pusher.

* * * * *